(12) United States Patent
Rambo et al.

(10) Patent No.: US 8,895,280 B2
(45) Date of Patent: *Nov. 25, 2014

(54) POLYSILICATE-POLYSILICONE ENZYME IMMOBILIZATION MATERIALS

(71) Applicant: Akermin, Inc., St Louis, MO (US)

(72) Inventors: Brett M. Rambo, St. Charles, MO (US); Tracy L. Bucholz, St. Charles, MO (US); Dawn C. Powell, Edwardsville, IL (US); Luke E. Weber, Edwardsville, IL (US); Alexander J. Linder, Fairview Heights, IL (US); Caroline M. H. Duesing, San Antonio, TX (US); Aleksey Zaks, Hoboken, NJ (US)

(73) Assignee: Akermin, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/840,696

(22) Filed: Mar. 15, 2013

(65) Prior Publication Data

US 2013/0267004 A1 Oct. 10, 2013

Related U.S. Application Data

(60) Provisional application No. 61/621,280, filed on Apr. 6, 2012.

(51) Int. Cl.
| | | |
|---|---|---|
| *C12N 11/04* | (2006.01) | |
| *C12M 1/40* | (2006.01) | |
| *C12M 1/00* | (2006.01) | |
| *B01D 53/84* | (2006.01) | |
| *C12N 9/88* | (2006.01) | |
| *C12N 11/08* | (2006.01) | |

(52) U.S. Cl.
CPC ............... *C12N 11/08* (2013.01); *B01D 53/84* (2013.01); *Y02C 10/02* (2013.01); *C12N 9/88* (2013.01); *C12Y 402/01001* (2013.01)
USPC ........ 435/182; 435/174; 435/266; 435/299.1; 435/168

(58) Field of Classification Search
None
See application file for complete search history.

(56) References Cited

U.S. PATENT DOCUMENTS

| | | | |
|---|---|---|---|
| 5,200,334 A | 4/1993 | Dunn et al. | |
| 6,395,299 B1 | 5/2002 | Babich et al. | |
| 6,495,352 B1 | 12/2002 | Brinker et al. | |
| 6,524,843 B1 * | 2/2003 | Blais et al. ................. | 435/266 |
| 6,713,559 B1 | 3/2004 | Armbrust et al. | |
| 7,176,017 B2 | 2/2007 | Parent et al. | |
| 7,579,185 B2 | 8/2009 | Parent et al. | |
| 7,596,952 B2 | 10/2009 | Fradette et al. | |
| 7,642,076 B2 * | 1/2010 | Dziedzic et al. .............. | 435/174 |
| 7,820,432 B2 | 10/2010 | Parent et al. | |
| 8,066,965 B2 | 11/2011 | Fradette et al. | |
| 8,277,769 B2 | 10/2012 | Fradette et al. | |
| 8,329,458 B2 | 12/2012 | Parent et al. | |
| 8,329,459 B2 | 12/2012 | Parent et al. | |
| 8,329,460 B2 | 12/2012 | Parent et al. | |
| 8,435,479 B2 | 5/2013 | Fradette et al. | |
| 8,480,796 B2 | 7/2013 | Fradette et al. | |
| 8,722,391 B2 | 5/2014 | Fradette et al. | |
| 2001/0055797 A1 | 12/2001 | Conroy et al. | |
| 2004/0195710 A1 | 10/2004 | Hubbell et al. | |
| 2008/0095928 A1 | 4/2008 | Salguero et al. | |
| 2008/0241877 A1 | 10/2008 | Ying et al. | |
| 2009/0170180 A1 | 7/2009 | Bond et al. | |
| 2010/0209968 A1 * | 8/2010 | Akers et al. .................. | 435/68.1 |
| 2010/0297723 A1 * | 11/2010 | Borchert et al. .............. | 435/174 |

FOREIGN PATENT DOCUMENTS

WO 00/10691 A1 3/2000

OTHER PUBLICATIONS

Avnir, D., et al., "Enzymes and Other Proteins Entrapped in Sol-Gel Materials," Chemistry of Materials, 1994, pp. 1605-1614, vol. 6, No. 10.
Avnir, D., "Organic Chemistry Within Ceramic Matrices: Doped Sol-Gel Materials," Accounts of Chemical Research, 1995, pp. 328-334, vol. 28, No. 8.
Badjic, J. D., et al., "Effects of Encapsulation in Sol-Gel Silica Glass on Esterase Activity, Conformational Stability, and Unfolding of Bovine Carbonic Anydrase II," Chemistry of Materials, 1999, pp. 3671-3679, vol. 11, No. 12.
Barboiu, M., et al., "Supramolecular Complexes of L-Amino Acids as Efficient Activators of the Zinc Enzyme Carbonic Anydrase," Liebigs Annalen/Recueil, 1997, pp. 1853-1859.
Forsyth, C., et al., "CO2 Sequestration by Enzyme Immobilized onto Bioinspired Silica," Chemical Communications, 2013, pp. 3191-3193, vol. 49.
Frenkel-Mullerad, H., et al., "Sol-Gel Materials as Efficient Enzyme Protectors: Preserving the Activity of Phosphatases Under Extreme pH Conditions," Journal of the American Chemical Society, 2005, pp. 8077-8081, vol. 127, No. 22.
Gill, I., "Bio-Doped Nanocomposite Polymers: Sol-Gel Bioencapsulates," Chemistry of Materials, 2001, pp. 3404-3421, vol. 13, No. 10.
Gill, I., et al., "Encapsulation of Biologicals Within Silicate, Siloxane, and Hybrid Sol-Gel Polymers: An Efficient and Generic Approach," Journal of the American Chemical Society, 1998, pp. 8587-8598, vol. 120, No. 34.
Reetz, M. T., et al., "In situ Fixation of Lipase-Containing Hydrophobic Sol-Gel Materials on Sintered Glass-Highly Efficient Heterogeneous Biocatalysts," Chemical Communications, 1996, pp. 1397-1398.
Sakai-Kato, K., et al., "Integration of Biomolecules into Analytical Systems by Means of Silica Sol-Gel Technology," Analytical Sciences, Aug. 2009, pp. 969-978, vol. 25.

(Continued)

*Primary Examiner* — Lisa J Hobbs
(74) *Attorney, Agent, or Firm* — Senniger Powers LLP

(57) ABSTRACT

The present invention generally relates to improvements in enzyme immobilization, particularly for use in the field of carbon dioxide capture and sequestering. It has been discovered that the utilization of sol-gel processes to immobilize enzymes in polysilicate-polysilicone copolymer coatings and particles, and the deposition of these coatings on solid state supports or use of suspensions of these particles, provides significant benefits for use in industrial applications involving enzymatic catalysts.

25 Claims, 21 Drawing Sheets

(56) References Cited

OTHER PUBLICATIONS

International Search Report for PCT/US2013/032261, dated Jul. 25, 2013, 5 pages.

Alper, E., "Comments on the Effect of Carbonic Anhydrase on Carbon Dioxide Absorption," Chemical Engineering Science, Shorter Communications, 1978, pp. 1399-1400, vol. 33.

Alper, E., et al., "Comments on 'Gas Absorption with Catalytic Reaction'," Chemical Engineering Science, Shorter Communications, 1981, pp. 1097-1099, vol. 36.

Alper, E., et al., "Gas Absorption Mechanism in Catalytic Slurry Reactors," Chemical Engineering Science, 1980, pp. 217-222, vol. 35.

Alper, E., et al., "On the Mechanism of Enzyme-Catalysed Gas-Liquid Reactions: Absorption of CO2 Into Buffer Solutions Containing Carbonic Anhydrase," Chemical Engineering Science, 1980, pp. 2147-2156, vol. 35.

Crumbliss, A. L., et al., "Preparation and Activity of Carbonic Anhydrase Immobilized on Porous Silica Beads and Graphite Rods," Biotechnology and Bioengineering, 1988, pp. 796-801, vol. 31, No. 8.

* cited by examiner

Xerogel agglomerates 10 kV 4500x mag

Xerogel agglomerates 10 kV 14000x mag

Xerogel agglomerates 10 kV 6000x mag

Xerogel agglomerates 10 kV 6000x mag

FIG. 9
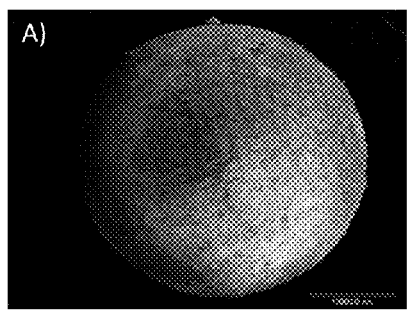
Sol-Gel Ceramic 5kV 25x mag.
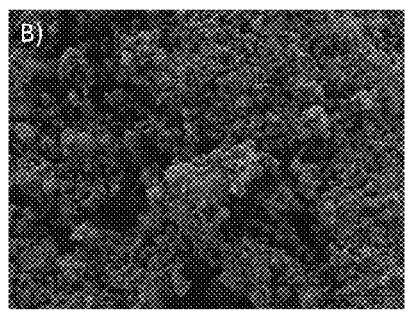
Sol-Gel Ceramic 5kV 1000x mag.
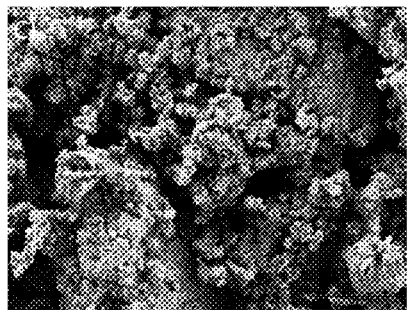
Sol-Gel Ceramic 5kV 2500x mag.
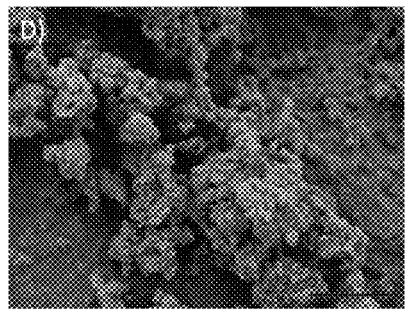
Sol-Gel Ceramic 5kV 5000x mag.

POLYSILICATE-POLYSILICONE ENZYME IMMOBILIZATION MATERIALS

FIELD OF THE INVENTION

The present invention generally relates to enzyme immobilization materials comprising a polysilicate-polysilicone copolymer. Particularly, the invention relates to polysilicate-polysilicone copolymeric immobilization materials for immobilizing carbonic anhydrase. The immobilized carbonic anhydrases can be used for carbon dioxide capture.

BACKGROUND OF THE INVENTION

Technologies are being developed for capturing carbon dioxide ($CO_2$) from industrial gas streams to reduce energy costs and the environmental impact of $CO_2$ in the atmosphere. Major sources of $CO_2$ emissions include power plants, cement kilns, natural gas processing facilities, ammonia plants, and hydrogen plants. The captured $CO_2$ can be sequestered or can be reutilized for: enhanced oil recovery, food processing or accelerated algae growth that could have multiple applications. In the cases of natural gas processing and ammonia production, removal of $CO_2$ is necessary step to meet product specifications. In the case of industrial hydrogen production, $CO_2$ removal can improve plant efficiency and increase product output.

Currently several alternate $CO_2$ capture technologies are in various stages of commercial practice and development. These include chemical absorption using amine solvents (particularly monoethanolamine—MEA), physical adsorption, membrane separation, cryogenic distillation, and mineral carbonation Chemical absorption with amines is currently considered the lowest cost method of $CO_2$ removal for the majority of gas streams, particularly for the clean-up of low levels of $CO_2$ in natural gas. MEA systems are more reactive, and therefore preferred, but the energy requirements to remove the absorbed $CO_2$ from the MEA is very high, at about 4 million BTU/tonne of $CO_2$ and can require up to about one-third of a power plant's boiler output.

One emerging alternative to amine stripping is to incorporate biocatalysts that are specific for carbon dioxide conversion ($CO_2$) in the presence of low duty solvents, subsequently lowering the regeneration energy requirements and lowering overall cost. Carbonic anhydrases (CAs), EC 4.2.1.1, are a family of enzymes that are ubiquitous in nature and are known to reversibly convert bicarbonate into $CO_2$ and water catalytically.

There is a need in the art for improved materials, compositions, methods, processes, and systems which improve the stability and efficiency of enzymes for use in the catalysis of industrial processes.

SUMMARY OF THE INVENTION

Among the various aspects of the invention is the immobilization of enzymes by entrapment in materials comprising a polysilicate-polysilicone copolymer.

Among the various aspects of the invention are porous particulates composed of immobilized enzymes in a polysilicate-polysilicone copolymer.

Among the various aspects of the invention is the development of porous particulates comprising a polysilicate-polysilicone copolymer and a biocatalyst that hydrates carbon dioxide. The particulates are generated in solution and typically contain a hydrophilic additive. The biocatalyst is entrapped in the particle composition.

Among the various aspects of the invention is a coated support containing enzyme immobilized in a coating material comprising a polysilicate-polysilicone copolymer.

Among the various aspects of the invention is a coated support comprising a solid support, a coating composition, and a biocatalyst that hydrates carbon dioxide. The coating composition forms a layer on the surface of the solid support and comprises a polysilicate-polysilicone copolymer and typically a hydrophilic additive. The biocatalyst is entrapped in the coating composition.

Among the various aspects of the invention is the use of common commercial polymer adhesives such as epoxies, urethanes, resins, cyanoacrylates, and methacrylates to adhere porous polysilicate-polysilicone copolymer particulates to solid supports.

In another aspect of the invention, the composition of coatings and particulates are derived from the reaction of a sol and a catalyst, wherein the sol comprises an alkoxy silane or an organotrialkoxy silane, a poly(silicone), a hydrophilic additive, and a biocatalyst that hydrates carbon dioxide.

A further aspect is directed to a process for removing $CO_2$ from a $CO_2$-containing gas, the process comprising contacting a liquid containing a suspension of immobilized enzymes or immobilized enzyme particles that catalyze the hydration of $CO_2$ with a $CO_2$-containing gas over a commercial contactor to promote diffusion of the $CO_2$ into the liquid, subsequent conversion of $CO_2$ to hydrogen ions and bicarbonate ions.

Another aspect is directed to a process for removing $CO_2$ from a $CO_2$-containing gas, the process comprising contacting a liquid with a $CO_2$-containing gas to promote diffusion of the $CO_2$ into the liquid, and contacting the $CO_2$ in the liquid with a coated support described herein to catalyze hydration of the $CO_2$ and form a treated liquid comprising hydrogen ions and bicarbonate ions.

Another aspect of the invention is directed to an immobilized enzyme comprising an enzyme and an immobilization material, wherein the enzyme is entrapped within the immobilization material and the immobilization material is derived from reaction of a sol and a catalyst, the sol comprising an alkoxy silane or an organotrialkoxy silane, or metasilicate, (a poly(silicone)), and an enzyme.

Yet another aspect is directed to a method for preparing porous particles described herein, comprising mixing an alkoxy silane or metasilicate and/or an organotrialkoxy silane, a poly(silicone), a hydrophilic additive, a carbonic anhydrase, catalyst, and a solvent to form porous particles containing entrapped enzyme.

Yet another aspect is directed to a method for preparing a coated support described herein, comprising mixing an alkoxy silane and/or an organotrialkoxy silane, a poly(silicone), a hydrophilic additive, a carbonic anhydrase, and a solvent to form a sol, contacting the sol with a catalyst to form a gel, and contacting a solid support with the gel.

An additional aspect is directed to a coated support comprising a solid support, and a coating composition forming a layer on the surface of the solid support, wherein the coating composition comprises an immobilized enzyme described herein.

Other objects and features will be in part apparent and in part pointed out hereinafter.

BRIEF DESCRIPTION OF THE DRAWINGS

FIGS. 9A-D are scanning electron micrographs of a polysilicate-polysilicone copolymeric coating on a ceramic spheres at 25×, 1000×, 2500×, and 5000× magnification, respectively.

Corresponding reference characters indicate corresponding parts throughout the drawings.

DESCRIPTION OF THE INVENTION

Figure 1A:
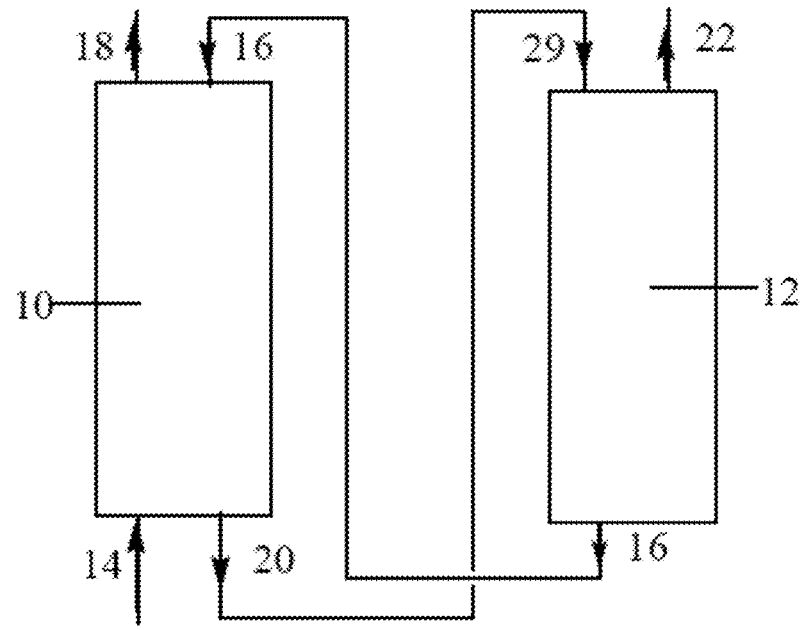
FIGS. 1A and 1B are schematics of a $CO_2$ absorber coupled with a $CO_2$ stripper and FIG. 1C is a schematic of a semi-batch reactor.

It has been discovered that the utilization of sol-gel processes to immobilize enzymes in polysilicate/polysiloxane derived materials results in functional materials that demonstrate excellent ability to convert $CO_2$ in water to bicarbonate and a proton. These materials can be deposited as coatings on solid state supports or used as particles in suspension. These materials provide significant benefits for use in industrial applications involving enzymatic catalysts.

The polysilicate-polysilicone copolymeric materials described herein provide a versatile platform for the immobilization of enzymes. This versatility is due, in part, from the high degree to which the properties of the particles and coatings can be modified based on selection of the component substituents. For example, the pore size, hydrophilicity/hydrophobicity, transport properties, and enzymatic functionality of the coating can be controlled by the appropriate selection of the component substituents.

The polysilicate-polysilicone copolymer coatings described herein can be applied to solid supports. Advantageously, the polysilicate-polysilicone copolymer coatings can be applied to commercially available packing materials suitable for use in various reactors, including packed bed reactors.

A coated support can comprise a polysilicate-polysilicone copolymer immobilizing a biocatalyst, the polysilicate-polysilicone copolymer adhered to a solid support by an adhesive coating.

These materials can also be used to coat solid particles that could be used in packed bed or fluidized bed reactors.

Alternatively, these processes described herein can also be used to generate particles of uniform or distributed particle sizes, commonly referred to as xerogels, which can be used in fluidized bed reactors or column contactors.

The resulting polysilicate/polysiloxane copolymer derived xerogels are porous particulates that display a range of particle sizes, and similar to coatings allowed for high retention of the immobilized enzyme and its catalytic activity.

The particle size, pore size, as well as the chemical and physical nature of the properties, can be controlled through synthetic methods.

The materials described herein can be polysilicate/polysiloxane copolymers as described in more detail below.

For example, packing materials coated with an immobilized enzyme prepared according to the methods described herein greatly increase the rate of conversion of carbon dioxide to bicarbonate as compared to bare ceramic and stainless steel packing materials. For example, high rates of sustained $CO_2$ conversion have been achieved in a continuous flow reactor for greater than 200 days at 45° C.

Likewise, a sample has been generated and tested for over one year that still retains catalytic activity over blank solvent.

The coated supports, methods, and systems described herein are particularly useful for the capture and sequestration of carbon dioxide in a liquid environment.

Further, the coated supports, methods, and systems described herein can specifically be used for capture and sequestration of carbon dioxide in an aqueous environment.

Coated Supports

The coated supports described herein comprise a solid support, a coating composition forming a layer on the surface of the solid support, the coating composition comprising a polysilicate-polysilicone copolymer and in some cases hydrophilic additives and/or surfactants; and a biocatalyst that catalyzes hydration of carbon dioxide entrapped in the coating composition. They are suitable for use in bio-industrial processes.

Since the biocatalyst catalyzes hydration of carbon dioxide, the coated supports are particularly useful in processes for the capture and sequestration of carbon dioxide. Particularly, the biocatalyst that catalyzes hydration of carbon dioxide comprises a carbonic anhydrase.

Generally, the coated supports comprise an enzyme immobilized within a coating composition, wherein the coating composition forms one or more layers over the surface of the solid support.

The coating composition can be prepared using a sol-gel process, wherein a sol and a catalyst react in the presence of an enzyme. The resulting coating comprises a polysilicate-polysilicone copolymer, wherein the enzyme is immobilized in the pores of the polysilicate-polysilicone copolymer structure.

Solid Support

The size, shape, and surface characteristics of the solid support can be varied depending upon the particular application. In many cases, it is desirable for the solid support to possess relatively high surface area, to maximize the space available for contact with the coating. Depending on the particular application, preferred materials should be thermally and chemically stable for use at pHs of 7 to 11 and temperatures of 40° C. to 130° C. The preferred operating temperature range is typically 40° C. to 60° C. Stainless steel, polymers, and ceramic materials, for example, have thermal and chemical characteristics that are advantageous for many applications.

The solid support can be a commercially available random or structured packing material. Examples of commercially available random packing materials include Berl saddle, Intalox saddle, Raschig ring or Pall ring packings The random packing materials may comprise various materials, including, for example, ceramic, plastic, stainless steel, and combinations thereof. Examples of commercially available structured packing materials include ceramic monoliths, as well as structured steel and plastic packing materials. These packing materials are particularly suitable for use in a packed-bed reactor.

The commercially available packing materials are useful because they typically have high surface area to volume ratios and the immobilization materials are able to adhere to the surface of the packing materials and thus, can be efficient for industrial applications.

The commercial packing materials when coated as described herein are particularly useful in an industrial environment where carbon dioxide is captured from a gas phase.

The surface of the solid support can be treated prior to coating to provide desirable properties. For example, the surface of ceramic solid supports is typically etched to increase available surface area and the number of reactive functional groups. Stainless steel supports can undergo descaling or chemical oxidation for similar purposes.

The surface of the solid support can pretreated with a primer layer to provide reactive moieties at the surface of the support prior to application of the coating. This can provide improved adhesion between the support and the coating. Typically, the primer coating comprises organic and/or inorganic polymers that contain pendant hydroxyl or silanol functionalities.

Coating

Because the coating is used to immobilize an enzyme, it is sometimes referred to herein as an immobilization material. These coatings or immobilization materials described herein are polysilicate-polysilicone copolymers.

The polysilicate-polysilicone copolymer coatings described herein provide a versatile platform for the immobilization of enzymes. This versatility is due, in part, to the high degree to which the properties of the coating can be modified based on selection of the component substituents. For example, the pore size, hydrophilicity/hydrophobicity, and enzymatic functionality of the coating can be controlled by the appropriate selection of the component substituents.

The porous nature of the coating, which can be broadly distributed between micro and macroporous, facilitates transport of reactants and products into and out of the polymeric structure. As a result, the three dimensional matrix is able to effectively retain the enzyme within the coating without overly restricting its activity.

Xerogel Particles

The xerogel particles described herein comprise a polysilicate-polysilicone copolymer, a hydrophilic additive and a biocatalyst entrapped in the particle composition that catalyzes hydration of carbon dioxide. Suspensions of the resulting materials are suitable for use in bio-industrial processes.

The resulting particles can be synthesized in a single pot using aqueous or alcohol diluents.

The particles typically range in size from hundreds of nanometers to hundreds of micrometers. Typically, the particles used in the suspension application described here in ranged in size from 25 to 50 μm, 50 to 75 μm, or 100 to 250 μm.

As with the coatings described above, the choice of synthetic methods and reactive components can be used to control particle size and the underlying properties of the matrix including particle size, pore size, and hydrophobicity.

Typically, an optimized xerogel particle consists of 2 to 10% immobilized enzyme by weight. However, the weight percent enzyme can readily be controlled by adjusting the amount of enzyme added into the synthetic mixture.

The porous nature of the particles, which again can be broadly distributed between micro and macroporous, serves to facilitate transport of reactants and products into and out of the polymeric structure; this porosity of the particles reduces mass transfer limitations. As a result, the three dimensional matrix effectively retains the enzyme within the coating without significantly decreasing the enzyme's activity.

Typically, greater than 80% enzyme retention is observed over the course of days, weeks, and months, in carbonate buffer at a pH of about 10 at room temperature.

The enzymatic activity of these particles has been demonstrated in a batch reactor vessel and in a counter-current flow column.

In batch reactor studies, suspensions containing 0.2 wt. % particulates in 2.0 M potassium carbonate/bicarbonate, pH 10.0 have shown mass transfer coefficients ($K_G$) as high as 0.16 mmol/s·m²·kPa.

In batch reactor studies, carbonic anhydrase immobilized in polysilicate/polysiloxane particles have shown enhanced performance over solubilized enzyme at similar loading levels.

This aforementioned enhancement phenomenon has been attributed to the low density (i.e., high void volume) of the particles and their subsequent concentration at the surface of the reaction solution. This surface concentration of the immobilized enzyme particles reduces the contribution of mass transfer from the gas to liquid phase.

In addition to batch reactor systems, larger volumes of suspensions have been prepared and analyzed in flow-through reactors containing both random and structured packing as contactor materials. Catalytic improvements in a well dispersed flow-through suspension system as high as six fold have been observed in a packed bed reactor system.

Attaching Xerogel Particles to Solid Supports Using Polymer Adhesives

As an alternative method for utilizing the xerogel particles described above, polymer adhesives can be used to adhere the enzyme containing powders to the surface of solid supports.

Typical polymer adhesives that can be utilized in this method are epoxies, urethanes, resins, cyanoacrylates, and methacrylates. Typically, epoxies and urethanes are preferred.

The solid support can be treated with a polymer adhesive diluted in a solvent appropriate for the polymer adhesive selected by dipping the solid support into the polymer adhesive. Before the polymer adhesive is completely cured, the polymer adhesive layer is contacted with polysilicate-polysilicone copolymer powder particles comprising an enzyme. The resulting coated solid support is dried at room temperature for 3 hours and then thermally cured at from 55° C. to 90° C. for 24 to 96 hours.

Usually, the solid support is treated with a two-part epoxy or urethane polymer adhesive by dipping the solid support in the incompletely cured polymer adhesive and then contacting the solid support coated with the polymer adhesive with polysilicate-polysilicone copolymer powder particles comprising an enzyme. Again, the resulting coated solid support is dried at room temperature for 3 hours and then thermally cured at from 55° C. to 100° C. for 24 to 96 hours.

The result is structured packing coated with adhered polysilicate-polysilicone copolymer immobilized enzyme particles.

Further, the method for preparing the coated support can comprise mixing (i) an alkoxy silane or an organotrialkoxy silane or metasilicate, (ii) a poly(silicone), (iii) a hydrophilic additive, (iv) a carbonic anhydrase, and (v) solvent to form a sol; contacting the sol with a catalyst to form a gel; drying the gel and forming xerogel particles; contacting a solid support with the adhesive coating; and contacting the solid support having the adhesive coating with the xerogel particles to form the coated support.

Structured packing materials coated with this method have shown mass transfer coefficients ($K_G$) as high as 0.12 mmol/s·m²·kPa.

Polysilicate-Polysilicone Copolymer

The composition of the coatings and particles described herein comprise a polysilicate-polysilicone copolymer, which is typically derived from an alkoxy silane or an organotrialkoxy silane and a poly(silicone). Since silicates and silicones can be designed to readily form three-dimensional polymer networks in solution, they are useful in forming polymers for the entrapment of enzymes.

The polysilicate-polysilicone copolymer can be derived from reaction of a sol and a catalyst, the sol comprising (i) an alkoxy silane or an organotrialkoxy silane, (ii) a poly(silicone), (iii) a hydrophilic additive, and (iv) a biocatalyst that catalyzes hydration of carbon dioxide. The sol can optionally further comprise a surfactant.

As described in more detail below, the biocatalyst that catalyzes hydration of carbon dioxide can be a carbonic anhydrase.

The alkoxy silane can have a structure of Formula 1

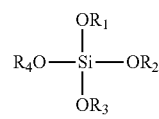

(1)

wherein $R_1$, $R_2$, $R_3$, and $R_4$ are independently hydrogen or $C_1$-$C_4$ alkyl; preferably $R_1$, $R_2$, $R_3$, and $R_4$ are independently methyl or ethyl.

Alkoxy silanes typically include tetramethylorthosilicate, tetraethylorthosilicate, methyltriethylorthosilicate, ethyltrimethylorthosilicate, dimethyldiethylorthosilicate, tetraglyceryl silicate, sodium metasilicate or a combination thereof. Tetramethylorthosilicate and tetraethylorthosilicate are especially preferred.

The organotrialkoxy silane has a structure of Formula 2

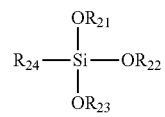

(2)

wherein $R_{21}$, $R_{22}$, $R_{23}$, and $R_{24}$ are independently hydrogen or $C_1$-$C_4$ alkyl; preferably $R_{21}$, $R_{22}$, $R_{23}$, and $R_{24}$ are independently methyl or ethyl.

The organotrialkoxy silane is typically trimethoxymethylsilane, trimethoxyethylsilane, or a combination thereof.

Hydrophilic organotrialkoxy silanes can also be utilized to improve wetting and aqueous transport. Preferred versions include 2[(Methoxy(polyethyleneoxy)propyl]trimethoxy silane.

The poly(silicone) is typically selected from the group consisting of poly(siloxanes), poly(glyceryl silicates), and polysilsesquioxanes.

Preferably, the poly(silicone) species is typically silanol or alkoxy silane terminated.

Poly(siloxanes) are a preferred type of poly(silicone). Generally, poly(siloxanes) have a structure of Formula 3

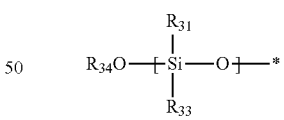

(3)

wherein $R_{31}$, $R_{32}$, $R_{33}$, and $R_{34}$ are independently hydrogen or $C_1$-$C_4$ alkyl; preferably $R_{31}$, $R_{32}$, $R_{33}$, and $R_{34}$ are independently methyl or ethyl.

Poly(siloxanes) typically include poly(dimethylsiloxane), poly(dimethylsiloxane)-co-poly(alkene oxide), poly(dimethylsiloxane)-g-poly(ethylene oxide), and block copolymers of poly(dimethylsiloxane) and poly(ethylene oxide), or combinations thereof. Preferably, the poly(siloxane) is silanol terminated. Silanol terminated poly(dimethylsiloxane) is a preferred poly(siloxane).

The silanol terminated poly(dimethylsiloxane) can have an average molecular weight of about 200 daltons, about 550 daltons, about 1100 daltons, about 2750 daltons, or about 4200 daltons. The average molecular weight can range from about 200 daltons to about 2750 daltons, from about 200 daltons to about 1100 daltons, or from about 450 daltons to about 650 daltons.

The ratio of alkoxy silane or organotrialkoxy silane to poly(silicone) is one parameter that affects the enzyme activity. For example, increasing the amount of a poly(silicone) in the sol solution relative to the alkoxy silanes or organotrialkoxy silanes typically increases pore size and volume. Coatings with appropriately controlled porosity are more permeable to the reactant stream and, subsequently, allow for a higher level of retained enzyme activity.

Further, for use in a carbon capture system, hydrophobic components, such as alkyl silanes (e.g., trimethoxymethylsilane, trimethoxy(propyl)silane, trimethoxy(butyl)silane, and trimethoxy(octyl)silane) can be used, but in amounts that provide a polysilicate-polysilicone copolymer that has acceptable hydrophobicity.

In some cases, hydrophobicity of the polysilicate-polysilicone copolymer coating or immobilization material can prevent aqueous solutions of reactants (e.g., carbon dioxide) from making contact with the enzyme, resulting in significantly reduced enzyme activity. Sometimes when the hydrophobicity is too high, the flux of reactants through the coating or immobilization material, especially when the coated supports are utilized in aqueous environments, can be too low for the most efficient reaction.

Where a mixture of alkoxy silanes and poly(silicones) is used, the molar ratio of alkoxy silane to poly(silicone) is typically about 1:1, about 2:1, about 3:1, about 4:1, about 5:1, about 6:1, about 7:1, about 8:1, about 10:1, about 12:1, about 15:1, or about 20:1. The molar ratio can range from about 1:1 to about 20:1, from about 2:1 to about 8:1, or from about 3:1 to about 5:1.

Further, where a mixture of alkoxy silanes and poly(siloxanes) is used, the molar ratio of alkoxy silane to poly(siloxane) is typically about 1:1, about 2:1, about 3:1, about 4:1, about 5:1, about 6:1, about 7:1, about 8:1, about 10:1, about 12:1, about 15:1, or about 20:1. The molar ratio can range from about 1:1 to about 20:1, from about 2:1 to about 8:1, or from about 3:1 to about 5:1.

Hydrophilic Additives

The sol used to prepare the coatings and particles can also contain a hydrophilic additive.

If prepared in the absence of hydrophilic additives, the polysilicate-polysilicone copolymer coatings described herein are more hydrophobic. This is acceptable for some applications, particularly for applications in non-aqueous environments. In other applications, however, a high degree of hydrophobicity can result in significantly reduced enzyme activity. It is therefore desirable to incorporate a hydrophilic additive into the coating composition, particularly where the enzyme is used to catalyze hydrophilic reactants in an aqueous environment.

Examples of typical hydrophilic additives include poly (vinyl alcohol), poly(ethylene oxide), a quaternary ammonium polymer, a crown ether, a cyclodextrin, a surfactant, poly(1-methyl-4-vinylpyridinium bromide), poly(acrylamide-methacryloxyethyltrimethylammonium bromide, and combinations thereof.

Suitable quaternary ammonium polymers can include, for example, poly(diallyldimethylammonium chloride), poly(1-methyl-4-vinylpyridinium bromide), poly(acrylamide-methacryloxyethyltrimethylammonium bromide), or a combination thereof. Preferably, the quaternary ammonium polymer comprises poly(diallyldimethylammonium chloride).

Cyclodextrin additives can include, for example, α-cyclodextrin, β-cyclodextrin, γ-cyclodextrin, and combinations thereof β-Cyclodextrin is preferred.

Crown ethers are a preferred class of hydrophilic additives. Suitable crown ethers include 12-crown-4, 1,7-diaza-12-crown-4, 1,4,8,11-tetrathiacyclotetradecane, 1,4,8,12-tetraazacyclopentadecane, 15-crown-5, 18-crown-6, dibenzo-18-crown-6, dicyclohexano-18-crown-6, (18-crown-6)-2,3,11,12-tetracarboxylic acid, 1-aza-18-crown-6, diaza-18-crown-6, and combinations thereof. A crown ether comprising 18-crown-6 is especially preferred.

Preferably, the coatings and particles are derived from a sol comprising tetramethylorthosilicate, polydimethylsiloxane, a crown ether, and a carbonic anhydrase.

Surfactants

The sol used to prepare the coatings and particles can also contain a surfactant.

The surfactant can act as a flow agent in coating and particle preparation. Further it can be used to control the resulting properties of the coatings and particles; including particles size, pore structure and size, and wettability.

Surfactants suitable for use as additives include N,N-bis(3-D-gluconamidopropyl)cholamide (BigCHAP), N,N-bis(3-D-gluconamidopropyl)deoxycholamide (DeoxylBigCHAP), a polyoxyethylene alcohol (BRIJ 35 and BRIJ 58 P), 2-cyclohexylmethyl-β-D-maltoside (CYMAL-1), 2-cyclohexylethyl-β-D-maltoside (CYMAL-2), cyclohexylpentyl-β-D-maltoside (CYMAL-5), cyclohexylhexyl-β-D-maltoside (CYMAL-6), decyl-β-D-maltopyranoside, n-dodecyl-β-D-maltoside, n-hexadecyl-β-D-maltoside, undecyl-β-D-maltoside, decyl-β-D-1-thiomaltopyranoside, octyl-β-D-thioglucopyranoside, digitonin, dimethydecylphosphine oxide, dodecyldimethylphosphine oxide, (octylphenoxy)polyethoxyethanol (IGEPAL® CA630), N-octanoyl-N-methylglucamine (MEGA-8), N-nonanoyl-N-methylglucamine (MEGA-9), N-decanoyl-N-methylglucamine (MEGA-10), a polyoxy ethylene octyl phenol (NONIDET® P40-substitute), a polyoxyethylene-polyoxypropylene block co-polymer (PLURONIC® F-68), poly(ethylene glycol)-block-poly(propylene glycol)-block-poly(ethylene glycol) (PLURONIC® P-123) saponin, polyoxyethylene 9-lauryl ether (THESIT®), a polyoxy ethylene octyl phenol (e.g., TRITON® X-100 and TRITON® X-114), a polyoxyethylene derivative of sorbitan monolaurate (e.g., TWEEN® 20, TWEEN® 40, and TWEEN® 80), N,N-dimethyldodecylamine-N-oxide, hexadecyltrimethylammonium bromide (CTAB), an alcohol ethoxylate (SYNPERONIC® A7), and combinations thereof.

A preferred surfactant species is hexadecyltrimethylammonium bromide. Polyoxyethylene derivatives of sorbitan monolaurate are also preferred.

Coated Supports Derived from Sol-Gel Reaction

The coating can be derived from the reaction of a sol and a catalyst. Typically, the sol comprises a poly(silicone), and an alkoxy silane and/or an organotrialkoxy silane, and an enzyme dispersed throughout an aqueous medium. A catalyst is introduced to assist with a polymerization reaction, wherein the alkoxy silane, and/or organotrialkoxy silane, and poly(silicone) undergo hydrolysis and subsequent condensation, thereby incorporating the enzyme into a gel-like material. The gel is coated onto a solid support, which then undergoes thermal curing. The result is a three-dimensional network polymer, wherein the enzyme molecules are immobilized in the pores of the polymeric structure.

Coatings produced according to this process typically have advantageous properties. For example, the polymeric structure can act to stabilize the enzyme against thermal and chemical damage, while possessing pore sizes sufficient for the immobilized enzyme to retain a significant portion of its catalytic activity.

The catalyst can comprise ammonium fluoride, sodium fluoride, tetrabutylammonium fluoride, ammonium hydroxide, sodium hydroxide, potassium hydroxide, sodium hydroxide, or a combination thereof. A catalyst comprising ammonium fluoride is preferred.

More generally, the catalyst may comprise an acid or a base, including Lewis acids and Lewis basis. The catalyst may be used to initiate acid- or base-induced hydrolysis or condensation.

Multiple Coating Layers

The solid support can also be coated with two or more layers of the coating. Additional layers serve to increase the overall thickness of the coating, and thereby increase the amount of enzyme that can be loaded onto the solid support. If two or more layers are present, it is preferred that each layer comprise entrapped enzymes.

Physical Properties of the Coating

Typically, the coating has a surface area of at least about 1 $m^2/g$, at least 10 $m^2/g$, at least about 20 $m^2/g$, at least about 30 $m^2/g$, at least about 40 $m^2/g$, at least about 50 $m^2/g$, at least about 60 $m^2/g$, at least about 70 $m^2/g$, at least about 80 $m^2/g$, at least about 90 $m^2/g$, at least about 100 $m^2/g$, at least about 150 $m^2/g$, at least about 200 $m^2/g$, or at least about 300 $m^2/g$.

The surface area of the coating typically ranges from about 1 $m^2/g$ to about 400 $m^2/g$, from about 5 $m^2/g$ to about 300 $m^2/g$, from about 10 to about 150 $m^2/g$, or from about 15 to about 100 $m^2/g$.

The coating typically has a pore diameter of from about 1 nm to about 200 nm, more preferably from about 2 nm to about 80 nm, more preferably from about 20 nm to about 80 nm.

The coating typically has an overall pore volume of at least about 3 µL/g to 500 µL/g. Typically, at least about 20%, at least about 30%, at least about 40%, at least about 50%, at least about 60%, at least about 70%, or at least about 80% of the overall pore volume may be attributed to pores having a pore diameter of between about 20 nm and about 80 nm.

The polysilicate-polysilicone copolymer can be used as an immobilization material. In this instance, the immobilized enzyme comprises an enzyme and an immobilization material. The enzyme is entrapped within the immobilization material and the immobilization material is derived from reaction of a sol and a catalyst, the sol comprising (i) an alkoxy silane or an organotrialkoxy silane, (ii) a poly(silicone), and (iii) an enzyme. The sol, alkoxy silane or an organotrialkoxy silane, and poly(silicone) are described herein above.

Further, the enzyme is entrapped within the immobilization material and the immobilization material is derived from reaction of a sol and a catalyst, the sol comprising (i) an alkoxy silane or an organotrialkoxy silane, (ii) a poly(siloxane), and (iii) an enzyme. The sol, alkoxy silane or an organotrialkoxy silane, and poly(siloxane) are described herein above.

Biocatalyst and Enzyme

The coating also includes a catalyst that catalyzes hydration of carbon dioxide. Typically, the catalyst can be a biocatalyst such as an enzyme, a ribozyme, a deoxyribozyme, an enzyme mimic, or an organic or inorganic compound that can catalyze hydration of carbon dioxide.

Preferably, the biocatalyst is a carbonic anhydrase. Without being bound by theory, it is believed that a carbonic anhydrase enzyme catalyzes hydration of carbon dioxide by having a zinc atom in the active site that coordinates to three histidine side chains while having the fourth coordination position of the zinc atom occupied by water. The coordination of the water by the zinc atom causes polarization of the hydrogen-oxygen bond. A fourth histidine accepts a proton from the coordinated water molecule resulting in a hydroxide attached to the zinc atom. The carbonic anhydrase active site also contains a pocket for carbon dioxide that brings it close to the hydroxide group and allowing the electron-rich hydroxide to attack the carbon dioxide to form bicarbonate. In this way, the carbonic anhydrase is involved in the hydration of carbon dioxide. (Tripp, B. C., Smith, K., & Ferry, J. G. (2001). Carbonic Anhydrase: New Insights for an Ancient Enzyme. *Journal of Biological Chemistry*, 276 (52), 48615-48618.)

Typically, the enzyme is entrapped within the pores of the three-dimensional polysilicate-polysilicone copolymer network.

When the coating or immobilized enzyme contains an enzyme, naturally-occurring enzymes, man-made enzymes, artificial enzymes and modified naturally-occurring enzymes can be utilized. In addition, engineered enzymes that have been engineered by natural or directed evolution can be used. Also, an organic or inorganic molecules that mimics an enzyme's properties can be used.

The enzyme can comprise a lipase, a glucose isomerase, a nitrilase, a glucose oxidase, a protease, a carbonic anhydrase, a pepsin, an amylase, a fungal amylase, a maltogenic amylase, a cellulase, a lactase, an esterase, a carbohydrase, a hemicellulase, a pentosanase, a xylanase, a pullulanase, a β-glucanase, an acetolactate decarboxylase, β-glucosidase, a glutaminase, a penicillin acylase, a chloroperoxidase, an aspartic β-decarboxylase, a cyclodextrin glycosyltransferase, a subtilisin, an aminoacylase, an alcohol dehydrogenase, an amino acid oxidase, a phospholipase, a urease, a cholesterase, a desulfinase, a lignin peroxidase, a pectinase, an oxidoreductase, a dextranase, a glucosidase, a galactosidase, a glucoamylase, a maltase, a sucrase, an invertase, a naringanase, a bromelain, a ficin, a papain, a pepsin, a peptidase, a chymosin, a thermolysin, a trypsin, a triglyceridase, a pregastric esterase, a phosphatase, a phytase, an amidase, a glutaminase, a lysozyme, a catalase, a dehydrogenase, a peroxidase, a lyase, a fumarase, a histadase, an aminotransferase, a ligase, a cyclase, a racemase, a mutase, an oxidase, a reductase, a ligninase, a laccase, a chloroperoxidase, a haloperoxidase, a hydrogenase, a nitrogenase, an oxynitrilase, or combinations thereof.

Preferably, the biocatalyst that catalyzes hydration of carbon dioxide or the enzyme immobilized is a carbonic anhydrase. The carbonic anhydrase (CA) used in the systems described herein catalyzes the reversible conversion of carbon dioxide and water to bicarbonate and a proton. CA represents a family of structurally and genetically diverse enzymes that arose independently from different precursors as a result of convergent evolution (Tripp, B. C., Smith, K., & Ferry, J. G. (2001). Carbonic Anhydrase: New Insights for an Ancient Enzyme. *Journal of Biological Chemistry*, 276 (52), 48615-48618; Elluche, S., & Pöggeler, S. (2010). Carbonic Anhydrases in Fungi. *Microbiology*, 156, 23-29). The various CA enzymes have been organized into five unrelated structural classes (e.g., alpha, beta, gamma, delta, and epsilon) which share no DNA sequence similarity and differ in protein structure and active site architecture. Despite these structural differences, the active sites of all classes of CA enzymes function with a single divalent metal cofactor which is essential for catalysis (Tripp, B. C., Smith, K., & Ferry, J. G. (2001). Carbonic Anhydrase: New Insights for an Ancient Enzyme. *Journal of Biological Chemistry,* 276 (52), 48615-48618). The most common metal cofactor in CA enzymes is zinc.

The α-class of CA is the predominant form expressed in mammals, and is the best characterized of all the CA classes. There are at least 16 α-CA or CA-related enzymes (Supuran, C. T. (2008). Carbonic Anhydrases—An Overview. *Current Pharmaceutical Design,* 14, 603-614 found in animals, as well as 6 forms found in bacteria. The β-class of CAs are found in green plants, blue-green algae, and bacteria (Zimmerman, S. A., & Ferry, J. G. (2008). The β and γ Classes of Carbonic Anhydrases. *Current Pharmaceutical Design,* 14, 716-721) (Rowlett, R. S. (2010). Structure and Catalytic Mechanism of the β-Carbonic Anhydrases. *Biochimica et Biophysica Acta,* 1804, 362-373). The γ-class is found in bacteria and an example would be the CA from *Methanosarcina thermophile* (CAM) (Zimmerman, S. A., & Ferry, J. G. (2008). The β and γ Classes of Carbonic Anhydrases. *Current Pharmaceutical Design,* 14, 716-721). The CAM gene has been cloned into *E. coli* and is expressed as the Zn-containing form (Alber, B. E., & Ferry, J. G. (1996). Characterization of Heterologously Produced Carbonic Anhydrase from Methanosarcina thermophila. *Journal of Bacteriology* (June), 3270-3274), but it is more active as the Fe-, Cd-, or Co-form. The δ-class can be found in the marine diatom *Thalassiosira weissflogii* (Zimmerman, S. A., & Ferry, J. G. (2008). The β and γ Classes of Carbonic Anhydrases. *Current Pharmaceutical Design,* 14, 716-721). This example protein is a dimer, with a monomeric molecular weight of 27 kD. The protein will bind Zn-, but Fe- and/or Cd-predominates in vivo. Likewise, the ζ-class is also found in the marine diatom *Thalassiosira weissflogii* (Zimmerman, S. A., & Ferry, J. G. (2008). The β and γ Classes of Carbonic Anhydrases. *Current Pharmaceutical Design,* 14, 716-721). The protein is also a dimer with a molecular weight of 50-60 kD. The catalytic properties of these two classes have not been characterized.

The mammalian CA enzymes are divided into four broad subgroups depending on the tissue or cellular compartment location (e.g., cytosolic, mitochondrial, secreted, and membrane-associated). The CAII and CAIV enzymes are the most catalytically efficient of all the CAs characterized, demonstrating rates of catalysis that are near the theoretical limit for diffusion-controlled rates. CA IV demonstrates particularly high temperature stability, which is believed to result from the presence of two disulfide linkages in the enzyme.

Mammalian carbonic anhydrase, plant carbonic anhydrase, or microbial carbonic anhydrase; preferably, bovine carbonic anhydrase II or human carbonic anhydrase IV is used. Human carbonic anhydrase IV is available from William S. Sly at St. Louis University and is described in more detail in the following references: T. Okuyama, S Sato, X. L. Zhu, A. Waheed, and W. S. Sly, Human carbonic anhydrase IV: cDNA cloning, sequence comparison, and expression in COS cell membranes, *Proc. Natl. Acad. Sci. USA* 1992, 89(4), 1315-1319 and T. Stams, S. K. Nair, T. Okuyama, A. Waheed, W. S. Sly, D. W. Christianson, Crystal structure of the secretory form of membrane-associated human carbonic anhydrase IV at 2.8-Å resolution, *Proc. Natl. Acad. Sci. USA* 1996, 93, 13589-13594.

Compounds that mimic the active site of carbonic anhydrase can also be used. For example, various metal complexes have been used to mimic the carbonic anhydrase active site. For example, $[Zn_2(3,6,9,12,20,23,26,29\text{-octaazatricyclo}[29.3.1.1^{14,18}]\text{hexatriaconta-1}(34),14,16,18(36),31(35),32\text{-hexaene})(CO_3)]Br_2 \cdot 7H_2O$ and $[Zn_2(3,6,9,12,20,23,26,29\text{-octaazatricyclo}[29.3.1.1^{14,18}]\text{hexatriaconta-1}(34),14,16,18(36),31(35),32\text{-hexaene})(CO_3)]Br_2 \cdot 0.5CH_3COCH_3 \cdot 5H_2O$ (See Qi et al., Inorganic Chemistry Communications 2008, 11, 929-934). Also used as a mimic for carbonic anhydrase was $[\text{tris}(2\text{-benzimidazolylmethyl})\text{amineZn(OH)}_2]^{2+}$, $[\text{tris}(2\text{-benzimidazolyl})\text{amineZn(OH)}_2](ClO_4)_2$, and $[\text{tris}(\text{hydroxy-2-benzimidazolylmethyl})\text{amineZn(OH)}]$ $ClO_4 \cdot 1.5H_2O$ were also used to hydrate $CO_2$. (See Nakata et al., The Chemistry Letters, 1997, 991-992 and Echizen et al., Journal of Inorganic Biochemistry 2004, 98, 1347-1360).

Preferably, the enzyme is a carbonic anhydrase; more preferably, the carbonic anhydrase is an alpha-carbonic anhydrase, a beta-carbonic anhydrase, a gamma-carbonic anhydrase, a delta-carbonic anhydrase, or an epsilon-carbonic anhydrase. The carbonic anhydrase is an alpha-carbonic anhydrase and further is a cytosolic carbonic anhydrase, a mitochondrial carbonic anhydrase, a secreted carbonic anhydrase, or a membrane-associated carbonic anhydrase.

More preferably, the carbonic anhydrase is a mammalian carbonic anhydrase, a plant carbonic anhydrase, or a microbial carbonic anhydrase; most preferably, a microbial carbonic anhydrase.

Stabilization and Immobilization of the Enzyme

For purposes of the present invention, an enzyme is "stabilized" if the rate of activity loss is less than the rate of activity loss seen in a non-immobilized enzyme under the same conditions. The immobilization of the enzyme provides a significant advantage in stability. The enzyme activity can be measured by a means that demonstrate enzyme-mediated generation of product. The activity can be followed by chemiluminescence, electrochemical, mass spectrometry, spectrophotometric (i.e. UV-Vis), radiochemical, or fluorescence assays wherein the intensity of the property is measured at an initial time and then monitored for the duration of the experiment.

The enzyme can retain at least about 10%, 20%, 30%, 40%, 50%, or more of its initial activity while the enzyme is continuously catalyzing a chemical transformation.

With respect to the stabilization of the enzyme, the coatings and particles (i.e., enzyme immobilization material) provide a chemical and/or mechanical barrier to prevent or impede enzyme denaturation. To this end, it is believed that the enzyme immobilization material physically confines the enzyme, preventing the enzyme from unfolding. The process of unfolding an enzyme from a folded three-dimensional structure is one mechanism of enzyme denaturation.

An enzyme having greater temperature or pH stability can also retain at least about 75% of its initial catalytic activity for at least about 10 days when actively catalyzing a chemical transformation as described above.

The enzyme is immobilized by the immobilization material when at least 50%, 60%, 70%, 80%, or more of the enzyme is retained in the polysilicate-polysilicone copolymer particles for at least 5, 10, 20, 40, 60, 80, 100, 150, 200, 250, 300, 350, or more days. Further, the enzyme is retained by the immobilization material for from 5-365, 10-365, 20-365, 40-365, 60-365, 80-365, 100-365, 150-365, 200-365, 250-365, 300-365, or 350-365 days.

Methods of Preparation

Generally, the coating or immobilization material comprising an entrapped enzyme can be prepared using a sol-gel process technique. A "sol-gel" process is one in which a colloidal composition, or "sol," acts as the precursor for an integrated network, or "gel," of network polymers and/or discrete particles.

The sol comprises an alkoxy silane, and/or organotrialkoxy silane, and/or a metasilicate, a poly(silicone), and an enzyme dispersed in an aqueous medium. To produce the gel product, a polymerization reaction is initiated in which the alkoxy silane, and/or organotrialkoxy silane, and the poly(silicone) undergo a condensation reaction in the presence of the enzyme. A catalyst can be used to assist with the polymerization process.

The process results in the formation of a network polymer, wherein the enzyme molecules are immobilized in the pores of the polymeric structure. One of the advantageous properties of the gel product is that the immobilized enzyme retains the enzyme within the ports of the immobilization material.

Also, the immobilized enzyme can retain a significant portion of its catalytic activity as described in more detail in the Enzyme Stability section above.

The sol can also comprise a hydrophilic additive, which can be used to optimize the properties of the gel product. Exemplary hydrophilic additives are detailed above.

Solid Support

The size, shape, and surface characteristics of the solid support can be varied depending upon the particular application. Generally, preferred materials should be thermally and chemically stable enough to withstand potentially harsh process conditions. Stainless steel and ceramic materials, for example, have thermal and chemical characteristics that are advantageous for many applications. The types of solids supports and their physical and chemical properties are described above.

The solid support can optionally undergo an etching step before it is coated with the colloidal composition. One advantage of an etching step is that it serves to increase the surface area and number of functional groups on the support, which facilitates a more effective coating process.

Typically, the etching reagent comprises an acid. Hydrogen fluoride is a preferred acid, and is particularly preferred where the solid support comprises a ceramic material.

The etching reagent can comprise an oxidant. Preferred oxidants include hydrogen peroxide, ammonium hydroxide, and mixtures thereof. Mixtures of hydrogen peroxide and ammonium hydroxide typically have a mass ratio of from about 1:4 to about 4:1, more typically a ratio of about 1:1.

In some cases, the etching step will comprise contacting the solid support with a reducing agent followed by contacting the solid support with an oxidant.

In the case of stainless steel, treatments such as washing, polishing, descaling, and sand blasting can be used to pretreat the surface. Typical descaling solutions may comprise aqueous solutions of hydrofluoric and/or nitric acid.

The supports can also be pretreated with a primer coating layer. Typically, the primer coating comprises organic and/or inorganic polymers that contain pendant hydroxyl or silanol functionalities. Pretreatment with a primer coating layer increases the number functional moieties at the surface of the support. This can be used for adhesion between the support and the coating, which can provide an advantage over a standard bulk coating process.

Selection of the primer coating layer depends on the particular materials comprising the surface of the support. For example, both ceramic and stainless steel supports can be treated with tetramethoxysilane or tetraethoxysilane in the presence of an acid or base catalyst. The primer coating layer can then be thermally cured, resulting in a silicate coating with reactive silanol groups covering the surface of the support.

Where the coating layer is derived from the reaction of a sol and a catalyst, and the sol comprises an alkoxy silane or organotrialkoxy silane and a poly(silicone), exposure of functional moieties at the surface of the support can allow for attachment of the resulting polysilicate-polysilicone copolymer as a coating.

Components of the Colloidal Composition ("Sol")

The colloidal composition, or "sol," comprises an alkoxy silane and/or organotrialkoxy silane, a poly(silicone), and an enzyme.

The sol can also comprise a hydrophilic additive that can be used to optimize the properties of the gel product.

The sol can also comprise a surfactant that can be used to optimize the properties of the gel product.

The sol can also comprise an optional catalyst to assist with the polymerization process.

Biocatalyst and Enzyme

The sol comprises a biocatalyst that catalyzes hydration of carbon dioxide. The biocatalyst becomes entrapped within the pores of the three-dimensional polysilicate-polysilicone copolymer network that is formed in accordance with the sol-gel process described above. Typically, the biocatalyst is an enzyme.

Enzymes suitable for use with this process are described in detail above. Compounds that mimic the active sites of enzymes can also be used.

Silicates and Silicones

The sol comprises an alkoxy silane and/or an organotrialkoxy silane, and a poly(silicone). Typical silicates and silicones suitable for use in this process are described in detail above.

As described above, the poly(silicone) can be a poly(siloxane).

Typically, the molar ratio of alkoxy silane and/or organotrialkoxy silane to poly(silicone) in the sol is about 1:1, about 2:1, about 3:1, about 4:1, about 5:1, about 6:1, about 7:1, about 8:1, about 10:1, about 12:1, about 15:1, or about 20:1. The molar ratio can typically range from about 1:1 to about 20:1, from about 2:1 to about 8:1, or from about 3:1 to about 5:1.

Further, the molar ratio of alkoxy silane and/or organotrialkoxy silane to poly(siloxane) in the sol is about 1:1, about 2:1, about 3:1, about 4:1, about 5:1, about 6:1, about 7:1, about 8:1, about 10:1, about 12:1, about 15:1, or about 20:1. The molar ratio can typically range from about 1:1 to about 20:1, from about 2:1 to about 8:1, or from about 3:1 to about 5:1.

Hydrophilic Additives

The sol solution can optionally comprise a hydrophilic additive. These additives are typically incorporated to improve the hydrophilicity of the coating and increase the retention of enzymatic activity. Typical hydrophilic additives suitable for use in this process are described in detail above.

In one preferred embodiment, the sol comprises tetramethylorthosilicate, polydimethylsiloxane, and a crown ether.

Catalyst

A catalyst is included in the sol to assist with the polymerization process. More specifically, the catalyst can be introduced into the sol solution to assist with the polymerization reaction by which the polysilicate-polysilicone copolymer is produced. The result is a three dimensional polysilicate-polysilicone network copolymer, wherein the enzyme molecules are immobilized in the pores of the polymeric structure.

The catalyst can comprise ammonium fluoride, sodium fluoride, ammonium hydroxide, sodium hydroxide, or a combination thereof. A catalyst comprising ammonium fluoride is preferred.

Preparation of the Colloidal Sol Solution

In accordance with the method of the present invention, a colloidal solution can be prepared comprising the components described above.

Typically, an aqueous stock solution comprising the enzyme is prepared separately, and subsequently mixed with a second formulation comprising an organic solution of the silicate and silicone monomers and optional additives.

The enzyme is typically prepared in a buffered solution (e.g., phosphate buffer) in which pH values of the stock solution can range from about 6 to about 10. Typically, a pH between about 6 and about 8 is preferred.

The enzyme is mixed with a sufficient quantity of water to fully dissolve the enzyme while not increasing the required drying time. The enzyme stock solution typically comprises about 50 mg/mL, about 100 mg/mL, about 150 mg/mL, about 200 mg/mL, or about 300 mg/mL of the enzyme. The concentration of enzyme in the stock solution typically ranges from about 50 to about 200 mg/mL.

If an enzyme stock solution is separately prepared, it should be combined with the second formulation comprising the alkoxy silane and/or organotrialkoxy silane, and poly (silicone) species and optional additives and mixed until a finely dispersed emulsion or homogeneous mixture is achieved. The mixing preferably occurs under moderate to high shear, and can be conducted using any conventional mixing apparatus known in the art. Non-limiting examples of possible mixing apparatus include mechanical agitators, static agitators, rotating tank agitators, sonicators, and high pressure homogenizers. The mixing can occur as part of a batch, semi-batch, or continuous process.

A second solution, which comprises the silicate and silicone monomers and optional additives, may be prepared neat or in a dilute alcoholic solution. Methanol or ethanol are preferred alcohols for this purpose.

Several different methods can be used for combining the aqueous solution containing enzyme and the organic mixture containing monomers. These include addition of the organic monomeric species to the aqueous enzyme solution under vigorous mixing or addition of the aqueous enzyme solution to a mixture of monomers, or partially hydrolyzed monomers. Likewise the order of the addition of the catalyst and diluent can be easily varied to obtain catalytically active products.

The molar ratio of alkoxy silane and/or organotrialkoxy silane to hydrophilic additive is typically about 48:1, about 36:1, about 24:1, about 12:1, or about 4:1. The ratio can range from about 4:1 to about 60:1, from about 15:1 to about 45:1, or from about 30:1 to about 40:1.

The molar ratio of poly(silicone) to hydrophilic additive is typically about 12:1, about 9:1, about 6:1, about 3:1, or about 1:1. The molar ratio can range from about 1:1 to about 30:1, from about 2:1 to about 20:1, from about 5:1 to about 15:1, from about 6:1 to about 12:1, or from about 8:1 to about 10:1.

Further, the molar ratio of poly(siloxane) to hydrophilic additive is typically about 28:1, about 14:1, 12:1, about 9:1, about 7:1, about 6:1, about 3:1, or about 1:1. The molar ratio can range from about 1:1 to about 30:1, from about 2:1 to about 20:1, from about 3:1 to about 20:1, from about 10:1 to about 20:1, from about 5:1 to about 15:1, from about 6:1 to about 12:1, or from about 8:1 to about 10:1.

The molar ratio of alkoxy silane and/or organotrialkoxy silane to surfactant is typically about 130:1, about 65:1, about 32:1, about 16:1, or about 8:1. The ratio can range from about 4:1 to about 200:1, from about 40:1 to about 80:1, or from about 50:1 to about 70:1.

The molar ratio of alkoxy silane and/or organotrialkoxy silane to carbonic anhydrase is typically about 1300:1. The ratio can range from about 4000:1 to about 600:1.

The molar ratio of poly(silicone) to carbonic anhydrase is typically about 325:1. The molar ratio can range from about 1000:1 to about 160:1.

The molar ratio of poly(siloxane) to carbonic anhydrase is typically about 325:1. The molar ratio can range from about 1000:1 to about 160:1.

Typically, the amount of alkoxy silane and/or organotrialkoxy silane in dilute alcohol solution is at least about 10 wt. %, at least about 20 wt. %, at least about 30 wt. %, at least about 40 wt. %, or at least about 50 wt. %. The amount of alkoxy silane in dilute alcohol solution can range from about 5 wt. % to about 50 wt. %, from about 10 wt. % to about 40 wt. %, or from about 20 wt. % to about 30 wt. %.

Typically, the amount of poly(silicone) in dilute alcohol solution is at least about 2.5 wt. %, at least about 5 wt. %, at least about 7.5 wt. %, or at least about 12.5 wt. %. The mass percentage of poly(silicone) in dilute alcohol solution can range from about 1 wt. % to about 20 wt. %, from about 2.5 wt. % to about 15 wt. %, from about 5 wt. % to about 12.5 wt. %, or from about 5 wt. % to about 7.5 wt. %.

Further, the amount of poly(siloxane) in dilute alcohol solution is at least about 2.5 wt. %, at least about 5 wt. %, at least about 7.5 wt. %, or at least about 12.5 wt. %. The mass percentage of poly(siloxane) in dilute alcohol solution can range from about 1 wt. % to about 20 wt. %, from about 2.5 wt. % to about 15 wt. %, from about 5 wt. % to about 12.5 wt. %, or from about 5 wt. % to about 7.5 wt. %.

Coating the Colloidal Sol onto the Solid Support

In a further step of the method, solid state supports can be coated with the colloidal sol solution.

As discussed above, the solid state supports are typically etched or treated with a primer layer prior to the coating step.

Following the preparation of the sol, the coating can be applied to the solid support by any conventional method known in the art. For example, the solid support can be coated by dip coating, spin coating, spray coating, roll coating, or immersion coating. Immersion coating, dip coating, or spray coating are the preferred methods. Typically, the solution is immersion coated under moderate to high shear. Typically, spray coating is done with a high volume low pressure spray gun.

The solid supports can be coated with one, two or more layers of the sol solution. Additional layers serve to increase the overall thickness of the coating, and thereby increase the amount of enzyme that can be loaded onto the solid support.

When additional coatings are utilized, the coated solid supports are typically allowed to dry for approximately 15 to 30 minutes at room temperature. The coated supports are then re-immersed into the vessel containing the sol or re-sprayed with a spray gun. Alternatively, thermal curing can be applied in between coats to promote surface adhesion.

Drying the Coated Support

In a further step of the method, the coated solid support is dried.

Typically, some drying will occur over the course of the coating process. In most cases, however, additional drying time will be required after the coating process is complete. Typically, the coating is dried at room temperature.

The drying step involves substantially complete removal of the aqueous phase and alcohol products from the sol. As the sol dries, the alkoxysilane, organotrialkoxy silane, and poly (silicone) units undergo polymerization, gradually forming a network polymer gel while the enzyme and hydrophilic additives become entrapped within the pores of the polymer.

The resulting coating typically retains its porosity. For example, the coatings typically have an overall pore volume of at least about 3 μL/g to 500 μL/g. Coatings prepared according to this process typically have surface area of at least about 10 m$^2$/g, at least about 20 m$^2$/g, at least about 30 m$^2$/g, at least about 40 m$^2$/g, at least about 50 m$^2$/g, at least about 60 m²/g, at least about 70 m²/g, at least about 80 m²/g, at least about 90 m²/g, or at least about 100 m²/g.

Thermal Curing

The method for preparing an immobilized enzyme can comprise mixing (i) an alkoxy silane or an organotrialkoxy silane or metasilicate, (ii) a poly(silicone), (iii) a hydrophilic additive, (iv) a carbonic anhydrase, and (v) solvent to form a sol; contacting the sol with a catalyst to form a gel; and curing the gel at a temperature from about 55° C. to about 85° C.

The gel can be cured at a temperature from about 75° C. to about 100° C. for from about 48 hours to about 96 hours. The gel can be cured at a temperature from about 80° C. to about 100° C. for from about 48 hours to about 96 hours. Preferably, the gel can be cured at about 85° C. for about 72 hours.

When coating a solid support, the final composition can be thermally cured after the coating and drying steps are complete.

Typically, the coated supports are cured at a temperature between about 35° C. and 110° C. A curing temperature of 55° C. to 85° C. is preferred.

The curing time can range from about 24 to about 96 hours, depending on the curing temperature, the composition of the sol, and the number of layers that were applied.

Alternatively, a gradual ramping from 55° C. to 75° C. can be utilized. Preferred methods include 24 hours at 55° C. followed by 72 hours at 75° C.

The method for preparing an immobilized enzyme can comprise mixing (i) an alkoxy silane or an organotrialkoxy silane or metasilicate, (ii) a poly(silicone), (iii) a hydrophilic additive, (iv) a carbonic anhydrase, and (v) solvent to form a sol; contacting the sol with a catalyst to form a gel; and curing the gel at a temperature from about 55° C. to about 100° C.

Once cured, the gel can form particles as described in the section below.

Preparations of Particulate Suspensions from Xerogel Powders

As an alternative to using the colloidal suspensions to coat solid state supports, the suspensions can be allowed to gel, then the gel can be dried, cured, and milled into bulk powders. These powders are commonly called "xerogels". The powders can also be generated by spraying.

Typically, the powders are washed and hydrated in common buffers such as carbonate and phosphate. The pH of these buffers can range from 7 to 10. Since most activity testing is done in 0.8 M/1.2 M KHCO$_3$/K$_2$CO$_3$ solution (pH≈10), this provides an advantageous buffer to wash and hydrate the resulting powders in.

The powders can be ground with a mortar and pestle to improve hydration and particle distribution.

The powders can also be passed through sieves with different particle size cutoffs to narrow particle size distribution and improve hydration. Typically, sieves with cutoffs in the range of <500 µm, <250 µm, <125 µm, and <45 µm have been utilized.

After, washing and hydrating for a suitable amount of time the particles can be resuspended in the desired solvent. Typically, 0.8 M/1.2 M KHCO$_3$/K$_2$CO$_3$ solution (pH≈10) is used.

Typically, suspensions containing different weight percent of solid particles can be prepared for CO$_2$ capture. The desired weight percent is typically dependent on the type of contactor used. Weight percent suspensions ranging from 0.05 to 20 wt. % can be prepared. Typically in a batch type reactor, lower weight percent suspensions are used ranging from 0.05 to 10 wt. %. When these particles are utilized in a flow-through type system over packed-bed reactors or tray contactors, higher weight percent solutions may be required to achieve the desired overall CO$_2$ capture. These can range from 1 to 20 wt. %.

Once the particles are added to the buffered solvent, a variety of techniques can be used to distribute the particles and achieve a well dispersed solution. These include shaking, mechanical mixing, vortexing, sonication, or a combination thereof.

Processes and Systems for Removal of Carbon Dioxide

Coated solid supports, wherein a carbonic anhydrase is entrapped within a polysilicate-polysilicone copolymer derived coating, can be used to catalyze a process for removing CO$_2$ from a CO$_2$-containing gas.

Generally, the process comprises contacting a liquid with a CO$_2$-containing gas to promote diffusion of the CO$_2$ into the liquid in the presence of a coated solid support to catalyze hydration of the CO$_2$, thereby forming a treated liquid comprising hydrogen ions and bicarbonate ions. Hydrogen ions can also combine with carbonate ions already present in solution forming a second bicarbonate ion.

The process can also comprise contacting a liquid with a CO$_2$-containing gas; and contacting the CO$_2$ in the liquid with the immobilized enzyme described above to catalyze hydration of the CO$_2$ and form a treated liquid comprising hydrogen ions and bicarbonate ions.

The process can also comprise contacting a liquid with a CO$_2$-containing gas; and contacting the CO$_2$ in the liquid with particles of the polysilicate-polysilicone copolymer xerogel described above to catalyze hydration of the CO$_2$ and form a treated liquid comprising hydrogen ions and bicarbonate ions.

Generally, the enzyme can catalyze the hydration reaction that is the first step of a two-step sequence:

$$CO_2 + H_2O \rightarrow H^+ + HCO_3^- \quad (1)$$

$$CO_3^{2-} + H^+ \rightarrow HCO_3^- \quad (2)$$

By using carbonic anhydrase to catalyze CO$_2$ hydration [reaction (1)], the rate of conversion of CO$_2$ into the bicarbonate form is accelerated.

This reaction takes place preferably at a pH less than 10.5. The K$_{eq}$ for the hydration reaction at 25° C. is $1.7 \times 10^{-3}$; the reaction at equilibrium favors the CO$_2$/H$_2$O side of the equation. In reaction (2), the carbonate captures the proton produced in reaction (1) and creates a driving force to produce more bicarbonate.

Carbonic anhydrase can also be used to catalyze the dehydration of the bicarbonate back into CO$_3^{2-}$, CO$_2$, and water. The carbonate can be recycled back to the first reactor where the dehydration of CO$_2$ occurs. For example, the chemistry for dehydration of NaHCO$_3$ is as follows:

$$2NaHCO_3 \rightarrow Na_2CO_3 + H_2O + CO_2 \quad (3)$$

Upon heating, bicarbonate releases the CO$_2$ and water and forms carbonate ions that can be recycled to the hydration reaction. The CA increases the rate of the dehydration reaction as well.

The carbonic anhydrase can also be used to accelerate the capture of carbon dioxide in solutions of amines. Preferably, the amine species is selected from a tertiary amine and/or ammonia.

Similar to the solid supports, enzyme containing particles, wherein a carbonic anhydrase is entrapped within a polysilicate-polysilicone copolymer, or polysilicate-polysilicone copolymer coated particles, can be used to catalyze a process for removing CO$_2$ from a CO$_2$-containing gas.

Typically, the process comprises contacting a liquid containing a suspension of enzyme containing particulates with a $CO_2$-containing gas. An appropriate contactor is chosen to promote diffusion of the $CO_2$ into the liquid. As the $CO_2$ diffuses into the liquid it comes into contact with the enzyme-containing particles, which catalyze hydration of the $CO_2$, thereby forming a treated liquid comprising hydrogen ions and bicarbonate ions.

Typical reactors for utilizing a suspension derived approach include batch reactors, semi-batch, and continuous flow reactors such as packed columns with random packing or structured packing, and tray contactors.

System Design

The system used to hydrate carbon dioxide gas in a gas stream to form bicarbonate ions can use a variety of reactors, including a packed bed, a fluidized bed, or a continuous stirred tank. When a packed or fluidized bed reactor is used, the gas and liquid streams entering the reactor can be in a co-current or counter current configuration. For example, in a co-current system, the gas and liquid streams could enter the reactor in the form of microbubbles of gas in the liquid stream.

The packing of the reactors is preferably the coated support comprising immobilized carbonic anhydrase as described above.

Alternatively, the liquid stream can contain a suspension of polysilicate-polysilicone copolymer immobilized carbonic anhydrase particles as described above.

The configuration in the reactor could be similar to a distillation column wherein the packing material comprising the immobilized carbonic anhydrase is oriented to maximize the surface contact with the gas and liquid streams.

In one particular system, a two unit continuous flow system can be used to hydrate $CO_2$ gas to form bicarbonate ions in a $CO_2$ absorber and dehydrate the bicarbonate ions to $CO_2$, water, and carbonate ions in a $CO_2$ stripper. The units can have a packed tower design. A schematic diagram of this two unit system including an absorber 10 and a stripper 12 is depicted in FIG. 1A. A $CO_2$ gas stream 14 enters the bottom of the absorber 10, and a liquid stream 16 enters the top portion of the absorber 10. The liquid stream 16 is distributed over the top of the packing (not shown) in the middle portion of the absorber 10 by a distributor (not shown). The liquid stream 16 wets the surfaces of the packing and flows downward through the absorber 10 while the $CO_2$ gas stream 14 flows upward through the interstices in the packing counter-current to the flow of the liquid. The packing provides an area of contact between the liquid and gas phases, and includes carbonic anhydrase immobilized on its outer surface. The $CO_2$ in the gas stream is absorbed by the liquid, and the treated gas stream 18 leaves the top of the absorber. The liquid is enriched in $CO_2$ as it flows down the column, bicarbonate is formed, and the treated liquid stream 20 leaves the bottom of the absorber. The treated liquid stream 20 is pumped to a top portion of the stripper 12, and is distributed by a distributor (not shown) over packing The bicarbonate within the liquid stream 20 is converted to carbon dioxide, water, and carbonate. Reaction rates of this reaction to produce $CO_2$ can be increased by adding heat, reducing pressure, immobilizing carbonic anhydrase in the stripper, and by increasing the rate of removal of $CO_2$ from the stripper 12 by operating at below atmospheric pressure. The water and carbonate can be recycled and combined with the liquid stream 16 entering the absorber 10, and the carbon dioxide leaves the top of the stripper as gas stream 22 and can be further processed as desired.

Alternatively, the absorber can have carbonic anhydrase immobilized on standard reactor packing materials (such as Berl saddle, Intalox saddle, Raschig ring or Pall ring packings commonly used in packed towers) and can be contacted with a microbubble $CO_2$ gas and an aqueous carbonate solution to allow for increased surface area between the gas and liquid for transport of the $CO_2$ gas into the aqueous carbonate solution.

Figure 1B:
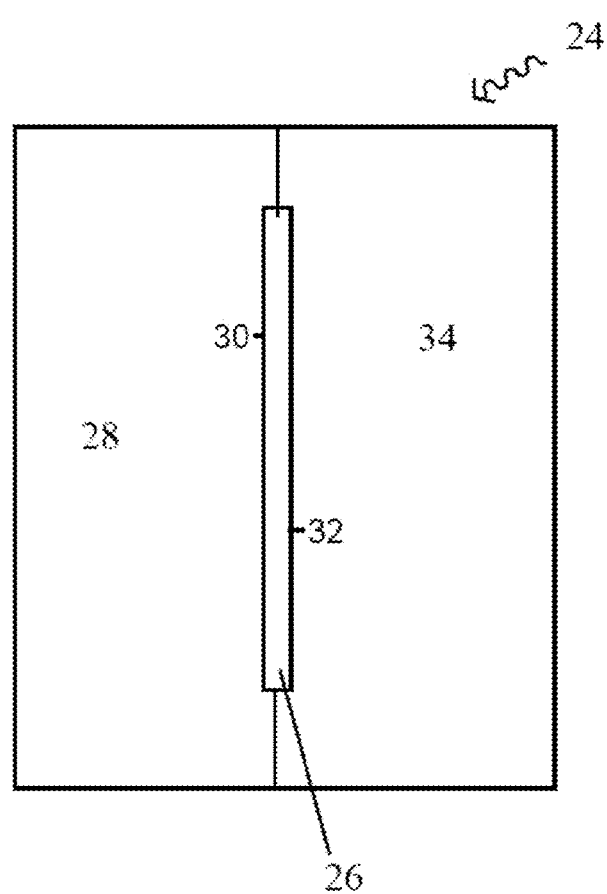

Additionally, the system can include a reactor 24 as shown in FIG. 1B having a membrane 26 wherein a gas stream 28 containing $CO_2$ is in contact with a first surface 30 of the membrane and an aqueous carbonate stream 34 is on a second surface 32 of the membrane. The membrane is permeable to at least the $CO_2$ gas, but is either impermeable to the aqueous carbonate stream 34 or the first surface 30 is impermeable to the stream 34. The membrane 26 can support an immobilized carbonic anhydrase as described herein. The $CO_2$ gas in the gas stream 28 can interact with the immobilized carbonic anhydrase and be converted to bicarbonate. The bicarbonate diffuses through the membrane 26 and is absorbed by the stream 34. The membrane material can be a polysaccharide, an ion exchange resin, a treated silicon oxide, a porous metal structure, a carbon rod or tube, a graphite fiber, a silica bead, a cellulose membrane, a gel matrix (e.g., a polyacrylamide gel, a poly(acryloyl morpholine) gel, a nylon mesh and the like). High surface area/volume membrane systems that can be used in this configuration are disclosed in U.S. Pat. No. 6,524,843.

Figure 1C:
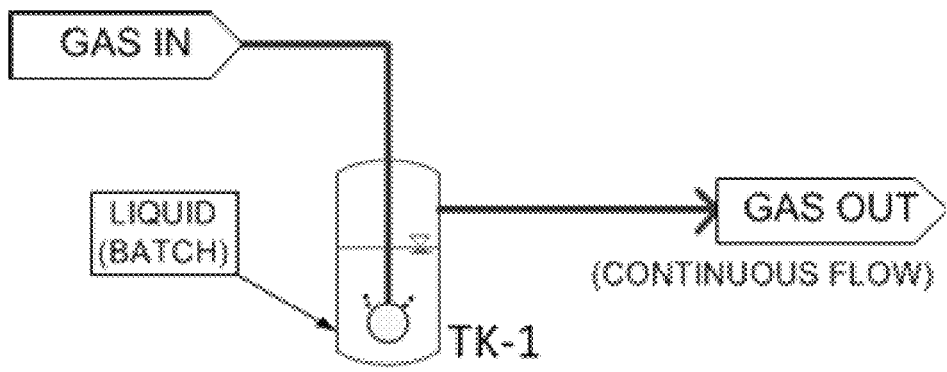

In another example, a semi-batch continuous flow system can be used to remove $CO_2$ gas from a mixed stream, as shown in FIG. 1C. A mixture containing $CO_2$ gas enters the tank TK-1 wherein $CO_2$ is absorbed into the liquid which can contain a suspension of immobilized enzymes. The immobilized enzymes can further be in the form of particles. As a result, the liquid gets enriched in bicarbonate upon $CO_2$ conversion and subsequently the treated gas stream with depleted $CO_2$ levels continuously flows from the tank as indicated on FIG. 1C.

The batch system can include a suspension of immobilized enzymes wherein the enzyme is carbonic anhydrase and the immobilization material comprises a polysilicate-polysilicone copolymer described in more detail herein. Thus, the semi-batch continuous flow system described above can contain a suspension of immobilized carbonic anhydrase particles of the particle size described herein wherein the carbonic anhydrase is immobilized in a polysilicate-polysilicone copolymer.

The immobilized carbonic anhydrase particles can also be immobilized in the form of particles and the immobilized carbonic anhydrase particles can be immobilized in an immobilization material derived from reaction of a sol and a catalyst, the sol comprising (i) an alkoxy silane or an organotrialkoxy silane or metasilicate, (ii) a poly(silicone), and (iii) a carbonic anhydrase.

The stripper can optionally have carbonic anhydrase immobilized on standard reactor packing materials and a feed of bicarbonate solution from the absorber. Reaction rates of this reaction to produce $CO_2$ can be increased by adding heat and the removal of $CO_2$ from the stripper could be increased by operating at below atmospheric pressure.

These system designs can be combined in different configurations depending on the specific application or gas stream to be treated. For example, the system specifications can be tailored to the $CO_2$ content of the feed stream and the overall purity, recovery, and contaminant levels required for the product streams along with the temperature and pressure requirements of both streams. The use of immobilized enzymes increases the range of system operating conditions and reduces the reactor sizes as compared to the corresponding free enzyme. A packed tower as described herein can be used as the absorber in conjunction with a membrane reactor as described herein as the stripper. Alternatively, a membrane reactor as described herein can be used as the absorber and a packed tower as described herein can be used as the stripper.

Figure 2:
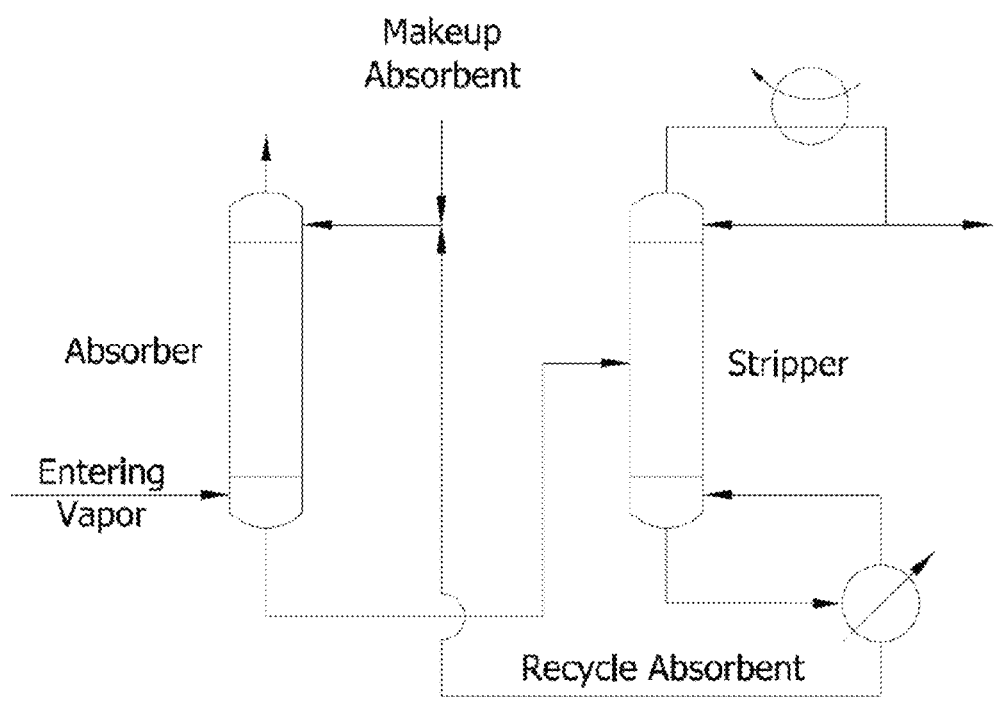
FIG. 2 is a schematic of the closed loop reactor utilized in Examples 21, 28, and 30.

Also, the system design can be generally as depicted in FIG. 2. For example, the carbon capture process unit comprises a standard absorption unit and a stripping (reactive distillation) unit. The core components of the carbon capture system (CCS) are an absorbing unit operation, a stripping unit operation, and a heat exchange component between the two unit operations. Peripheral equipment could include standard control hardware and software, flow monitoring and regulation (e.g., control valves, flow meters), pumps, pH monitoring (e.g., pH meters), temperature monitoring (e.g., temperature monitors), or any combination thereof. The additional equipment could provide means for monitoring and controlling the process.

The system can comprise a plurality of reaction vessels, wherein two or more reaction vessels contain the coated supports.

Carbonic Anhydrase

The carbonic anhydrase (CA) used in the systems described herein catalyzes the conversion of carbon dioxide to bicarbonate ions and protons. Suitable carbonic anhydrases have been previously described herein. Compounds or enzymes that mimic the activity of carbonic anhydrase, as described above, can also be utilized.

Liquid

As described above, the liquid is contacted with the $CO_2$-containing gas to help absorb the $CO_2$ and increase the $CO_2$ concentration in the liquid.

Preferably, the liquid comprises an organic or inorganic base. The base is a proton acceptor.

The base can be a metal hydroxide, a quaternary ammonium hydroxide, a metal carbonate, a quaternary ammonium carbonate, a quaternary ammonium alkoxide, a metal amide, a metal alkyl, a metal alkoxide, metal silanoate, an amine (primary, secondary, and tertiary), an amino acid, an alkanolamine, a conjugate base of a weak acid, or a combination thereof.

The metal hydroxides can include lithium hydroxide, sodium hydroxide, potassium hydroxide, rubidium hydroxide, cesium hydroxide, magnesium hydroxide, calcium hydroxide, strontium hydroxide, barium hydroxide, or a combination thereof. Also, ammonium hydroxide can be used in the aqueous liquid.

The metal carbonate can be lithium carbonate, sodium carbonate, potassium carbonate, rubidium carbonate, cesium carbonate, magnesium carbonate, calcium carbonate, strontium carbonate, barium carbonate, ammonium carbonate, a carbonate salt of an organic cation, or a combination thereof. For example, the carbonate salt of an organic cation can be a tetraalkyleammonium carbonate (e.g., tetramethylammonium carbonate, tetraethylammonium carbonate, tetrapropylammonium carbonate, tetrabutylammonium carbonate, tetrapentylammonium carbonate, or tetrahexylammonium carbonate) an alkyltrimethyl ammonium carbonate (e.g., ethyltrimethyl ammonium carbonate, propyltrimethyl ammonium carbonate, butyltrimethyl ammonium carbonate, pentyltrimethyl ammonium carbonate, hexyltrimethyl ammonium carbonate, hepyltrimethyl ammonium carbonate, octyltrimethyl ammonium carbonate, nonyltrimethyl ammonium carbonate, decyltrimethyl ammonium carbonate, dodecyltrimethyl ammonium carbonate, or undecyltrimethyl ammonium carbonate), an alkyltriethylammonium carbonate (e.g., methyltriethyl ammonium carbonate, propyltriethyl ammonium carbonate, butyltriethyl ammonium carbonate, pentyltriethyl ammonium carbonate, hexyltriethyl ammonium carbonate, hepyltriethyl ammonium carbonate, octyltriethyl ammonium carbonate, nonyltriethyl ammonium carbonate, decyltriethyl ammonium carbonate, dodecyltriethyl ammonium carbonate, or undecyltriethyl ammonium carbonate), an amino acid, or a combination thereof.

The quaternary ammonium hydroxide, quaternary ammonium carbonate, or quaternary ammonium alkoxide can be benzyltrimethylammonium hydroxide, choline hydroxide, diethyldimethylammonium hydroxide, dimethyldodecylethylammonium hydroxide, N,N,N,N',N',N'-hexabutylhexamethylenediammonium dihydroxide, hexadecyltrimethylammonium hydroxide, hexamethonium hydroxide, triethylmethylammonium hydroxide, tributylmethylammonium hydroxide, trihexyltetradecylammonium hydroxide, tetrapropylammonium hydroxide, tetrabutylammonium hydroxide, tetraoctadecylammonium hydroxide, methyltripropylammonium hydroxide, tetrabutylammonium ethoxide, tetraethylammonium hydroxide, tetrahexylammonium hydroxide, tetrakis(decyl)ammonium hydroxide, tetramethylammonium hydroxide, trimethylphenylammonium hydroxide, or a combination thereof.

The metal amide, metal alkoxide, or metal silanoate can be lithium tert-amoxide, lithium bis(trimethylsilyl)amide, lithium diethylamide, lithium dimethylamide, lithium diisopropylamide, sodium bis(trimethylsilyl)amide, potassium bis(trimethylsilyl)amide, lithium dicyclohexylamide, lithium trimethylsilanolate, sodium methoxide, potassium methoxide, lithium methoxide, sodium ethoxide, potassium ethoxide, lithium ethoxide, lithium isopropoxide, sodium tert-butoxide, potassium tert-butoxide, lithium tert-butoxide, sodium tert-pentoxide, potassium tert-pentoxide, magnesium ethoxide, magnesium di-tert-butoxide, sodium trimethylsilanolate, potassium trimethylsilanolate, or a combination thereof.

The amine can be a cyclic amine of 2-(2-chloro-6-fluorophenyl)ethylamine, 1,4-diazabicyclo[2.2.2]octane (DABCO® 33-LV), 1,5-diazabicyclo[4.3.0]non-5-ene, 1,4-diazabicyclo[2.2.2]octane, 1,8-diazabicyclo[5.4.0]undec-7-ene, 4-(dimethylamino)pyridine, 2,6-lutidine, piperidine, 1,8-(dimethylamino)naphthalene, 2,2,6,6-tetramethylpiperidine, 2,8,9-triisobutyl-2,5,8,9-tetraaza-1-phosphabicyclo[3.3.3]undecane, tripelennamine, aniline, benzylamine, N-methyl aniline, imidazole, pyrrole, pyridine, morpholine, or a combination thereof.

The amine can be a primary amine, a secondary amine, a tertiary amine, or a combination thereof.

The primary amine can be methylamine, ethylamine, propylamine, iso-propylamine, butylamine, iso-butylamine, sec-butylamine, tert-butylamine, pentylamine, iso-pentylamine, sec-pentylamine, tert-pentylamine, hexylamine, iso-hexylamine, sec-hexylamine, tert-hexylamine, ethylenediamine, (2-methylbutyl)amine, 2-aminopentane, 3-(tert-butoxy)propylamine, 2-amino-6-methylheptane, 1-ethylpropylamine, or a combination thereof.

Further, the secondary amine can be dimethylamine, diethylamine, dipropylamine, dibutylamine, dipentylamine, dihexylamine, methylethylamine, methylpropylamine, methylbutylamine, ethylpropylamine, ethylbutylamine, N-ethylmethylamine, N-isopropylmethylamine, N-butylmethylamine, N-ethylisopropylamine, N-tert-butylmethylamine, N-ethylbutylamine, 3-isopropoxypropylamine, chloro(diethylamino)dimethylsilane, 2,2'-(ethylenedioxy)bis(ethylamine), 1,3-bis(chloromethyl)-1,1,3,3-tetramethyldisilazane, N-tert-butylisopropylamine, N,N-diethyltrimethylsilylamine, di-sec-butylamine, or a combination thereof.

Additionally, the tertiary amine can be trimethylamine, triethylamine, tripropylamine, tributylamine, dimethylethylamine, dimethylpropylamine, dimethylbutylamine, diethylmethylamine, diethylpropylamine, diethylbutylamine, N,N-diisopropylmethylamine, N-ethyldiisopropylamine, N,N-dimethylethylamine, N,N-diethylbutylamine, 1,2-dimethylpropylamine, N,N-diethylmethylamine, N,N-dimethylisopropylamine, 1,3-dimethylbutylamine, 3,3-dimethylbutylamine, N,N-dimethylbutylamine, or a combination thereof.

The alkanolamine can be 2-amino-2-(hydroxymethyl)-1,3-propanediol (Trizma® base), propanolamine, ethanolamine, diethanolamine, dimethylethanolamine, N-methylethanolamine, triethanolamine, or a combination thereof.

The conjugate base of a weak acid could be an acetate, a citrate, a succinate, an oxalate, a malate, a malonate, a phosphate, a phosphonate, a sulfate, a sulfamate, or a combination thereof wherein the counterion can be a positive ion such as an alkali metal, an alkaline earth metal, an ammonium cations, or a combination thereof.

Preferably, the liquid comprises an aqueous liquid.

When the liquid is an aqueous liquid, the base is water soluble and does not denature the carbonic anhydrase.

Unless otherwise indicated, the alkyl groups described herein are preferably lower alkyl containing from one to eight carbon atoms in the principal chain and up to 20 carbon atoms. Alkyls can be substituted or unsubstituted and straight or branched chain. Examples of unsubstituted alkyls include methyl, ethyl, n-propyl, i-propyl, n-butyl, i-butyl, s-butyl, t-butyl, n-pentyl, i-pentyl, s-pentyl, t-pentyl, and the like. The term "substituted," as in "substituted alkyl," means that various heteroatoms such as oxygen, nitrogen, sulfur, phosphorus, and the like can be attached to the carbon atoms of the alkyl group either in the main chain or as pendant groups. For example, the substituted alkyl groups can have —C—X—C— fragments in the main chain wherein the X is a heteroatom. Further, the substituted alkyl groups can have at least one hydrogen atom bound to a carbon atom replaced with one or more substituent groups such as hydroxy, alkoxy, alkylthio, phosphino, amino, halo, silyl, nitro, esters, ketones, heterocyclics, aryl, and the like.

The abbreviation "PDMS" represents polydimethylsiloxane, the abbreviation "PDMS550" represents polydimethylsiloxane having an average molecular weight of 550 daltons, the abbreviation "TMOS" represents tetramethoxysilane or tetramethyl orthosilicate, the abbreviation "PEG 460" represents polyethylene glycol having an average molecular weight of 4600 daltons, and the abbreviation "MTMOS" represents methyltrimethoxysilane.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis and Entrapment of Carbonic Anhydrase in the Presence of 18-Crown-6 in Polysilicate/Polysiloxane Particles In a typical procedure, a 100 mL beaker was charged with tetramethyl orthosilicate (2.6 mL, 17.6 mmol), silanol-terminated poly(dimethyl siloxane) (average $M_w$=550; 2.2 mL) and 18-crown-6-ether (600 mg, 2.3 mmol). The mixture was stirred vigorously for 5 minutes to fully dissolve the 18-crown-6-ether.

Separately, a 150 mg/mL stock solution of carbonic anhydrase (carbonic anhydrase, NS81239, supplied by Novozymes A/S, Denmark) was prepared in 10 mM phosphate buffer (pH=7.2).

Next, 2.4 mL of stock A was added to the reaction beaker and the resulting heterogeneous mixture was stirred vigorously to generate a finely dispersed emulsion.

Next 112 µL of a 1 M aqueous solution $NH_4F$ were added to the reaction vessel. The mixture was subsequently stirred for 2 minutes, or until gelation began to be observed, via magnetic stirring. After 2 minutes of stirring, the beaker contained a highly viscous polymerized material that could no longer be mixed through stirring.

The polymerized material was then dried at room temperature for 1 h. After 1 h, the beaker was transferred to a 55° C. oven for 24 h, after which the temperature was increased to 75° C. for 72 h.

After curing the powder was collected, ground using a mortar and pestle, and then the dry mass was obtained.

In some cases, after obtaining the dry mass, the bulk powder was separated by size using a series of sieves.

The powder with the desired particle size was hydrated in 0.8M/1.2M $K_2CO_3$/$KHCO_3$ buffer at pH=10.0 for 72 hour under stirring/agitation. The particles were then collected via filtration, and an aliquot of the storage solution was collected to determine enzyme retention in the particles.

These particles were then washed thoroughly with fresh 0.8M/1.2M $K_2CO_3$/$KHCO_3$ buffer at pH=10.0 and dried or stored in 0.8M/1.2M $K_2CO_3$/$KHCO_3$ buffer at pH=10.0.

Example 2

Phosphate Buffer Diluted Synthesis and Entrapment of Carbonic Anhydrase in the Presence of 18-Crown-6 in Polysilicate/Polysiloxane Particles In a typical procedure, a 100 mL beaker was charged with 2.4 mL of a 150 mg/mL stock solution of carbonic anhydrase (carbonic anhydrase, NS81239, supplied by Novozymes A/S, Denmark), Next, 5.0 mL of 100 mM phosphate buffer was added and mixed thoroughly.

Next a solution containing tetramethyl orthosilicate (2.6 mL, 17.6 mmol), silanol-terminated poly(dimethyl siloxane) (average $M_w$=550; 2.2 mL) and 18-crown-6-ether (0.6 g, 2.2 mmol) was added under vigorous stirring (or vortexing).

A volume of 112 µL of a 1 M aqueous solution $NH_4F$ was added to the reaction vessel. The mixture was subsequently stirred until gelation began to be observed The sample was then cured and hydrated following the procedure described in Example 1.

Example 3

Methanol Diluted Synthesis and Entrapment of Carbonic Anhydrase in the Presence of 18-Crown-6 in Polysilicate/Polysiloxane Particles In a typical procedure, a 400 mL beaker was charged a 12 mL of a 150 mg/mL stock solution of carbonic anhydrase (carbonic anhydrase, NS81239, supplied by Novozymes A/S, Denmark), Next a solution containing tetramethyl orthosilicate (13 mL, 88 mmol), silanol-terminated poly(dimethyl siloxane) (average $M_w$=550; 11 mL) and 18-crown-6-ether (3 g, 11 mmol) was added under vigorous stirring (or vortexing).

Upon effective dispersion and subsequent emulsion formation, 15 mL of reagent grade methanol were added. Immediately after addition of the methanol, 0.5 mL of 1 M $NH_4F$ was added to the stirring mixture. The mixture began to thicken after 30 seconds, and gelation was observed in approximately 30 minutes.

The same procedure for thermal curing, hydration, and detection of enzyme retention that was described in Example 1 was used here.

Example 4

Methanol Diluted Synthesis and Entrapment of Carbonic Anhydrase in the Presence of 18-Crown-6 in Polysilicate/Polysiloxane Particles; Alternate Order of Addition In a typical procedure, a 400 mL beaker was charged a 12 mL of a 150 mg/mL stock solution of carbonic anhydrase (carbonic anhydrase, NS81239, supplied by Novozymes A/S, Denmark), Next, 0.5 mL of 1 M $NH_4F$ was added to the enzyme solution under stirring.

A separate stock solution of organic monomers (Stock B) was prepared by combining tetramethyl orthosilicate (13 mL, 88 mmol), silanol-terminated poly(dimethyl siloxane) (average $M_w$=550; 11 mL), and 25 mL of methanol.

Separately, a stock solution of 18-crown-6 (3 g, 11 mmol; Stock C) and 25 mL of reverse osmosis (RO) water was prepared.

Stock solutions B and C were then combined and added to the beaker containing enzyme under vigorous stirring. The mixture began to thicken quickly, and gelation was observed in approximately 30 seconds.

The same procedure for thermal curing, hydration, and detection of enzyme retention that was described in Example 1 was used here.

Example 5

Methanol Diluted Synthesis and Entrapment of Carbonic Anhydrase in the Presence of Poly(Ethylene Glycol) in Polysilicate/Polysiloxane Particles Similar to Example 4, a 400 mL beaker was charged a 12 mL of a 150 mg/mL stock solution of carbonic anhydrase (carbonic anhydrase, NS81239, supplied by Novozymes A/S, Denmark), Next, 0.5 mL of 1 M $NH_4F$ was added to the enzyme solution under stirring. A separate stock solution of organic monomers (Stock B) was prepared by combining tetramethyl orthosilicate (13 mL, 88 mmol), silanol-terminated poly(dimethyl siloxane) (average $M_w$=550; 11 mL), and 25 mL of methanol.

Separately, a stock solution of polyethylene glycol, $M_r$=570-630) (3 g; Stock C) and 25 mL of RO water was prepared.

Stock solutions B and C were then combined and added to the beaker containing enzyme under vigorous stirring. The mixture began to thicken quickly, and gelation was observed in approximately 30 seconds.

The same procedure for thermal curing, hydration, and detection of enzyme retention that was described in Example 1 was used here.

This procedure was also used to make derivative containing polyethylene glycol (typical $M_n$=4,600), polyethylene glycol (typical $M_n$=8,000), and poly(ethylene oxide) (approximate $M_w$=100,000).

Example 6

Incorporation of Hydrophobic Additives in the Methanol Diluted Synthesis and Entrapment of Carbonic Anhydrase in the Presence of 18-Crown-6 in Polysilicate/Polysiloxane Particles Similar to Example 3, a 400 mL beaker was charged a 12 mL of a 150 mg/mL stock solution of carbonic anhydrase (carbonic anhydrase, NS81239, supplied by Novozymes A/S, Denmark), Next a solution containing tetramethyl orthosilicate (11.8 mL, 80 mmol), trimethoxymethyl silane (1.14 mL; 8 mmol), silanol-terminated poly(dimethyl siloxane) (average $M_w$=550; 11 mL) and 18-crown-6-ether (3 g, 11 mmol) under vigorous stirring (or vortexing).

Upon effective dispersion, subsequent emulsion formation, 15 mL of reagent grade methanol were added. Immediately after addition of the methanol, 0.5 mL of 1 M $NH_4F$ was added to the stirring mixture.

Gelation was observed in approximately 30 minutes.

The same procedure for thermal curing, hydration, and detection of enzyme retention that was described in Example 1 was used here.

This procedure was also used to prepare xerogels containing derivatives containing iso-butyl(trimethoxy)silane, n-butyl(trimethoxy)silane, and n-octyl(trimethoxy)silane in a 1:10 molar ratio with tetramethylorthosilicate.

Example 7

Ethanol Diluted Synthesis and Entrapment of Carbonic Anhydrase in the Presence of 18-Crown-6 and CTAB in Polysilicate/Polysiloxane Particles In a typical procedure, a 250 mL beaker was charged a 3.6 mL of a 150 mg/mL stock solution of carbonic anhydrase (carbonic anhydrase, NS81239, supplied by Novozymes A/S, Denmark), To this enzyme solution, 0.15 g of cetyl trimethylammonium bromide (CTAB, 0.4 mmol) was added and stirred to fully dissolve.

Next a solution containing tetramethyl orthosilicate (3.9 mL, 26 mmol), silanol-terminated poly(dimethyl siloxane) (average $M_w$=550; 3.3 mL) and 18-crown-6-ether (0.9 g, 3.3 mmol) was added under vigorous stirring (or vortexing). Upon effective dispersion and subsequent emulsion formation, 4.5 mL of 0.1 M $NH_4F$ was added to the stirring mixture.

The mixture began to turn opaque immediately, and 27 mL of reagent alcohol (90% ethanol, 5% methanol, 5% isopropanol) was quickly added under vigorous stirring.

After 10-15 seconds, this mixture began to thicken, and a second aliquot of 7.5 mL of reagent alcohol was added with stirring to facilitate transfer of the mixture.

It was then poured into a shallow container (6"×6"×1") and left to dry overnight at room temperature.

The following day, the container was placed in a 75° C. oven for 72 hours.

The same procedure for powder processing, hydration, and detection of enzyme retention that was described in Example 1 was used here.

Example 8

Figure 3:
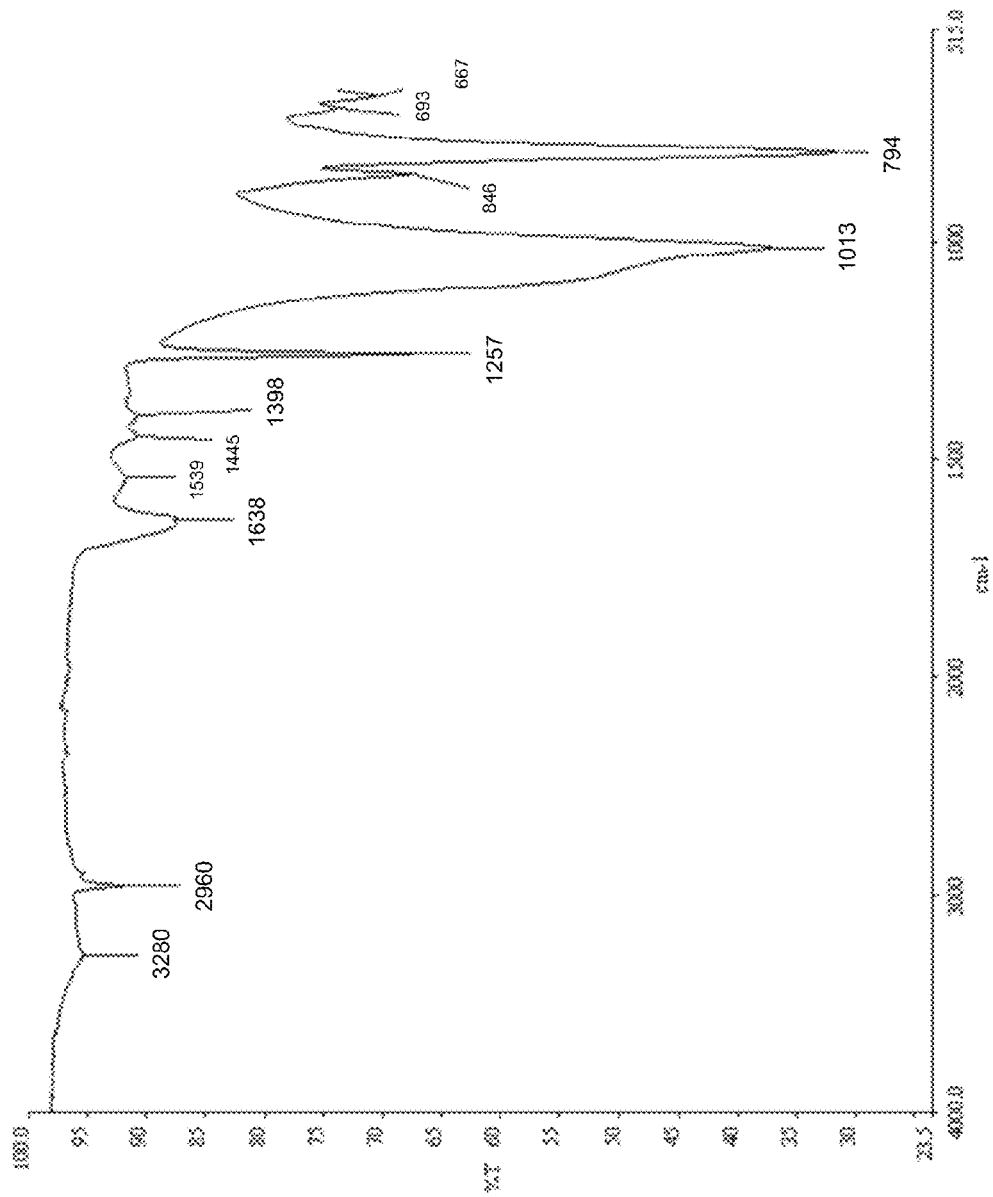
FIG. 3 is a FTIR of a CA/18-crown-6 containing polysilicate/polysiloxane xerogel powder generated using the synthetic procedure in Example 4.

Characterization of Polysilicate/Polysiloxane Particles Containing Carbonic Anhydrase A representative FTIR spectrum of particles generated using the synthetic methods described in Example 4 is shown in FIG. 3. Diagnostic peaks corresponding to Si—O bonding are seen at 794 cm$^{-1}$ and 1013 cm$^{-1}$. Further, the peaks at 1257 cm$^{-1}$ and 2960 cm$^{-1}$ indicate successful incorporation of the PDMS. The immobilized enzyme shows a series of peaks from 1375 cm$^{-1}$ to 1680 cm$^{-1}$. These spectral features are typically found in xerogel powders prepared using the combination of tetramethylorthosilicate, polydimethylsiloxane, and carbonic anhydrase in the ratios described in Examples 1 through 7.

Typically, the incorporation of 18-crown-6 and polyethylene glycol is not identifiable by FTIR analysis as their main diagnostic peaks are overlapped by the other components of the matrix.

Figure 4:
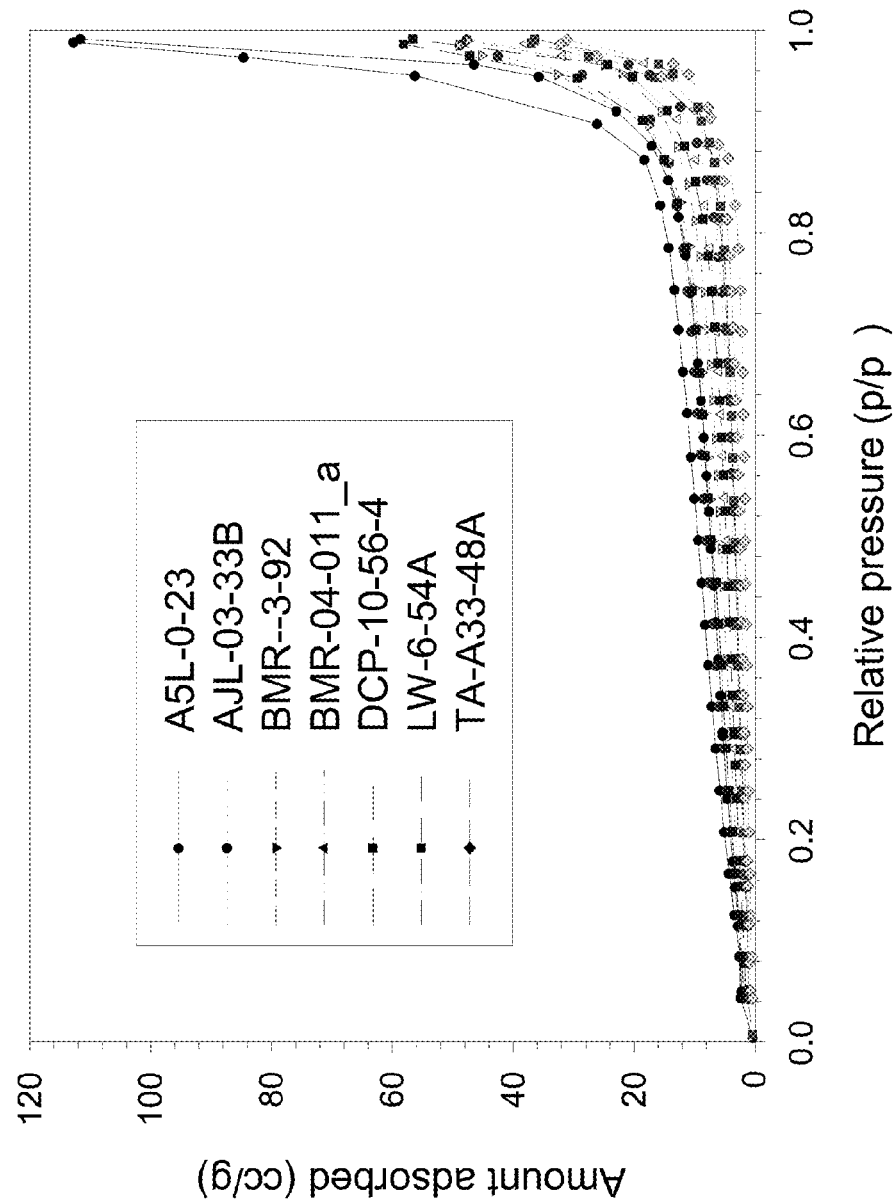
FIG. 4 contains BET nitrogen sorption isotherms of representative xerogel powder samples.

A series of representative Brunner-Emmett-Teller (BET) nitrogen sorption isotherms collected on samples prepared according to the experimental procedures described in Example 3 (AJL-03-33B, BMR-3-92, BMR-04-011a, DCP-10-56-4, LW-6-54a, and TA-a33-48A) and Example 7 (A5L-0-23) are shown in FIG. 4. The average surface area (m$^2$/g) ranged from 5.83 to 18.42 m$^2$/g, with an average of surface area of 10.4 m$^2$/g.

Figure 5:
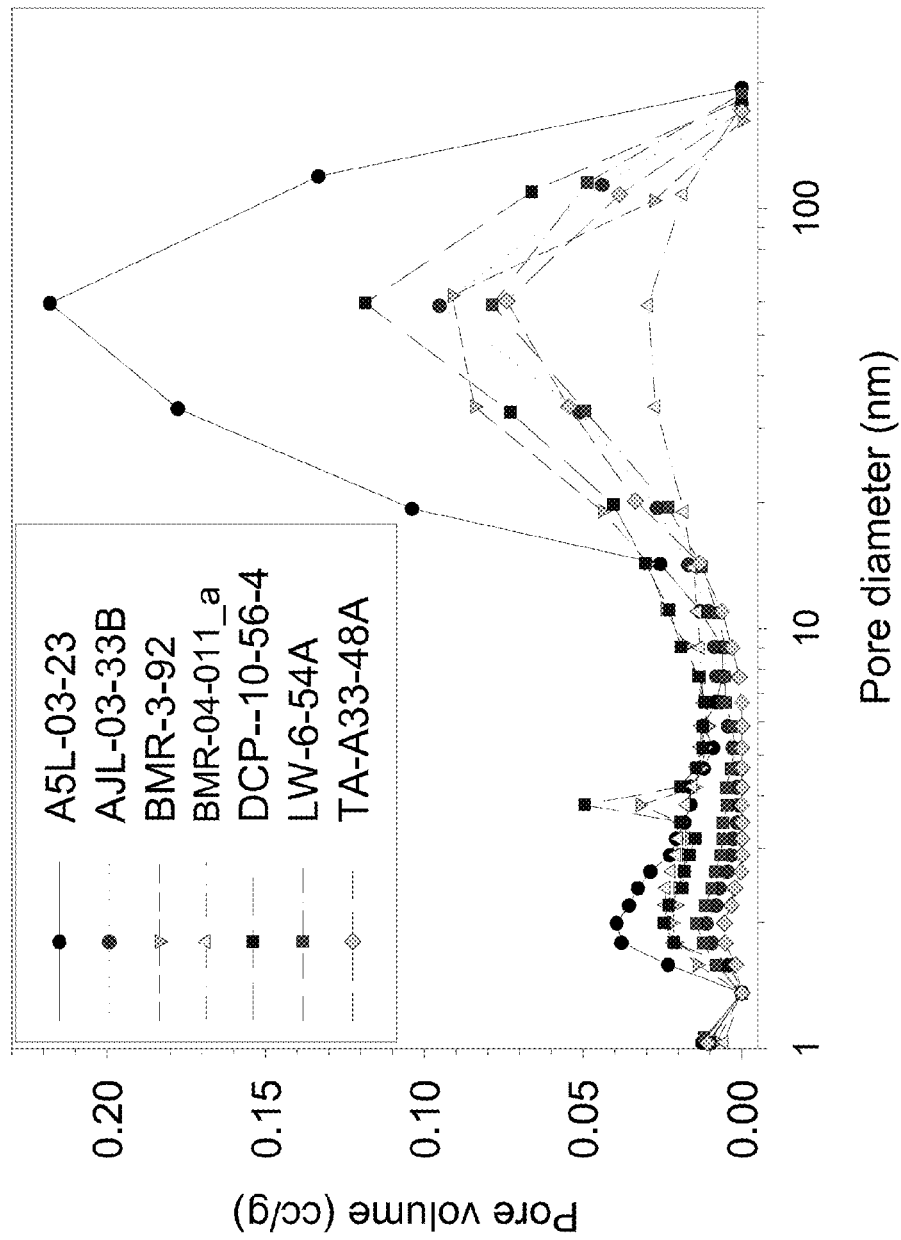
FIG. 5 contains a graph showing BJH pore size distribution in representative xerogel powder samples.
Figure 6A:
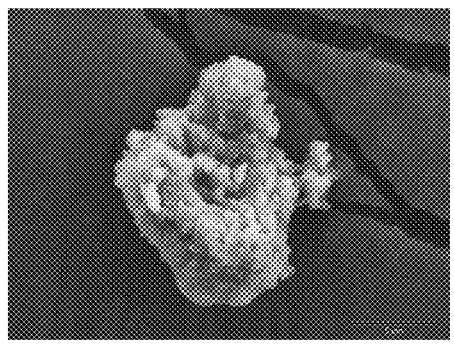
FIGS. 6A-D show SEM images of xerogel particulates generated using the synthetic procedure described in Example 3 containing 18-crown-6.
Figure 6B:
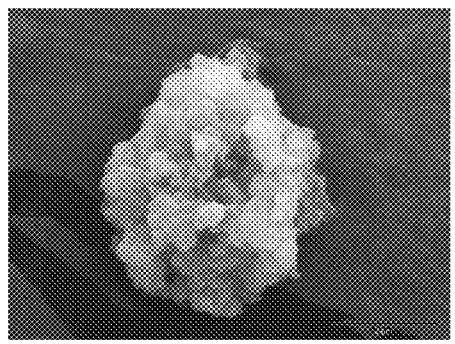
Figure 6C:
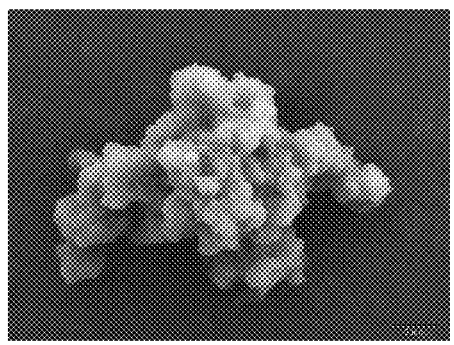
Figure 6D:
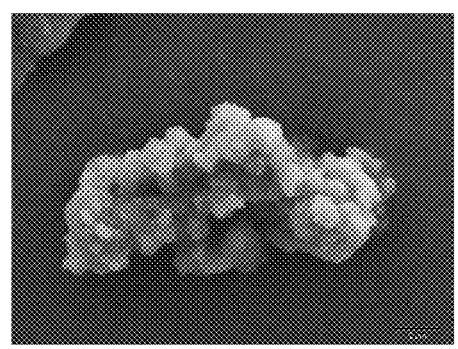

As shown in FIG. 5, the pore volume distributions obtained from Barrett-Joyner-Halenda (BJH) analysis on the previous samples showed pore volumes (cc/g) ranging from 0.0344 to 0.172, with calculated average pore volume of 0.059 cc/g.

The pore diameters obtained from aforementioned BJH analysis showed median pore sizes ranged from 10 nm to 80 nm.

The sample prepared according to the methods in Example 7 (A5L-0-23) showed the highest surface area (18.42 m$^2$/g) and pore volume (0.172 cc/g) in this series.

A series of scanning electron microscopy images (SEM) of a sample prepared according to the procedure in Example 3 are shown in FIG. 6. The representative images show particle agglomerates that are roughly 10 to 20 µm across. The agglomerates appear to be composed of smaller primary particles.

Example 9

Activity Testing of Polysilicate/Polysiloxane Particles Containing Carbonic Anhydrase in a Batch Reactor To test the activity of polysiloxane/polysilicate particles containing carbonic anhydrase, suspensions were prepared at different weight percentages of particulates and tested in a batch reactor system.

The batch reactor consisted of a sealed vessel that is pressurized between 60 and 100 psig. The feed gas consisted of 15% $CO_2$ balanced with $N_2$. The experiments described herein were conducted at room temperature.

The gas phase was mixed using a mechanical stirring rod, and the liquid phase was mixed with a magnetic stir bar. The mixing of the liquid was slow enough that the surface area remains unchanged throughout the experiment.

After charging the vessel with $CO_2$ mixture the pressure drop in the vessel was monitored over a 10 minute time period. Using the known number of moles of $CO_2$ in the vessel, the pressure, and the surface area of the solution, the $K_G$ of the suspensions was calculated and expressed in mmol/s·m$^2$·kPa.

Typically, samples were tested in 100 mL of 0.8M/1.2M $K_2CO_3$/$KHCO_3$ buffer at pH=10.0 with varying weight percent loadings and/or the amount of enzyme present in the reactor.

Table 1 shows the activity of some representative samples prepared according to the methods described in Examples 1 through 7. The samples shown in Table 1 represent a wide range of synthesis methods, formulations, weight percent loadings, and processing.

TABLE 1

Activities of polysilicate/polysiloxane particles in a batch reactor

| | Sample preparation | Weight Percent (%) | Xerogel Processing | Mass of enzyme in the reactor (mg) | $K_G$ (mmol/s · m$^2$ · kPa) |
|---|---|---|---|---|---|
| 1 | Example 3; No enzyme | 0.20% | <125 µm sieve | NA | 0.012 |
| 2 | Example 7 | 0.20% | <125 µm sieve | 8.1 mg | 0.075 |
| 3 | Example 3 | 0.20% | <125 µm sieve, Sprayed and Collected | 12.1 mg | 0.077 |
| 4 | Example 4 | 0.20% | Mechanical stirring and sonication | 15.7 mg | 0.063 |
| 5 | Example 4 | 0.30% | Mechanical stirring and sonication | 23.5 mg | 0.086 |
| 6 | Example 4; PEG$_{4600}$ | 0.20% | Mechanical stirring and sonication | 7.24 mg | 0.118 |
| 7 | Example 4; PEG$_{8000}$ | 0.30% | Mechanical stirring and sonication | 25.2 mg | 0.102 |
| 8 | Example 5 | 0.20% | Mechanical stirring and sonication | 13.3 mg | 0.149 |

TABLE 1-continued

Activities of polysilicate/polysiloxane particles in a batch reactor

| | Sample preparation | Weight Percent (%) | Xerogel Processing | Mass of enzyme in the reactor (mg) | $K_G$ (mmol/s · m² · kPa) |
|---|---|---|---|---|---|
| 9 | Example 5; TMOS/MTMOS | 0.20% | Mechanical stirring and sonication | 9.0 mg | 0.094 |
| 10 | Example 5; TMOS/iso-butyl TMOS | 0.20% | Mechanical stirring and sonication | 15.7 mg | 0.133 |
| 11 | Example 2 | 0.20% | Mechanical stirring and sonication | 17.8 mg | 0.157 |
| 12 | Example 2; No PDMS | 0.20% | Mechanical stirring and sonication | NA | 0.021 |
| 13 | Example 2; No 18-crown-6 | 0.20% | Mechanical stirring and sonication | 13.5 mg | 0.134 |

Entry #1 in Table 1 was a representative negative control, prepared by the synthetic procedure described in Example 3, but with phosphate buffer used to supplement the enzyme carbonic anhydrase. The relative $K_G$ of this sample was 0.012 mmol/s·m²·kPa, which was similar to a blank solution containing no catalyst (average $K_G$=0.011 mmol/s·m²·Pa). This result clearly indicates that xerogel particles without carbonic anhydrase do not accelerate $CO_2$ absorption into the test solution.

Entries #2-13 in Table 1 describe the activities of sample prepared in the presence of carbonic anhydrase according to the methods described in Examples 1 to 7. With the exception of entry #12, all samples showed considerable enhancement over the blank solvent.

Entry #12 in Table 1 shows a sample prepared according to Example 2 in the absence of hydroxyl terminated $PDMS_{550}$. After washing and hydration, quantitation of the enzyme suggested little to no enzyme was encapsulated in the remaining silicate particulates. This was evident in the very low activity at 0.2 wt. % xerogel loading.

Figure 7:
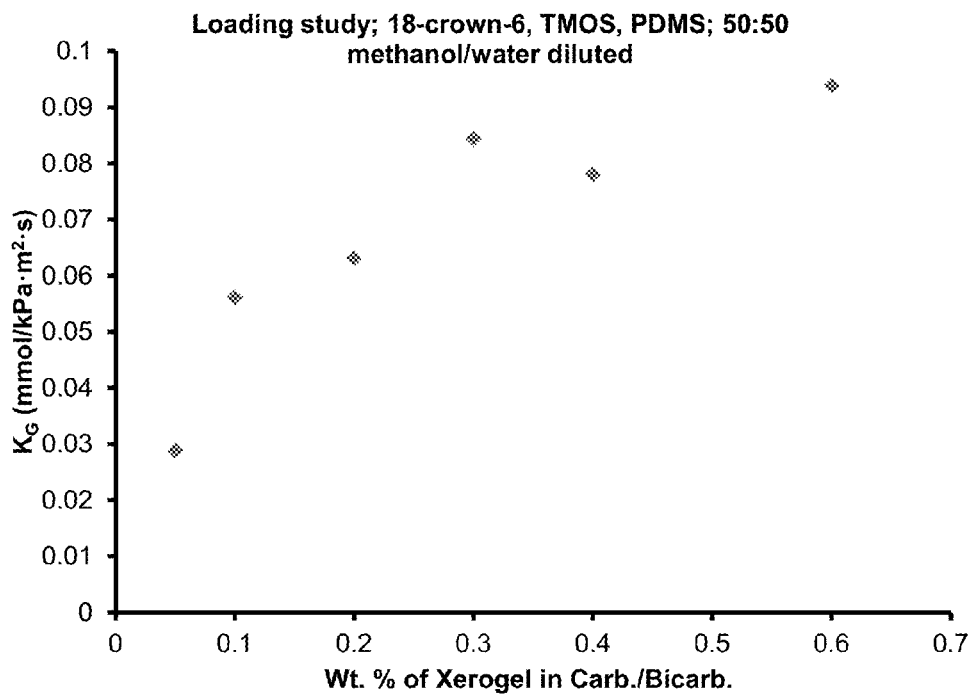
FIG. 7 shows a weight percent loading study of a CA/18-crown-6 containing polysilicate/polysiloxane xerogel generated using the synthetic procedure in Example 4.

In FIG. 7, a representative loading study of a sample prepared according to the synthetic methods described in Example 4 is shown. Similar behavior was observed in multiple loading studies.

Example 10

Activity Testing of Polysilicate/Polysiloxane Particles Containing Carbonic Anhydrase in a Counter-Current Flow Column To evaluate the use of these particulates in a flow-through reactor, different weight percent solutions were pumped over random (Tipton ⅛ in. ceramics) and structured packing (Sulzer Mellapak® 500X with a 2" column diameter).

Figure 8:
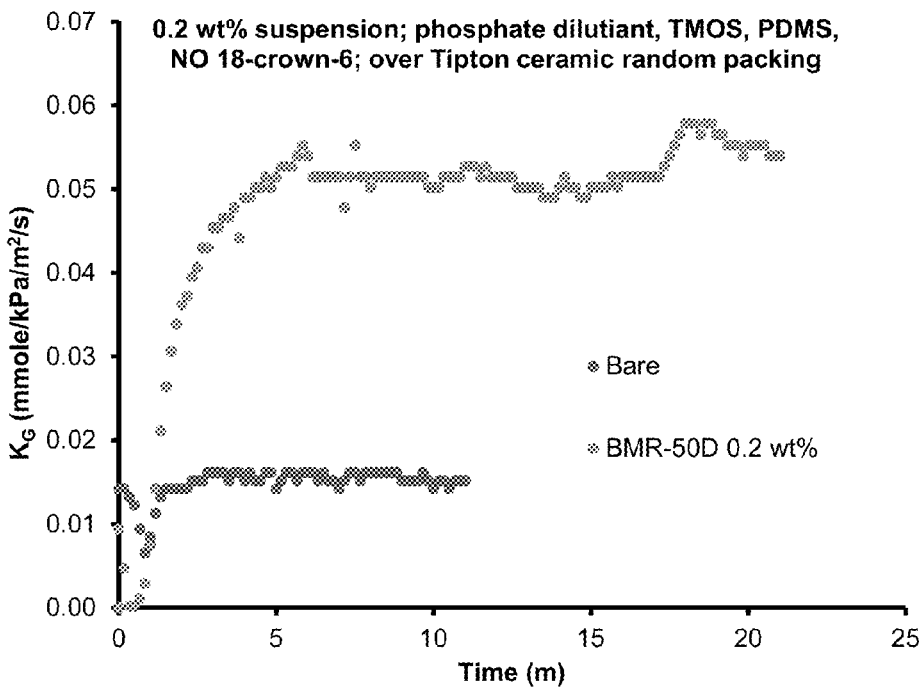
FIG. 8 shows a flow-through experiment conducted by flowing a 0.2 wt. % suspension of particles prepared using the synthetic method described in Example 2 over ⅛ in. Tipton ceramic spheres.

In FIG. 8, a 0.2 wt. % suspension of particles in a 0.8M/1.2M $K_2CO_3/KHCO_3$ buffer at pH=10.0 prepared according to Example 2 (except that it did not contain 18-crown-6), was pumped using a peristaltic pump over 65 g of ⅛ in. Tipton ceramic spheres at a controlled rate (20 mL/minutes) from the top of the column. A gas comprising 15% $CO_2$ (balanced with $N_2$) was flowed upwards from the bottom of the column. Quantitation of $CO_2$ conversion was performed using a non-dispersive infrared detector (NDIR) monitoring the $CO_2$ gas at the output of the column. The differential between the $CO_2$ content of the output gas versus the feed gas was used to calculate the rate of absorption.

The study in FIG. 8 was conducted for approximately 20 minutes. The sample showed an average $K_G$ of 0.051 mmol/s·m²·kPa at 0.2 wt. % loading. As shown in the blue trace, the bare Tipton ceramic packing showed an average $K_G$ of 0.015 mmol/s·m²·kPa representing approximately a 3.3 fold acceleration over the blank packing In a similar experiment, a 1.2 wt. % suspension of particles, prepared according to Example 1, was analyzed for activity over ⅛ in. Tipton ceramic spheres for 20 minutes. The sample showed a steady state $K_G$ of 0.08 mmol/s·m²·kPa, which corresponds to approximately a 6 fold improvement in $K_G$ over blank.

In a separate experiment, a 0.4 wt. % sample prepared using the methods described in Example 3 was analyzed in flow-through studies over Sulzer Mellapak® 500X with a 2" column diameter. The suspension was pumped at a controlled rate (218 mL/minute) from the top of the column. A gas comprising 15% $CO_2$ (balanced with $N_2$) was flowed upwards from the bottom of the column (2.18 SLPM). The average $K_G$ for the 0.4 wt. % suspension was calculated to be 0.0358 mmol/s·m²·kPa corresponding to an average rate enhancement (multiplier) of 2.78.

Example 11

HF Etching of Ceramic Supports

A 5000 mL plastic bucket was charged with 2600 g of ⅛ inch ceramic spheres (Tipton Corp.), and subsequently covered with 2 L of 10% aqueous HF solution. The solution was manually stirred using a large plastic spatula every 0.5 hours for the first three hours. The solution was then allowed to sit overnight at room temperature and ambient pressure, while covered with a plastic lid.

After 24 hours, the HF solution was decanted, and the ceramic spheres were washed 3 times over a sifter with reverse osmosis treated water. After washing, the spheres were dried at 80° C. for 24 hours before further use.

Example 12

Hydrogen Peroxide/Ammonium Hydroxide Etching of Ceramic Supports

A 2500 mL PYREX beaker was charged with 1000 g of ⅛ inch ceramic spheres (Tipton Corp.), and subsequently covered with 900 mL of water, 300 mL of $H_2O_2$ (30% aqueous solution), and 300 mL of ammonium hydroxide (28-30% w/w Reagent A.C.S.). The solution was heated on a hot plate to 80° C. and manually stirred every 0.5 hours for 3 hours. After 3 hours, the etching solution was decanted, and the ceramic spheres were washed 3 times over a sifter with reverse osmosis treated water.

After washing, the spheres were dried at 80° C. for 24 hours before further use.

Example 13

Coating Ceramic Spheres with Immobilized Carbonic Anhydrase in a Polysilicate/Polysiloxane Copolymer Containing 18-Crown-6 Using Aqueous $NH_4F$ Catalyst A 600 mL beaker was charged with tetramethyl orthosilicate (2200 µL, 14.9 mmol), silanol-terminated poly(dimethylsiloxane) (average $M_w$=550; 2200 µL) and 18-crown-6-ether (600 mg, 2.3 mmol). The mixture was sonicated for 5 minutes to homogenize.

Next, 1600 µL of stock A (as described in Example 1) were added to the reaction beaker and the resulting heterogeneous mixture was sonicated for 1 minute, or until a finely dispersed emulsion was observed.

Immediately following sonication, 112 µL of a 1 M aqueous $NH_4F$ solution were added to the reaction vessel.

Etched ceramic spheres (65 g) were then promptly added to the reaction beaker, and the mixture was subsequently stirred with a metal spatula for 2 minutes, or until gelation began to be observed.

After the onset of gelation, the coated ceramic was distributed onto a mesh screen and the spheres were evenly spaced to ensure contact was minimal between pieces prior to drying. The mesh screens containing coated ceramic spheres were then transferred to an oven (temperature set point at 55° C.) and allowed to dry for 24 hours.

The beads were allowed to soak/equilibrate in 50 mL of buffer (0.8M/1.2M $K_2CO_3$/$KHCO_3$ buffer at pH=10.0) for 48 hours. The coated ceramic spheres were subsequently rinsed 3 times with water to remove leached protein, and stored in 50 mL buffer (0.8M/1.2M $K_2CO_3$/$KHCO_3$ buffer at pH=10.0)

Example 14

Coating Ceramic Spheres with Immobilized Carbonic Anhydrase in Polysilicate/Polysiloxane Copolymer Containing Surfactants Using Aqueous $NH_4F$ Catalyst A 600 mL beaker was charged with tetramethyl orthosilicate (2200 µL, 14.9 mmol) and silanol-terminated poly(dimethylsiloxane) (average $M_w$=550; 2200 µL). The mixture was sonicated for 5 minutes to homogenize.

Next, 1600 µL of stock A (as described in Example 1) were combined with TRITON X-100 surfactant (200 µL, 0.2 mmol) followed by vortexing. This solution was subsequently added to the reaction beaker, and the resulting heterogeneous mixture was sonicated for 1 minute (or until a finely dispersed emulsion was observed). Similar studies were done with Tween 20, and with hexadecyltrimethyl ammonium bromide.

Immediately following vortexing, 112 µL of a 1 M aqueous $NH_4F$ solution were added to the reaction vessel.

Etched ceramic spheres (65 g) were then promptly added to the reaction beaker, and the mixture was subsequently stirred for 2 minutes with a metal spatula, or until gelation began to be observed.

The drying and hydration method for these samples was the same as that used in Example 13.

Example 15

Characterization of Ceramics with a Single Silica/Enzyme Coat Generated Using Aqueous $NH_4F$ Catalyst Samples of coated ceramic spheres were prepared using the method described in Example 13. The mass of the silica/enzyme coating adhered to the surface of the samples calculated via gravimetric analysis of the mass before coating and after drying. From these calculations, on average about 2 grams of mass was added to the surface of the ceramic spheres. The mass of coating typically ranged from 1.5 g to 2.5 g. Given the surface area of the ceramic spheres, an average film thickness of 25 µm was determined. The film thickness typically ranged from 15 to 35 µm. The average CA loading on the packing material was determined to be 1.9 g CA/L packing, using the methods described in Example 13. The CA loadings typically ranged from 1.3 to 2.5 g CA/L packing Further characterization of the silica/enzyme coated packing material was obtained through the use of scanning electron microscopy (SEM), as shown in FIG. 9A-D. As seen in FIG. 9, the resulting polysiloxane/polysilicate coating has a moderately high surface area (FIG. 9B) and there is evidence of porosity (FIGS. 9 C and D). Furthermore, low magnification view shows that the coating on the ceramic spheres is fairly uniform in nature and effectively covers the entire surface (FIG. 9A).

Example 16

Activity Studies Utilizing Ceramics with a Single Silica/Enzyme Coat Generated Using Aqueous $NH_4F$ Catalyst To test the inherent activity of multiple coating formulations on ⅛ inch ceramic spheres (Tipton Corp.), a single pass reactor (SPR) was constructed and utilized. The SPR analysis system functions as a small-scale absorber column and does not use a stripper column to regenerate solvent. Coated ceramic spheres were packed into a 78.5 cm tall×⅝ inch i.d. counter-flow column. A 0.8M/1.2M $K_2CO_3$/$KHCO_3$ buffer at pH=10.0 at 30° C. was applied at a rate of 20 mL/minute from the top of the column, and 15% $CO_2$ gas (balanced with $N_2$) moved upward from the bottom of the column. The quantity of $CO_2$ gas at the output of the column was monitored by a non-dispersive infrared detector (NDIR) and the differential between the $CO_2$ content of the output gas versus the feed gas was used to calculate the rate of absorption.

In a typical procedure, a daily check was performed on the NDIR analyzer. If the analyzer did not meet satisfactory requirements, the system was recalibrated (15% $CO_2$ calibration).

On average, 65 g of ⅛" ceramic spheres (Tipton Corp.) were coated via the sol-gel processing described in Example 13.

After 48 hours and two hydration/washing cycles, the buffer solution was decanted, and the ceramic spheres were loaded into the reactor column. The reactor column contained a mesh screen to prevent the spheres from passing all the way through the column. The column was secured in place with O-rings between the sanitary fittings of at the top and bottom of the column. The column was secured in place using clamps at the top and bottom of the apparatus, and a liquid dispenser was inserted within the column as close to the center as possible. The $CO_2$ gas flow was started, the desired pressure established, and the NDIR reached a steady state. The liquid flow was started (typically 20 mL/minute). The data was logged for the experiment using a pre-designed LABVIEW program, while simultaneously logging readings from the NDIR, pH, and temperature by hand.

Enzyme activity was calculated based on the magnitude of $CO_2$ conversion (i.e., $CO_2$ out mol %) and was reported as the % conversion and the overall mass transfer coefficient ($K_G$) (mmol/s·m²·kPa).

Table 2 shows $CO_2$ conversion, KG, and the ratio of KG for the enzymatic reaction to that of control (multiplier) for several formulations generated using the procedures described in Example 13. For comparison the bare (uncoated) ceramic spheres, converted on average 8.4% $CO_2$ at steady state, corresponding to $K_G$ of 0.0145 mmol/s-m²-kPa.

buffer as a substitute, showed a $K_G$ of 0.02 mmol/s·m²·kPa. A polysilicate/polysiloxane coating containing 3% enzyme by mass showed a $K_G$ of 0.05 mmol/s·m²·kPa, and a polysilicate/polysiloxane coating containing 6% enzyme by mass showed a $K_G$ of 0.09 mmol/s·m²·kPa. Higher enzyme loadings using materials produced using the procedure in Example 13 typically did not exceed a $K_G$ of 0.1 mmol/s·m²·kPa.

The role of 18-crown-6 on the observed $CO_2$ conversion capabilities of the coated ceramic packing was also investigated. Samples that contained no crown ether were hydrophobic and displayed activities of no more than 3× of uncoated ceramic.

In a separate study, 18-crown-6 ether was replaced with hydrophilic polymers including poly(vinyl alcohol) (PVA), poly(ethylene glycol) (PEG), and a poly quaternary ammonium (PQA) containing polymer (i.e., poly(diallydimethyl ammonium chloride)). These additives were used in similar molar ratios (i.e. monomer/additive) to that of 18-crown-6, and coated via the procedure described in Example 13. The resulting coated ceramics did not retain their high degree of enzymatic activity.

TABLE 2

SPR Analysis of Silica/Enzyme Coated Ceramic Spheres.

| Sample | Description | Type of Ceramic Used | % $CO_2$ Conversion | KG (mmol/ s · m² · kPa) | SPR Multiplier |
|---|---|---|---|---|---|
| 1 | PDMS550, TMOS, 18-Crown-6 6% Enzyme | 3 mm LW HF etched/OH funct. ceramic spheres | 57% | 0.09 | 5.28 |
| 1 | PDMS550, TMOS, 18-Crown-6 6% Enzyme | 3 mm BMR HF etched/OH funct. ceramic spheres | 60% | 0.11 | 6.00 |
| 2 | PDMS550, TMOS, 18-Crown-6 6% Enzyme | 3 mm BMR HF etched/OH funct. ceramic spheres | 48% | 0.11 | 6.47 |
| 3 | PDMS550, TMOS, 18-Crown-6 6% Enzyme | 3 mm BMR HF etched/OH funct. ceramic spheres | 42% | 0.07 | 4.63 |
| 4 | PDMS550, TMOS, 18-Crown-6 6% Enzyme | 3 mm BMR HF etched/OH funct. ceramic spheres | 52% | 0.09 | 4.44 |
| 5 | PDMS550, TMOS, 18-Crown-6 6% Enzyme | 3 mm BMR HF etched/OH funct. ceramic spheres | 46% | 0.07 | 3.69 |
| 6 | PDMS550, TMOS, 18-Crown-6 6% Enzyme | 3 mm BMR HF etched/OH funct. ceramic spheres | 39% | 0.06 | 2.95 |
| 7 | PDMS550, TMOS, 18-Crown-6 6% Enzyme | 3 mm BMR HF etched/OH funct. ceramic spheres | 41% | 0.06 | 3.17 |
| 8 | PDMS550, TMOS, 18-Crown-6 6% Enzyme | 3 mm BMR HF etched/OH funct. ceramic spheres | 50% | 0.08 | 4.14 |
| 9 | PDMS550, TMOS, 18-Crown-6 6% Enzyme | 3 mm BMR HF etched/OH funct. ceramic spheres | 41% | 0.06 | 3.11 |

The hydrophobic nature of the resulting silica enzyme coating typically makes a 24 hour hydration time insufficient for equilibration. Hydration times of 48 and 72 hours appear to convert $CO_2$ more effectively, presumably due to the better wetting observed in these systems.

Figure 10:
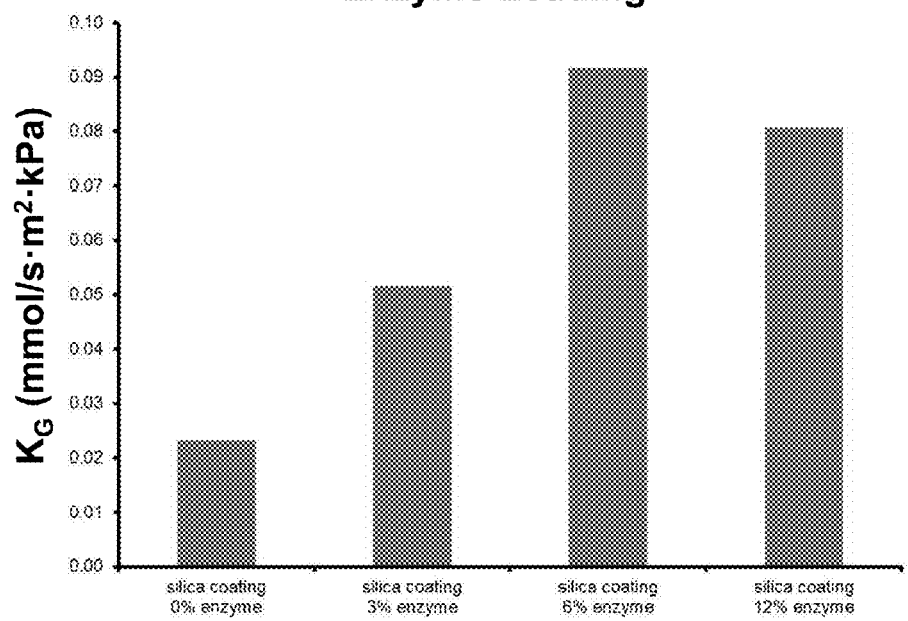
FIG. 10 is a graphical representation of the effect of carbonic anhydrase loading levels on the resulting enzymatic activity of coated supports prepared via Example 13.

FIG. 10, shows the effects of enzyme loading on activity. The loadings in FIG. 10 are reported as percentage of enzyme mass per mass of coating. The enzyme loadings in these samples were altered by decreasing the concentration of CA in phosphate buffer during the immobilization process. A sample prepared in the absence of enzyme, using phosphate Example 17

Coating Ceramic Spheres with Immobilized Carbonic Anhydrase in a Polysilicate/Polysiloxane Copolymer Containing 18-Crown-6 Through Surface-Initiated Catalysis Here catalysis with dissolved $NH_4F$ (i.e., adding catalyst directly to the monomer solution) is distinguished from surface-initiated catalysis, wherein the ceramics are pretreated with $NH_4F$ catalyst to induce deprotonation of the ceramic silanol functionalities.

In typical procedure, a 100 mL specimen cup, 65 g of ⅛" diameter ceramic spheres (Tipton Corp.) were soaked in 5.5 mL of a 91 mM aqueous $NH_4F$ solution for 5 minutes. After 5 minutes, the ceramics spheres were filtered onto a mesh screen.

Separately, a 600 mL beaker was charged with a mixture of tetramethyl orthosilicate (2200 μL, 14.9 mmol), silanol-terminated poly(dimethylsiloxane) (average $M_w$=550; 2200 μL), and 18-crown-6-ether (600 mg, 2.3 mmol). The mixture was sonicated for 5 minutes to homogenize.

Next, 1600 μL of stock A (as described in Example 1) were added to the reaction beaker and the resulting heterogeneous mixture was sonicated for 1 minute, or until a finely dispersed emulsion was observed.

Catalyst treated ceramic spheres (65 g) were then promptly added to the reaction beaker, and the mixture was subsequently stirred for 2 minutes with a metal spatula, or until gelation began to be observed.

After the onset of gelation, the coated ceramic was distributed onto a mesh screen and the spheres were evenly spaced to ensure contact was minimal prior to drying. The coated ceramic packing was allowed to dry for 15 minutes at room temperature. The drying and hydration method used was similar to that described in Example 13.

Example 18

Multiple Layer Deposition of Polysilicate-Polysilicone Copolymer Coatings onto Ceramic Spheres Through Surface Initiated Catalysis 65 g of ceramic spheres (Tipton Corp.) were treated with 5.5 mL of a 91 mM aqueous $NH_4F$ solution for 5 minutes and then transferred onto a mesh screen to dry.

Separately, a 600 mL beaker was charged with a mixture of tetramethyl orthosilicate (2200 μL, 14.9 mmol), silanol-terminated poly(dimethylsiloxane) (average $M_w$=550; 2200 μL), and 18-crown-6-ether (600 mg, 2.3 mmol). The mixture was sonicated for 5 minutes to homogenize.

Next, 1600 μL of stock A (as described in Example 1) were added to the reaction beaker and the resulting heterogeneous mixture was sonicated for 1 minute, or until a finely dispersed emulsion was observed.

Ammonium fluoride treated ceramic spheres (65 g) were then promptly added to the reaction beaker, and the mixture was subsequently stirred for 2 minutes with a metal spatula, or until gelation began to be observed.

The coated ceramic packing was allowed to dry for 15 minutes at room temperature.

After 15 minutes, the coated ceramic packing was again soaked in 5.5 mL of a 91 mM aqueous $NH_4F$ solution for 5 minutes and coated with a second layer of the sol mixture according to the aforementioned procedure. During the application of the second layer, the mixture was stirred at a slower rate to minimize sheer forces on the first layer. After the second layer was applied, the coated packing was dried at room temperature for 30 minutes. A third coating was then applied according to the previously described procedure. After application of the third coating, the mesh screens containing coated ceramic spheres were transferred to a vented oven and stored at 55° C. for 72 hours.

The mass of coating was calculated gravimetrically and used to calculate transfer efficiencies, film thickness, and amount of immobilized enzyme.

After obtaining the dry post-coating mass, 50 mL of buffer (0.8M/1.2M $K_2CO_3$/$KHCO_3$ buffer at pH=10.0) was added to the plastic container and the spheres were allowed to soak/equilibrate in solution for 68 hours.

The spheres were subsequently rinsed 3 times with water, followed by a replenishing of the 50 mL buffer (0.8M/1.2M $K_2CO_3$/$KHCO_3$ buffer at pH=10.0) solution. This washing procedure was repeated as many as three times before characterization and activity testing.

The enzyme/monomer/water ratio for the sol formulation shown above was 1:15:5, based on mass. This ratio could be easily altered by increasing or decreasing the amount of monomers (i.e., tetramethyl orthosilicate and poly(dimethylsiloxane)), or by increasing or decreasing the volume of enzyme stock solution added to the sol formulation. Furthermore, the ratio of monomers/hydrophilic additive, shown above to be 45:1 (based on moles) in the sol formulation, could be altered in a similar manner.

Example 19

Characterization of Ceramics with a Single Silica/Enzyme Coat Using Surface-Initiated Catalysis Samples prepared using the methods described in Example 18 showed higher coating masses and enzyme loadings than coatings containing only a single coat of silica/enzyme material.

The samples showed on average about 5.3 grams of mass added to the surface of the ceramic spheres. The mass of coating typically ranged from 4.8 g to 6.0 g of coating. The average CA loading on these was determined to be 6.3 g CA/L packing, using the methods described in Example 18. The CA loadings typically ranged from 5.0 to 7.0 g CA/L packing Characterization using SEM showed structural features similar to those shown in FIG. 9A-D.

Example 20

Activity Studies Utilizing Ceramics with a Multiple Silica/Enzyme Coats Using Surface-Initiated Catalysis To screen the activity of samples containing multiple coats of CA containing polysilicate/polysiloxane material a small scale single pass reactor, as described in Example 17, was utilized.

Figure 11:
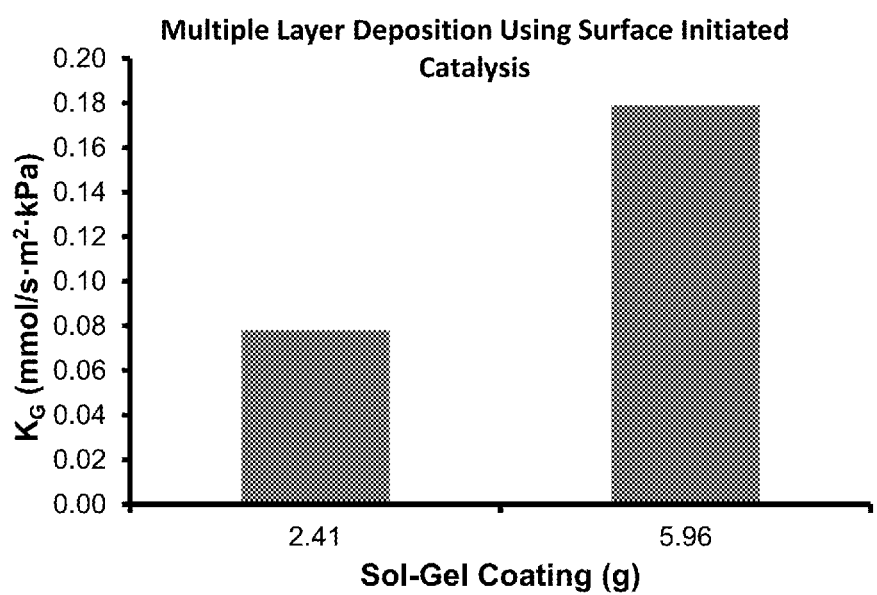
FIG. 11 is a graphical representation of the effect of the deposition of multiple polysilicate-polysilicone copolymer layers on the resulting enzymatic activity of coated supports generated using surface-initiated catalysis prepared via Example 18.

As shown in FIG. 11, increasing the mass of coating by utilizing a surface initiated catalysis resulted in samples that demonstrated exceptional capabilities for $CO_2$ conversion. A sample prepared using these methods, and containing 5.96 g of coating (approximately 6% enzyme), displayed a $K_G$ value of 0.18 mmol/s·m²·kPa, which corresponding to almost 80% conversion, and a 10-fold rate enhancement multiplier.

The above activity was recorded in a short term test (i.e., 30 minutes). To investigate the sustainability of this conversion and to identify the steady state conversion rate, a 24 hour test run was conducted in the SPR. These results are shown in FIG. 12.

Figure 12:
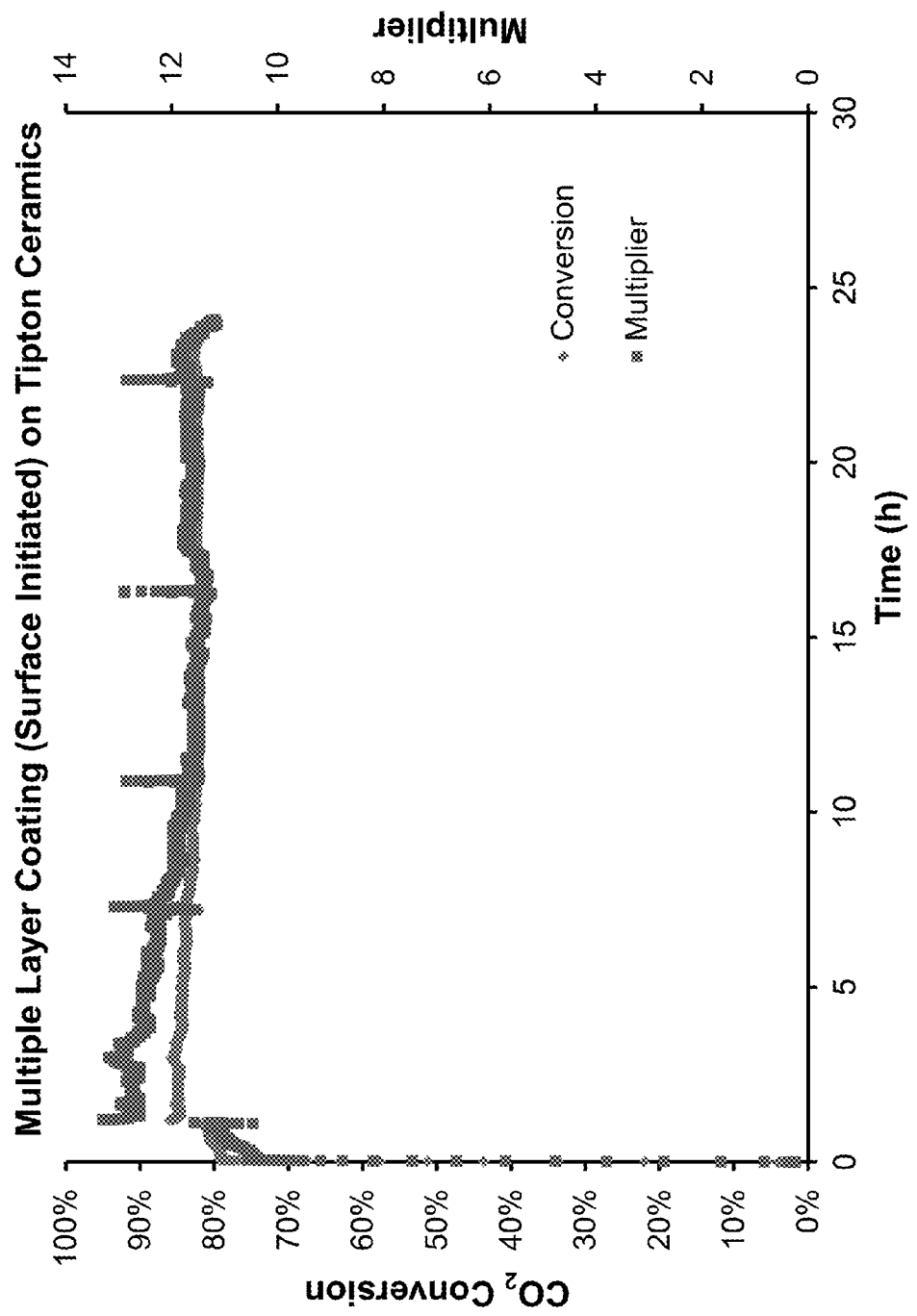
FIG. 12 is a graphical representation of the catalytic activity of coated Tipton supports, prepared according to the process outlined in Example 18, shown as percent $CO_2$ conversion and as the enhancement multiplier over the bare ceramic packing material.

The aforementioned sample showed an overall mass transfer coefficient ($K_G$) of 0.180 mmol/s·m²·kPa, corresponding to about 80% $CO_2$ capture, (see FIG. 12). This corresponds to an approximately 12.4 fold enhancement ($K_G$/$K_G$blank) over uncoated ceramic spheres ($K_G$=0.0145 mmol/s·m²·kPa). Sustained conversion rates of $CO_2$ were observed over run times up to 24 hours.

Example 21

Long-Term Activity Studies of Ceramic Spheres Coated with Polysilicate-Polysilicone Copolymers Using a Closed-Loop Continuous Flow Reactor This example tested the activity of coated solid supports for extended periods of time, under conditions in which the absorber solvent was regenerated via thermal stripping.

A closed-loop reactor (CLR) that operates under continuous flow was used. A schematic representation of the system is depicted in FIG. 2. The absorber column was a 78.5 cm tall, 5/8" internal diameter counter-flow column packed with ceramic spheres. The absorber solution was a 0.8M/1.2M $K_2CO_3$/$KHCO_3$ buffer at pH=10.0.

The solution in the absorber was circulated at a controlled rate of 20 mL/minute from the top of the column. A gas comprising 15% $CO_2$ (balanced with $N_2$) was flowed upwards from the bottom of the column (400 mL/minute). A thermal jacket was placed on the column to maintain a solution temperature of approximately 45° C. in the absorber.

Quantitation of $CO_2$ conversion was performed using a non-dispersive infrared detector (NDIR) monitoring the $CO_2$ gas at the output of the column. The differential between the $CO_2$ content of the output gas as compared to the feed gas was used to calculate the rate of absorption.

A sample of ceramic packing material, coated with three layers of polysilicate-polysilicone copolymer coating with carbonic anhydrase entrapped therein, was prepared according to the procedure set forth in Example 18. The activity of the sample was studied for 366 days in the CLR. The results of this analysis are presented in FIG. 13.

The sample showed an average conversion of 75% over the first 76 days, corresponding to an average $K_G$ of 0.143 mmol/s·m$^2$·kPa, and an average enhancement multiplier of 9.9 ($K_G$/$K_G$blank). The results obtained from the CLR study indicate that the amount of $CO_2$ converted by $1.19 \times 10^{-5}$ mol of CA over 100 days was 10.9 kg. This corresponds to a total turnover (moles $CO_2$/moles CA) of roughly 23.6 million.

After day 366 days it was calculated that the total turnover (moles $CO_2$/moles CA) of the above sample was roughly 58.9 million.

Example 22

Long-Term Enzyme Retention Study

A sample of ceramic packing material, coated with three layers of polysilicate-polysilicone copolymer coating with carbonic anhydrase entrapped therein, was prepared according to the procedure set forth in Example 18.

The sample was placed in a 78.5 cm tall, 5/8" internal diameter column packed with ceramic spheres. The absorber solution was a 0.8 M/1.2 M $KHCO_3$/$K_2CO_3$ solution (pH≈10), and was applied at a controlled rate (20 mL/minute) from the top of the column. The absorber solution was continuously cycled from a reservoir over the sample.

The enzyme loss (i.e., leaching) was measured over a 42 day period using UV-vis spectroscopic analysis against a prepared calibration curve. The amount of enzyme loss during the test period was calculated as percent loss. The results of this calculation are displayed in FIG. 14.

Figure 13:
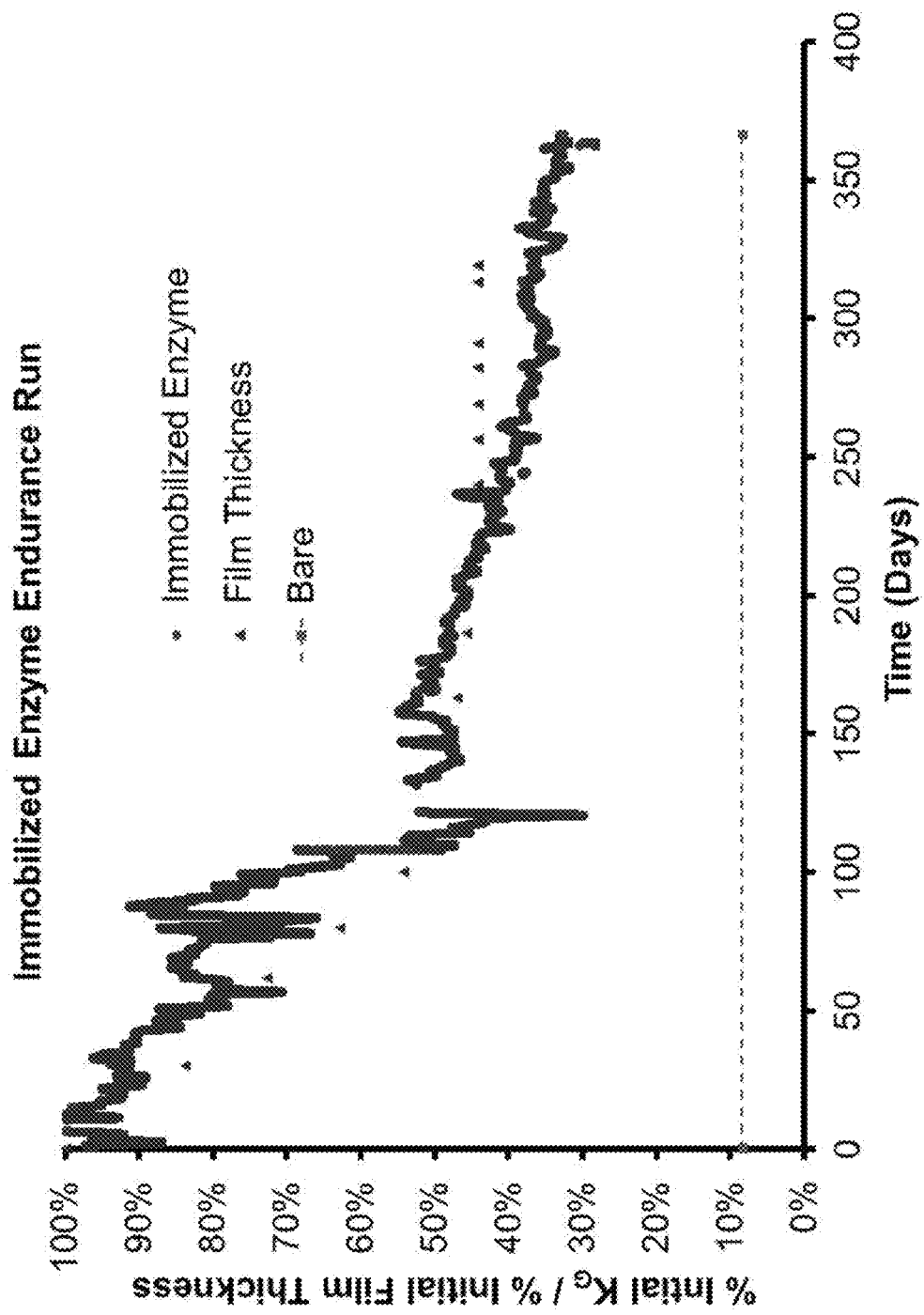
FIG. 13 shows the catalytic activity of coated supports and the coating thickness measured in a closed loop reactor over 366 days, as described in Example 18.
Figure 14:
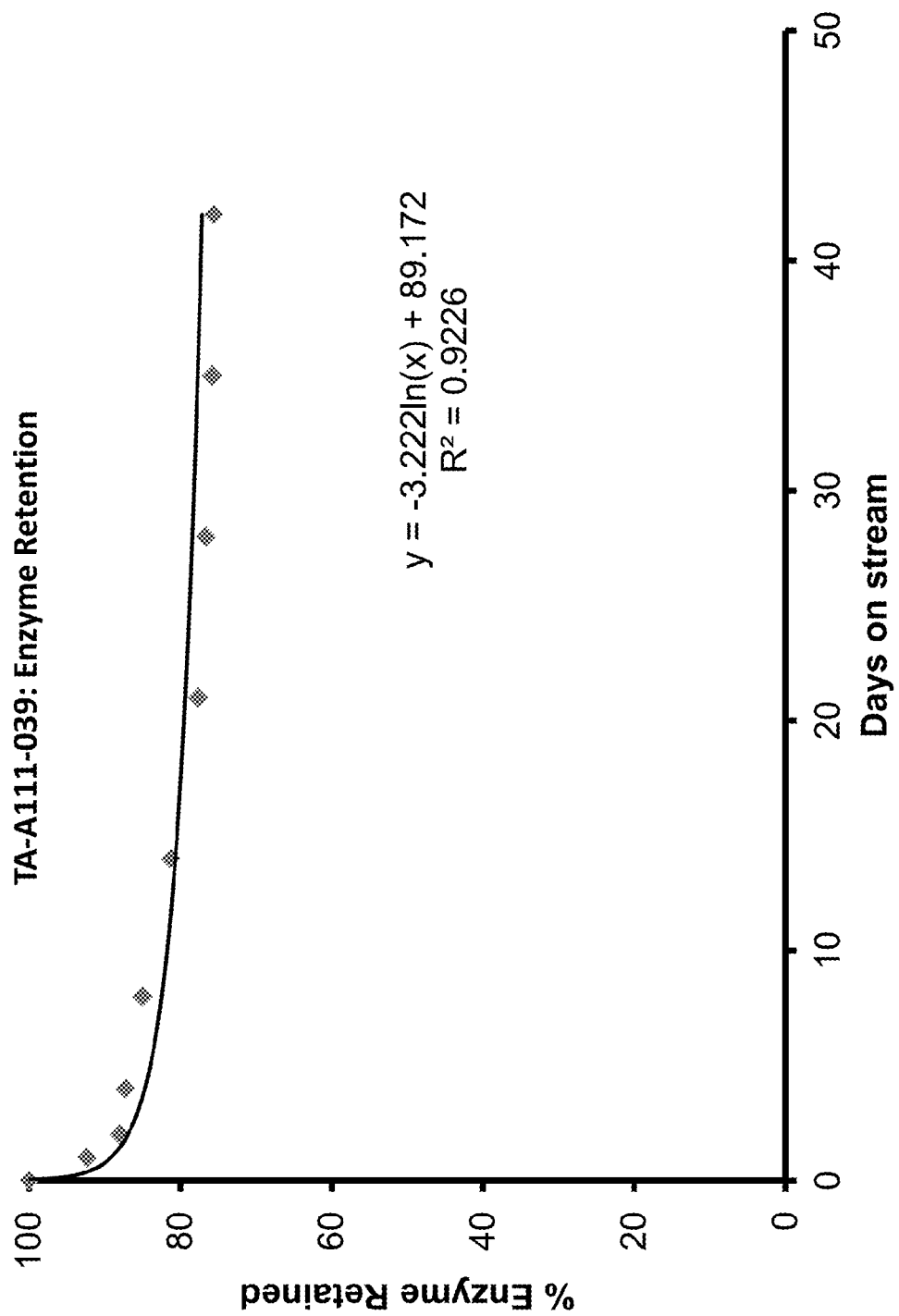
FIG. 14 is a graph showing the enzyme retention over time for a sample prepared according to Example 18 containing three coats of polysilicate-derived coating with entrapped carbonic anhydrase, as determined in a continuous flow environment for 42 days (as described in Example 18).

The results presented in FIGS. 13 and 14 clearly demonstrate that the biocatalytic coatings described in this application sustain $CO_2$ conversion and enzyme retention for exceptionally long periods of time.

Example 23

Activity Studies of Ceramic Spheres Coated with Polysilicate-Polysilicone Copolymers in the Presence of Trace Contaminants of $SO_2$ and $NO_2$ A sample of ceramic packing material, coated with three layers of polysilicate-polysilicone copolymer coating with carbonic anhydrase entrapped therein, was prepared according to the procedure set forth in Example 18.

A 70 mL column was packed with immobilized enzyme deployed as a polysilicate/polysiloxane coating on 3.6 mm Tipton spherical packing with a 0.4 SLPM gas flow.

Figure 15:
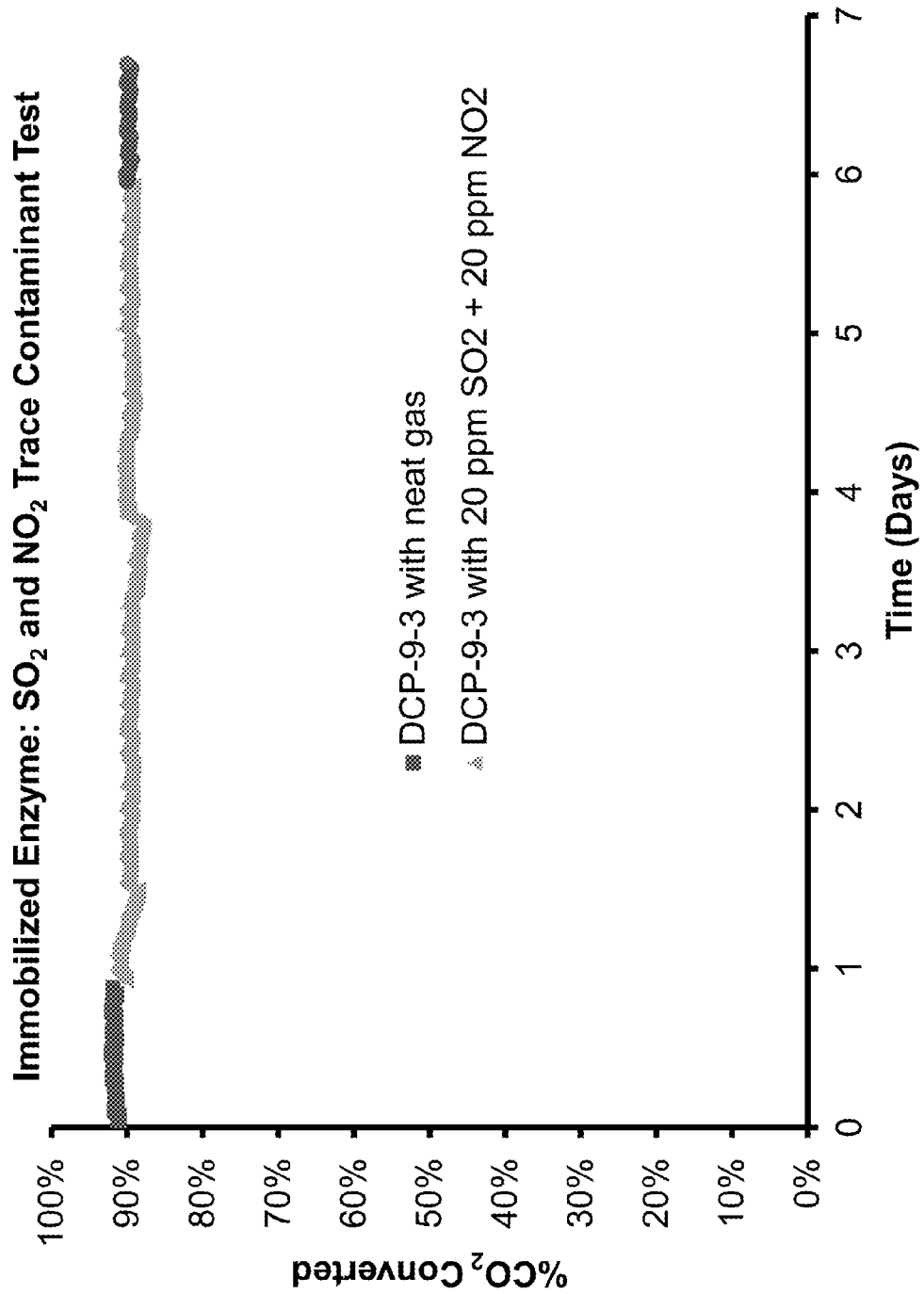
FIG. 15 is a graph showing the catalytic activity of a coated support prepared according to Example 18 in the presence of trace contaminants of $SO_2$ and $NO_2$.

The initial gas feed was 15% $CO_2$ balanced by nitrogen (FIG. 15; shown in the first blue trace over ~1 day).

The feed gas was then switched to a 15% $CO_2$ blend with 20 ppm $NO_2$ and 20 ppm $SO_2$, balanced by nitrogen.

The performance of the sample with this feed gas is shown in the green trace of FIG. 15 over a 5 day period.

The feed gas was then switched back to the original 15% $CO_2$ (balanced by nitrogen), which is shown in the final blue trace of FIG. 15 (~day 6 to 7).

This result demonstrates the lack of inhibition of the immobilized carbonic anhydrase in the presence of trace $NO_2$ and $SO_2$, which are present in post combustion flue gas.

Example 24

Activity Studies of Ceramic Spheres Coated with Polysilicate-Polysilicone Copolymers Using Coal Fired Flue Gas Two samples of ceramic packing material, coated with three layers of polysilicate-polysilicone copolymer coating with carbonic anhydrase entrapped therein, were prepared according to the procedure set forth in Example 18.

The test unit consisted of a 5/8" i.d. absorber column containing immobilized enzyme coated on 3.6 mm Tipton ceramic spherical packing operating at 200 sccm gas flow.

The potassium carbonate solvent maintained constant feed pH of ~10 using a 3" diameter air stripper bubble column operating between 2 SLPM and 5 SLPM at room temperature.

The combustion gases were derived from a Wyoming Powder River Basin subbituminous coal and fed to the unit after bag-house filtration and moisture condensation and knock-out.

Mercury content was measured to be 3.06 μg/m$^3$ of total Hg content with 1.07 μg/m$^3$ being in the form of Hg$^{+2}$ and 1.99 μg/m$^3$ being in the form of Hg$^0$.

The $CO_2$ composition of the flue gas averaged ~13.9% over the duration of the experiment.

The two replicate coated samples of Tipton were used to compare performance on flue gas with reference test with a bottled clean gas mixture. Both tests were analyzed under identical operating conditions (i.e., 200 sccm feed gas).

Figure 16:
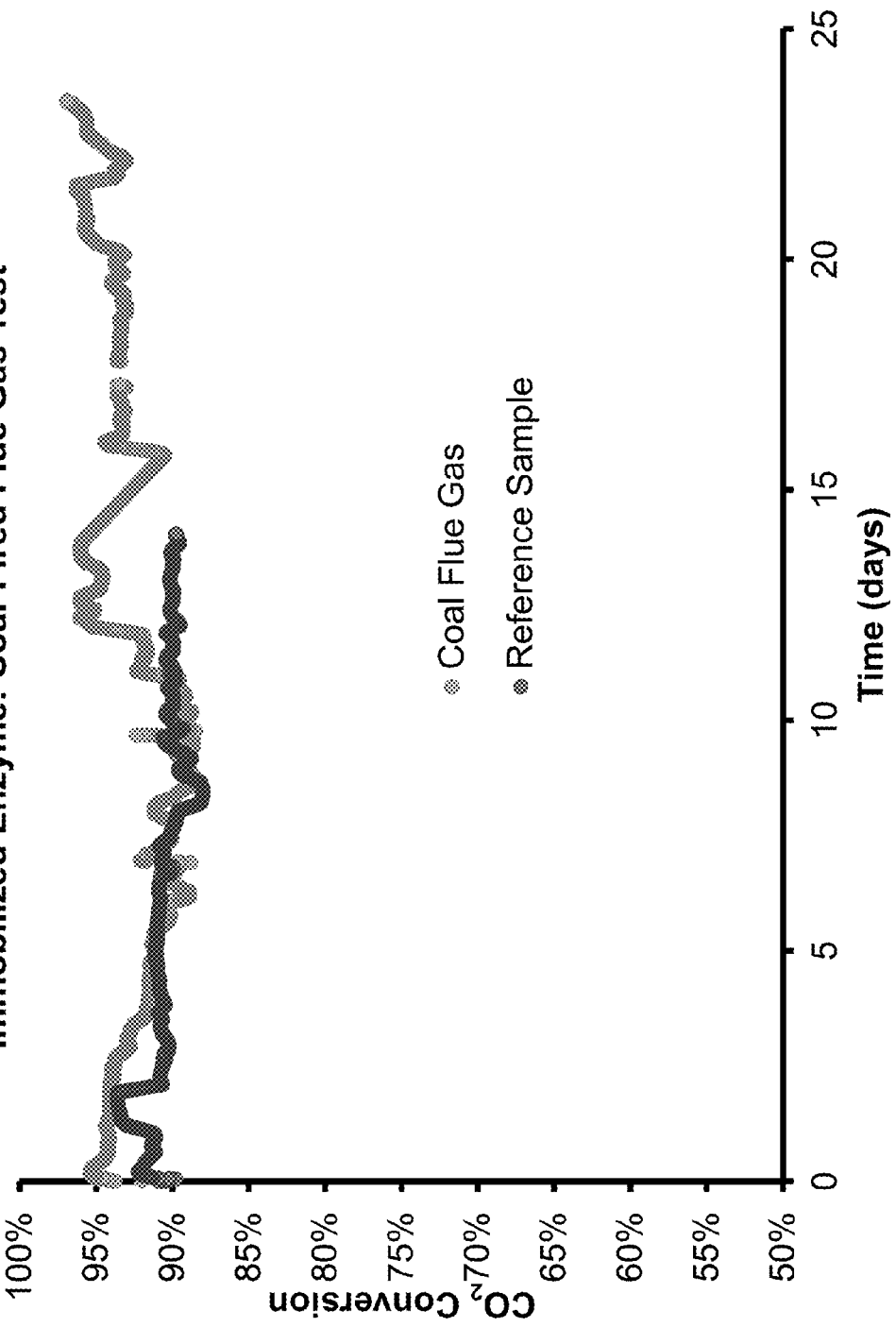
FIG. 16 is a graph showing the catalytic activity of a coated support prepared according to Example 18 using coal fired flue gas.

As can be seen in FIG. 16, the sample subjected to flue gas performed as well as the reference sample over the entire course of the experiment capturing between 90% and 95% of the $CO_2$ feed.

Example 25

Treatment of Sulzer Structured Packing with a Silicate Primer Layer

Similar to previously described literature procedures for treating stainless steel with tetraethylorthosilicate, a 500 mL pyrex bottle is charged with 97.5 mL of ethanol, 97.5 mL of tetraethylothosilicate, and 13.7 mL of 2M $NH_4OH$.

The reaction mixture is aged for a minimum of 30 minutes, during which time a colloidal suspension becomes evident.

The mixture above is spray coated onto 7 units of 2" column diameter Sulzer Mellapak® 500X structured packing The scale can be altered to accommodate packing material with different column diameters and more or less surface area.

After the spray coating, the sample is dried at room temperature for 30 minutes then cured at elevated temperature with a ramping process of 60° C.-350° C. over the course of two hours, one hour at 450° C., and finally an hour ramp from 550° C. to 650° C.

After the curing, the coating is cooled to room temperature and then washed gently.

The process is repeated two more times and dried before use.

Example 26

Spray Coating of Sulzer Structured Packing Using Methanol Dilution to Prepare the Polysiloxane/Polysilicate Coating Containing Immobilized Carbonic Anhydrase Three units of Sulzer Mellapak® 500X, 2" column diameter, structured packing were pretreated with tetraorthosilicate to provide a primer layer according to Example 25.

In some cases the packing is soaked in 100 mM $NH_4F$ and dried prior to deposition of the polysiloxane/polysilicate immobilization material. In some cases this pretreatment is not used.

A 400 mL beaker is charged with 16.2 mL of a 150 mg/mL solution of carbonic anhydrase (as described in Example 1) and 675 mg of CTAB. In some cases the CTAB is not used. The contents are mixed via magnetic or mechanical mixing until the CTAB is fully dissolved.

While under vigorous stirring a monomer solution containing tetramethylorthosilicate (17.5 mL; 118 mmol), silanol-terminated polydimethylsiloxane (14.8 mL; 26 mmol), and 18-crown-6 (4.05 g) is slowly added and the mixing rate is increased. Blends of alkyl-trimethoxysilanes and PEG-derived trialkoxysilanes have also been generated using similar methods.

Once the mixture forms a well dispersed emulsion (water in oil) 63.5 mL of methanol is added to the beaker, immediately followed by 74 µL of $NH_4F$ catalyst. The mixture is then stirred vigorously for 6 minutes and 15 seconds. The mixing time can change readily based on the amount of catalyst used and the scale of the reaction.

The coating solution is then transferred to a high volume low pressure (HVLP) spray gun (Aeropro, G6600-25) operated at 40 psi and deposited onto the structured packing Other types of spray guns can be utilized. Also, a mixture of this nature can also be deposited through dip, roll, or flow coating.

During the coating process, the structured packing material can be laid out in sheets either horizontally or hung vertically on hooks.

After coating, the sample is coated it is dried at room temperature for 30 minutes to 1 hour. The sample is then transferred to a 55° C. for one hour and then the temperature is ramped to 75° C. for two hours. Different curing temperatures and times can be utilized. The method described here has led to optimal activity results.

After deposition of the first coat, the same formulation increased 1.5 times in scale was used to deposit a second coat using the same methods and curing procedure. The need for multiple coats, and the volume of spray solution utilized, can be determined based on desired performance and film thickness. The use of three coats has provided optimal performance in the test systems described herein.

After the second coat, the same formulation increased 2 times in scale was used to deposit a third coat using the same methods.

After the third coat, the sample is cured at 55° C. for 24 hours and then 75° C. for 72 hours. Again, different variations of curing times can be utilized as needed for specific applications.

After the final cure the individual units of Sulzer Mellapak® 500X, 2" column diameter, packing are washed and hydrated via immersion in excess aqueous buffer for 48 to 96 hours. Typically, immersion in 0.8M/1.2M $K_2CO_3/KHCO_3$ buffer at pH=10.0 for 72 hours is utilized however, different aqueous buffers, pH's, and hydration times could be utilized as needed.

During, or after, the washing hydration process aliquots are removed from the soaking solution and the enzyme in solution is quantitated to determine enzyme retention of the immobilization matrix.

After sufficient hydration, the sheets were assembled into a complete 2" diameter structured packing section by wrapping with wiper bands and spot welding them into place. The sample was then analyzed in one of several reactors equipped with 2" absorber columns.

The enzyme/monomer/water ratio for the sol formulation shown above was 1:15:5, based on mass. This ratio could be easily altered by increasing or decreasing the amount of monomers (i.e., tetramethyl orthosilicate and poly(dimethylsiloxane)), or by increasing or decreasing the volume of enzyme stock solution added to the sol formulation. Furthermore, the ratio of monomers/hydrophilic additive, shown above to be 45:1 (based on moles) in the sol formulation, could be altered in a similar manner.

This procedure has also been used to coat Sulzer Mellapak® 500X and has also been deposited on top of other primer coatings including ceramic based primer coatings.

Example 27

Spray Coating of Sulzer Structured Packing Using Ethanol Dilution to Prepare the Polysiloxane/Polysilicate Coating Containing Immobilized Carbonic Anhydrase In a typical procedure, a 1 L flat flange reaction flask was charged a 7.2 mL of a 150 mg/mL stock A solution of carbonic anhydrase (as described in Example 1).

To this enzyme solution, 0.30 g of cetyl trimethylammonium bromide (CTAB, 0.8 mmol) was added and stirred with a magnetic stir bar or mechanical stirrer to fully dissolve.

Next a monomer solution containing tetramethyl orthosilicate (7.8 mL, 52 mmol), silanol-terminated poly(dimethyl siloxane) (average $M_w$=550; 6.6 mL) and 18-crown-6-ether (1.8 g, 6.6 mmol) was added under vigorous stirring.

Upon effective dispersion and subsequent emulsion formation, 9.0 mL of 0.1 M $NH_4F$ was added to the stirring mixture. The mixture began to turn opaque immediately, and 27 mL of reagent alcohol (90% ethanol, 5% methanol, 5% isopropanol) was quickly added under vigorous stirring.

After 10-15 seconds, this mixture began to thicken, and a second aliquot of 7.5 mL of reagent alcohol was added with stirring to facilitate transfer of the mixture.

This mixture was then divided in half by volume. Half was transferred to a high volume low pressure (HVLP) spray gun (Aeropro, G6600-25) operated at 40 psi. The entire contents of the spray gun hopper were sprayed onto one side of a 8.75" length section of stainless steel structured packing (Sulzer Mellapak® 500X, 2" column diameter) laid out in sheets either horizontally or hung vertically on hooks.

This polysilicate-polysilicone coating was allowed to dry at room temperature for 20 minutes and then the sheets were flipped over and sprayed with the other half of the mixture.

This coating was allowed to dry at room temperature for 30 minutes and then placed in a 55° C. oven to dry for 1 hour. A second coat was added following the above procedure at 1.5 times scale up of every reagent.

A third (and final coat) was added following the above recipe at 2.0 times scale up of every reagent. After both sides of the packing were sprayed, the coating was allowed to dry at room temperature for 30 minutes and then placed in a 55° C. oven to dry/cure overnight. It was then transferred to 75° C. oven to cure for 72 hours.

An alternative curing cycle investigated that utilized drying at room temperature overnight after coats 1 and 2, sometimes with an hour at 55° C. the following morning, before adding the next coat. After the $3^{rd}$ (final) coat, the sample dried at room temperature overnight, followed by 72 hours at 75° C. Other variations in drying times and temperatures have also been successfully employed.

After completing the curing cycle, the sheets were removed from the oven and placed into a known volume of 0.8M/1.2M $K_2CO_3$/$KHCO_3$ buffer at pH=10.0 to hydrate and placed in an incubator at 45° C. for at least 3 days. Hydration could also be accomplished at other temperatures, including room temperature, and times, but here 45° C. for at least 3 days is preferred.

Aliquots were taken from this storage solution periodically to assess enzyme retention.

After sufficient hydration, the sheets were assembled into a complete 2" diameter structured packing section by wrapping with wiper bands and spot welding them into place. The sample was then analyzed in one of several reactors equipped with 2" absorber columns.

This procedure has also been used to coat Sulzer Mellapak® 500X with a 4" column diameter and 8" column diameter, and has also been deposited on top of other primer coatings including ceramic-based primer coatings.

Example 28

Activity Studies Utilizing Silica/Enzyme Coated Sulzer Mellapak® 500X Structured Packing The activities of coated Sulzer Mellapak® 500X samples with a 2" column diameter were tested in two separate systems, closed loop reactor, CLR and structured packing test stand (SPTS).

The closed loop reactor system, which is shown in FIG. 2 and the operating conditions are described in Example 21, was used in this testing. Alterations were made to accommodate the 2" structured packing, including using a column that was 91.4 cm tall with a 2" in. diameter. A thermal jacket was placed on the column to maintain a solution temperature of approximately 45° C. in the absorber. All samples tested in the CLR were done so at 45° C.

Typical operating conditions in the CLR for a single section of 2" structured packing were as follows; the absorber solution (45° C.) was pumped at a controlled rate (218 mL/minute) from the top of the column. A gas comprising 15% $CO_2$ (balanced with $N_2$) moved upwards from the bottom of the column (2.18 SLPM). SPTS has the capability for continuous closed loop testing of up to four ~2" diameter structured packing absorption columns or one ~4" structured packing absorption column. The SPTS utilizes heated air stripping for solvent regeneration.

The absorber column in the SPTS was 106.6 cm tall with a 2⅛ in. internal diameter counter-flow column packed with 2" structure packing A column that was 106.6 cm tall with a 3.95 in. internal diameter was used for 4" structured packing samples. The absorber solution was a 0.8M/1.2M $K_2CO_3$/$KHCO_3$ buffer at pH=10.0.

All tests in SPTS system were done at room temperature.

The liquid and gas flow rates for 2" structured packing were the same as those described above. The liquid and gas flow rates for 4" structured packing were as follows; the absorber solution was pumped at 1200 mL/minute and gas was flowed upwards from the bottom of the column at 8 SLPM.

Quantitation of $CO_2$ conversion in both systems was performed using a non-dispersive infrared detector (NDIR) monitoring the $CO_2$ gas at the output of the column. The differential between the $CO_2$ content of the output gas as compared to the feed gas was used to calculate the rate of absorption.

Table 3 shows the activity of samples prepared according to Examples 26 and 27 tested in the SPTS. The samples, on average, proved capable of converting 70% $CO_2$ with an average $K_G$ of 0.133 mmol/s-$m^2$-kPa. Comparison to the bare (uncoated) Sulzer Mellapak® 500X samples with a 2" column diameter, which converted on average 14% $CO_2$ with a $K_G$ of 0.0118 mmol/s-$m^2$-kPa, provided an average rate constant multiplier of 11.19, a measurement used to determine efficacy of the coating in converting $CO_2$.

TABLE 3

Analysis of Silica/Enzyme Coated Sulzer Mellapak ® 500X samples with a 2" column diameter in the SPTS.

| Sample ID | Dilutant | % Enzyme Retained | Total Enzyme In Reactor (g) | Estimated CA Loading on Packing (g CA/ L packing) | $K_G$ (mmol/ s·$m^2$·kPa) | $CO_2$ Conversion (%) | Multi- plier |
|---|---|---|---|---|---|---|---|
| 1 | Ethanol | 70% | 0.996 | 1.898 | 0.129 | 74% | 10.92 |
| 2 | Methanol | 96% | 2.992 | 5.699 | 0.123 | 68% | 10.42 |
| 3 | Methanol | 91% | 2.627 | 5.003 | 0.135 | 72% | 11.45 |
| 4 | Methanol | 94% | 3.227 | 6.147 | 0.145 | 72% | 12.3 |

TABLE 3-continued

Analysis of Silica/Enzyme Coated Sulzer Mellapak ® 500X samples with a 2" column diameter in the SPTS.

| Sample ID | Dilutant | % Enzyme Retained | Total Enzyme In Reactor (g) | Estimated CA Loading on Packing (g CA/ L packing) | $K_G$ (mmol/ s·m²·kPa) | $CO_2$ Conversion (%) | Multiplier |
|---|---|---|---|---|---|---|---|
| 5 | Methanol | 89% | 2.71  | 5.161 | 0.113 | 63% | 9.6   |
| 6 | Ethanol  | 78% | 1.208 | 2.301 | 0.131 | 73% | 11.13 |
| 7 | Methanol | 86% | 2.589 | 4.931 | 0.144 | 73% | 12.2  |
| 8 | Ethanol  | 75% | 1.581 | 3.011 | 0.135 | 68% | 11.5  |

Figure 17:
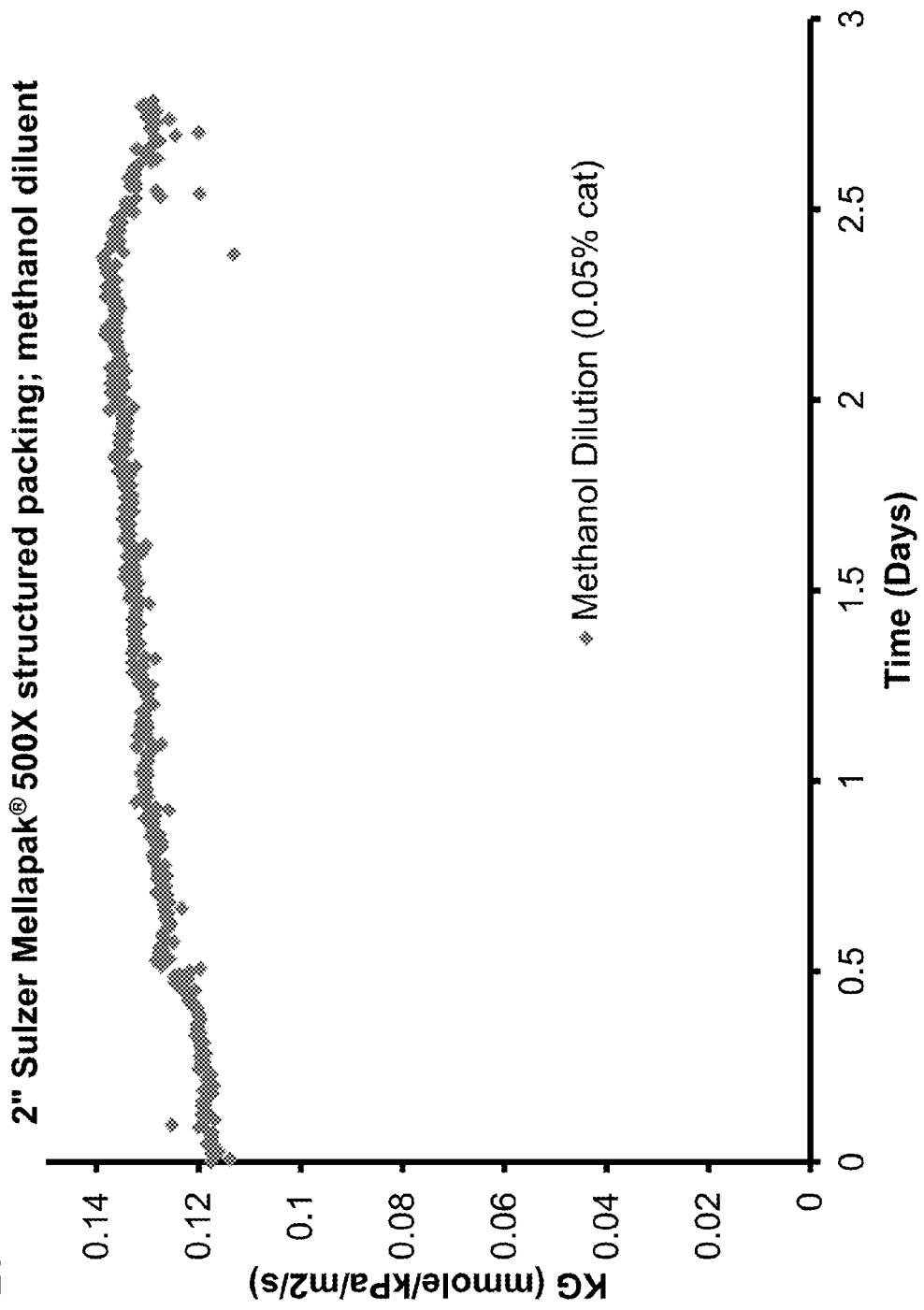
FIG. 17 shows the $K_G$ of a coated 2" Sulzer packing unit coated using the formulation and methods described in Example 26.

To test the activity of coated Sulzer Mellapak® 500X samples with a 2" column diameter over extended periods of time, typically the CLR reactor was utilized. In FIG. 17 a 2" coated sample prepared according to Example 26 was analyzed for 3 days in the CLR. The resulting sample showed an average $K_G$ of 0.12 mmol/s-m²-kPa during this time period.

Figure 18:
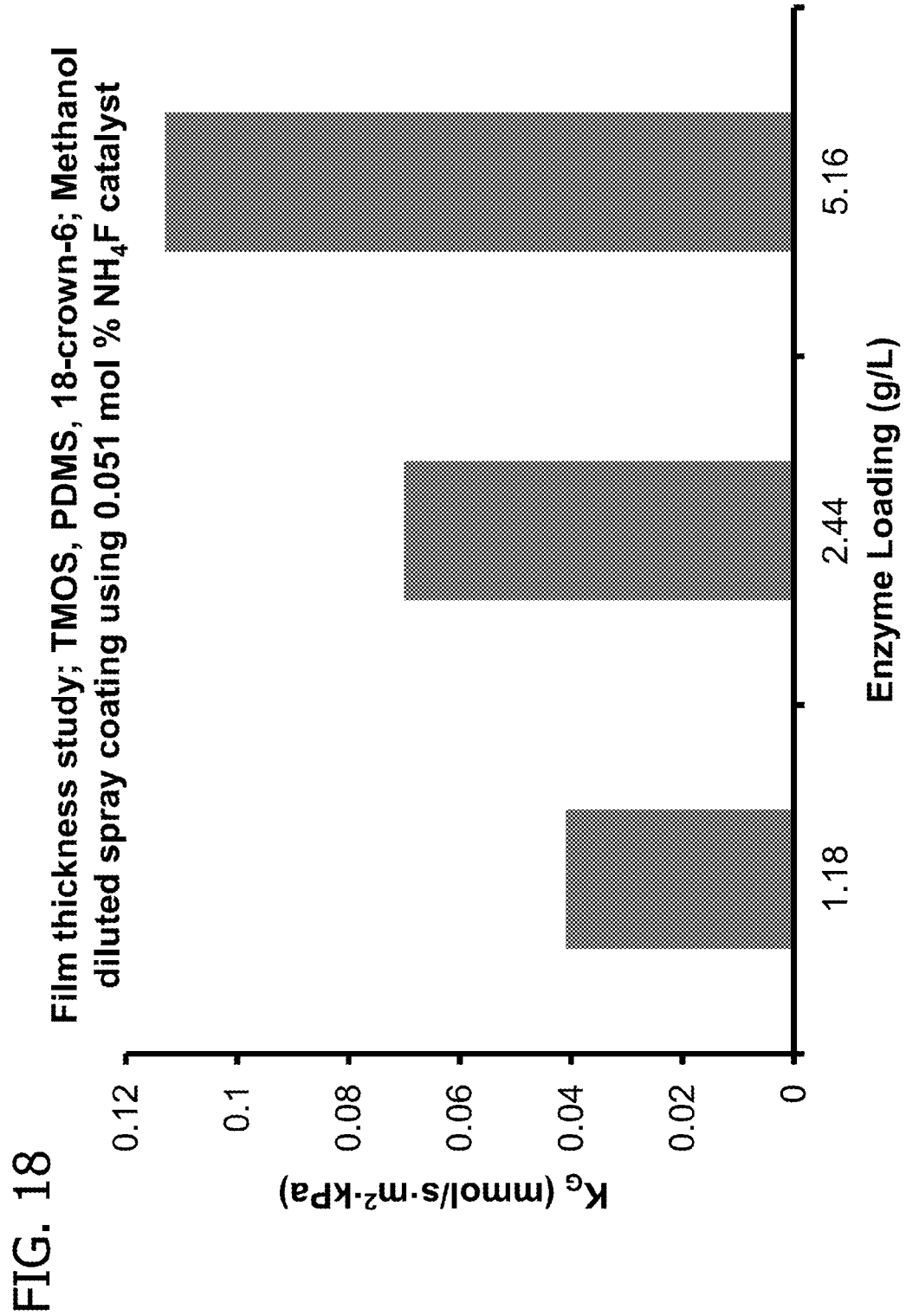
FIG. 18 shows a coating thickness study (described as mass) of 2" Sulzer structured packing material coated using the formulation and methods described in Example 26 utilizing 0.051 mol % of $NH_4F$ catalyst.

To test the correlation between $CO_2$ conversion and enzyme loading (film thickness) three samples were prepared in a procedure similar to that described in Example 26 using 0.051% catalyst (molar ratio of catalyst to reactive monomers (TMOS and PDMS)). The samples contained single coat of the silica/enzyme immobilization matrix (1.18 g of CA/L reactor volume), two coats (2.44 g of CA/L), and three coats (5.16 g of CA/L) respectively. As shown in FIG. 18, the sample activity increased as the enzyme loading in the sample increased.

Figure 19:
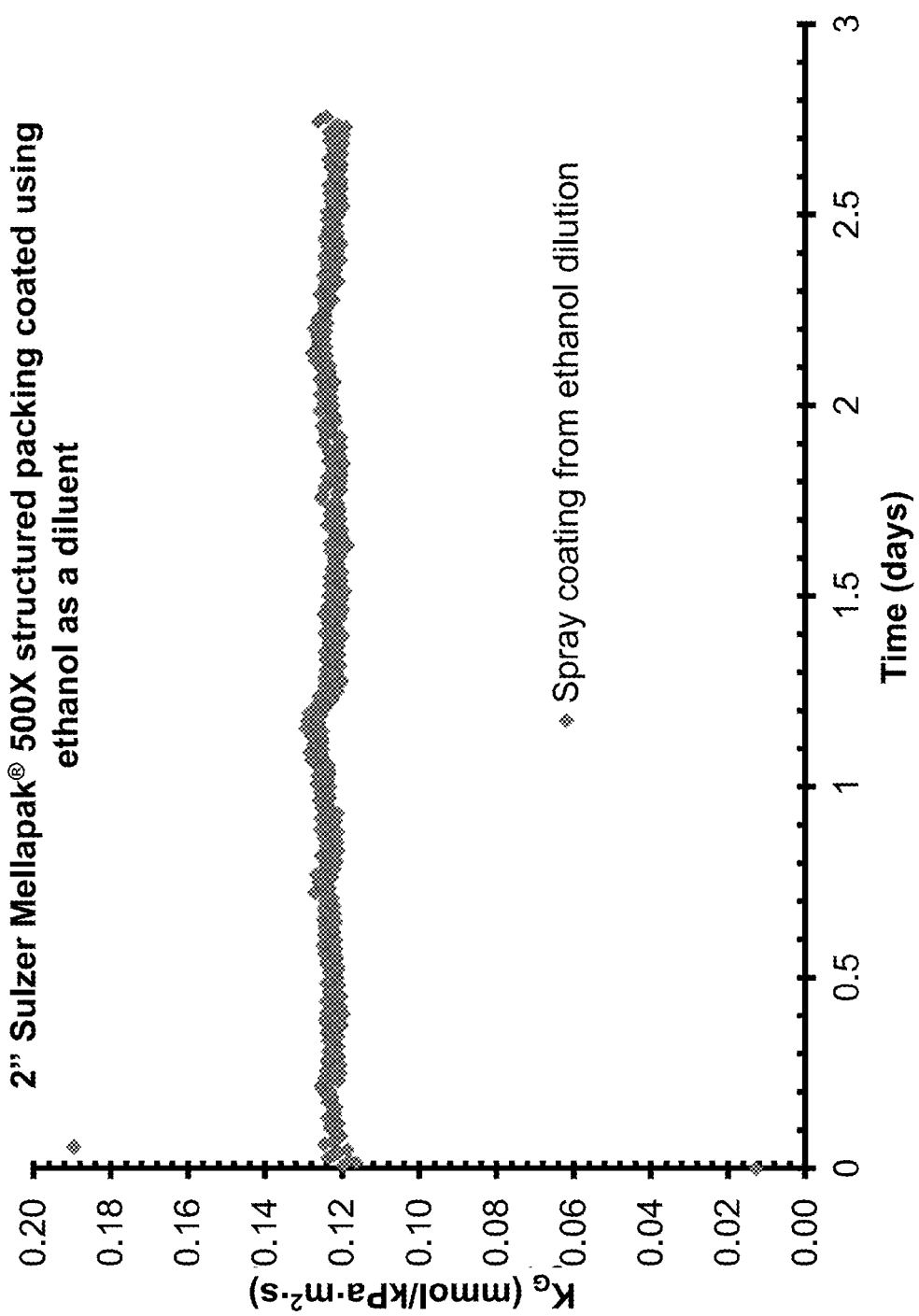
FIG. 19 shows the $K_G$ of a 2" Sulzer packing unit coated using the formulation and methods described in Example 27.

In FIG. 19 a 2" coated sample prepared according to Example 27 was analyzed for 3 days in the CLR. The showed a sustained $K_G$ of 0.12 mmol/s-m²-kPa over the course of three days. The sample showed negligible decrease in performance over this time period.

Example 29

Coating Sulzer Mellapak® 500X with a 2" Column Diameter Using Epoxy Adhesives to Adhere Porous Xerogel Powders In a typical procedure, 100 g of a 2-part epoxy (Pro-Poxy 200) was prepared and added to a shallow trough.

This epoxy was diluted with methanol (75 mL) and mixed thoroughly to homogenize. Individual sheets of a 8.75" length section of stainless steel structured packing (Sulzer Mellapak® 500X, 2" column diameter, 7 sheets total) were dipped in the diluted epoxy mixture and then dusted with one of the xerogel powder, prepared according to Example 1 using a <500 micron diameter sieve, to completely cover the epoxy layer.

The xerogel powder loading on the sample was determined by the mass difference of xerogel powder before and after the coating process.

This method has been used to adhere representative powders from Examples 1, 3, and 7 to the surface of stainless steel structured packing and ceramic random packing materials.

The sheets were then hung up on hooks in the hood to dry at room temperature for 3 hours and then transferred to a 55° C. oven to cure the epoxy overnight.

After completing the curing cycle, the sheets were removed from the oven and placed into a known volume of 0.8M/1.2M $K_2CO_3$/$KHCO_3$ buffer at pH=10.0 to hydrate for at least 3 days.

Aliquots were taken from this storage solution periodically to assess enzyme retention.

After sufficient hydration, the sheets were assembled into a complete 2" diameter structured packing section by wrapping with wiper bands and spot welding them into place.

The sample was then analyzed in one of several reactors equipped with 2" absorber columns.

Example 30

Activity Testing of Sulzer Mellapak® 500X Samples with a 2" Column Diameter Coated Using Epoxy Adhesives to Adhere Porous Xerogel Powders In some cases, the CLR was utilized to test the activity of coated Sulzer Mellapak® 500X samples with a 2" column diameter coated using epoxy adhesives to adhere porous xerogel powders according to the methods described in Example 29.

Figure 20:
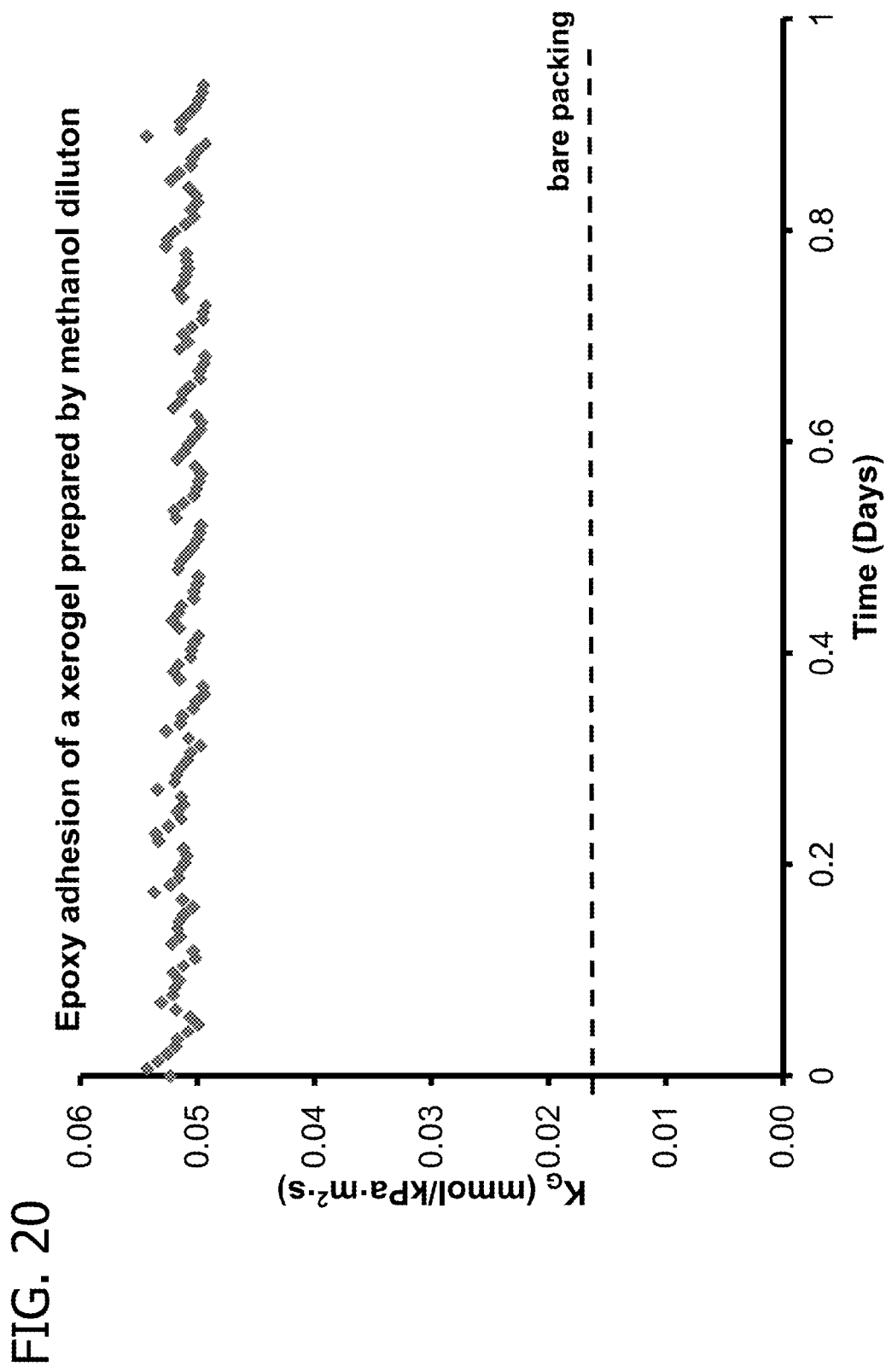
FIG. 20 shows the $K_G$ of a 2" Sulzer packing unit coated using the adhesive method described in Example 29 produced using a xerogel powder prepared using methanol dilution according to Example 3.

In FIG. 20, a xerogel powder prepared according to the experimental procedure described in Example 3 was adhere to Sulzer packing using epoxy adhesive and tested for activity in the CLR. The sample showed an average $K_G$ of 0.051 mmol/s-m²-kPa, corresponding to a 3.2 fold enhancement over the blank.

Figure 21:
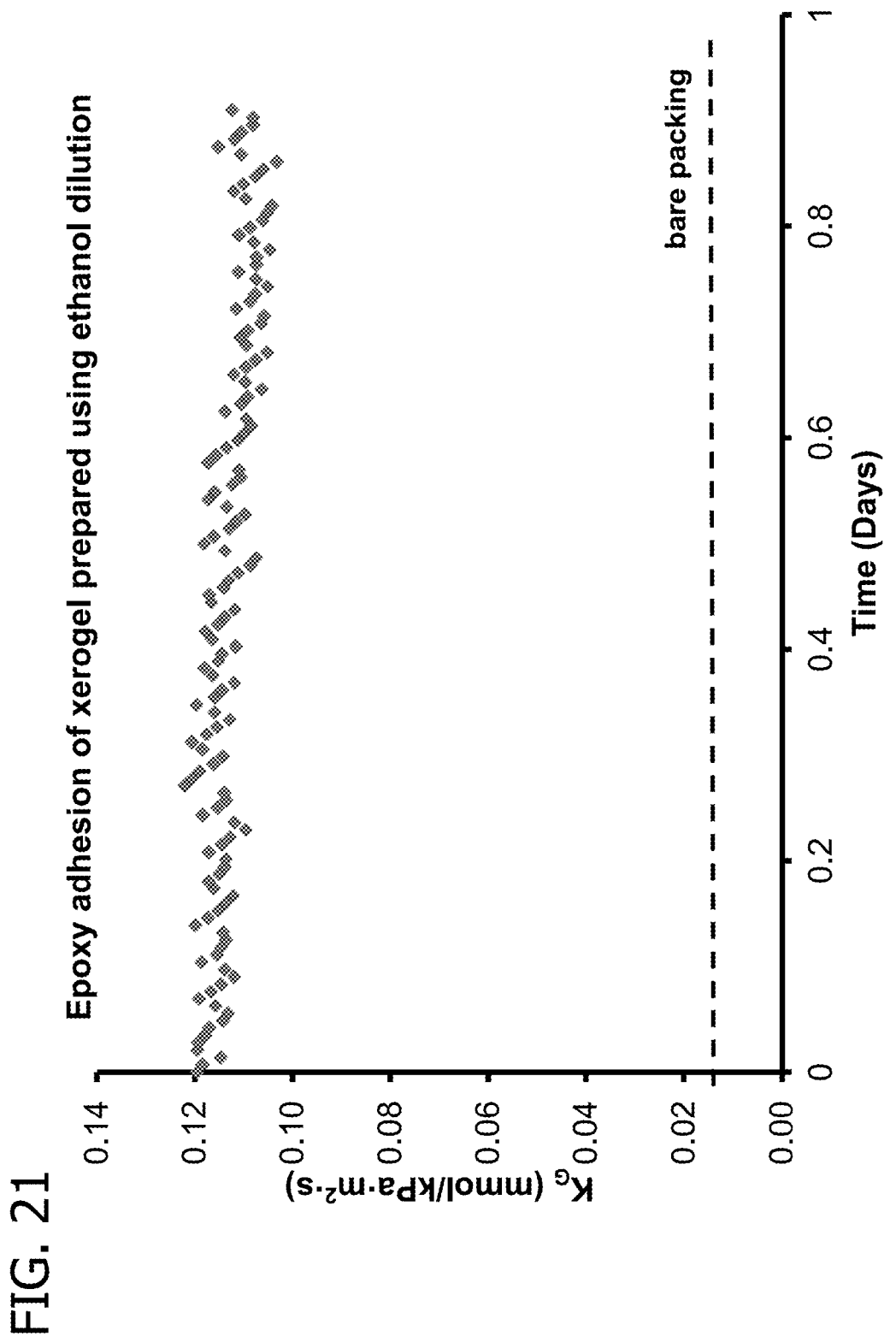
FIG. 21 shows the $K_G$ of a 2" Sulzer packing unit coated using the adhesive method described in Example 29 produced using a xerogel powder prepared using ethanol dilution according to Example 7.

In FIG. 21, a xerogel powder prepared according to the experimental procedure described in Example 7 was adhere to Sulzer packing using epoxy adhesive and tested for activity in the CLR. The sample showed an average $K_G$ of 0.113 mmol/s-m²-kPa, corresponding to a 7.1 fold enhancement over the blank.

Figure 22:
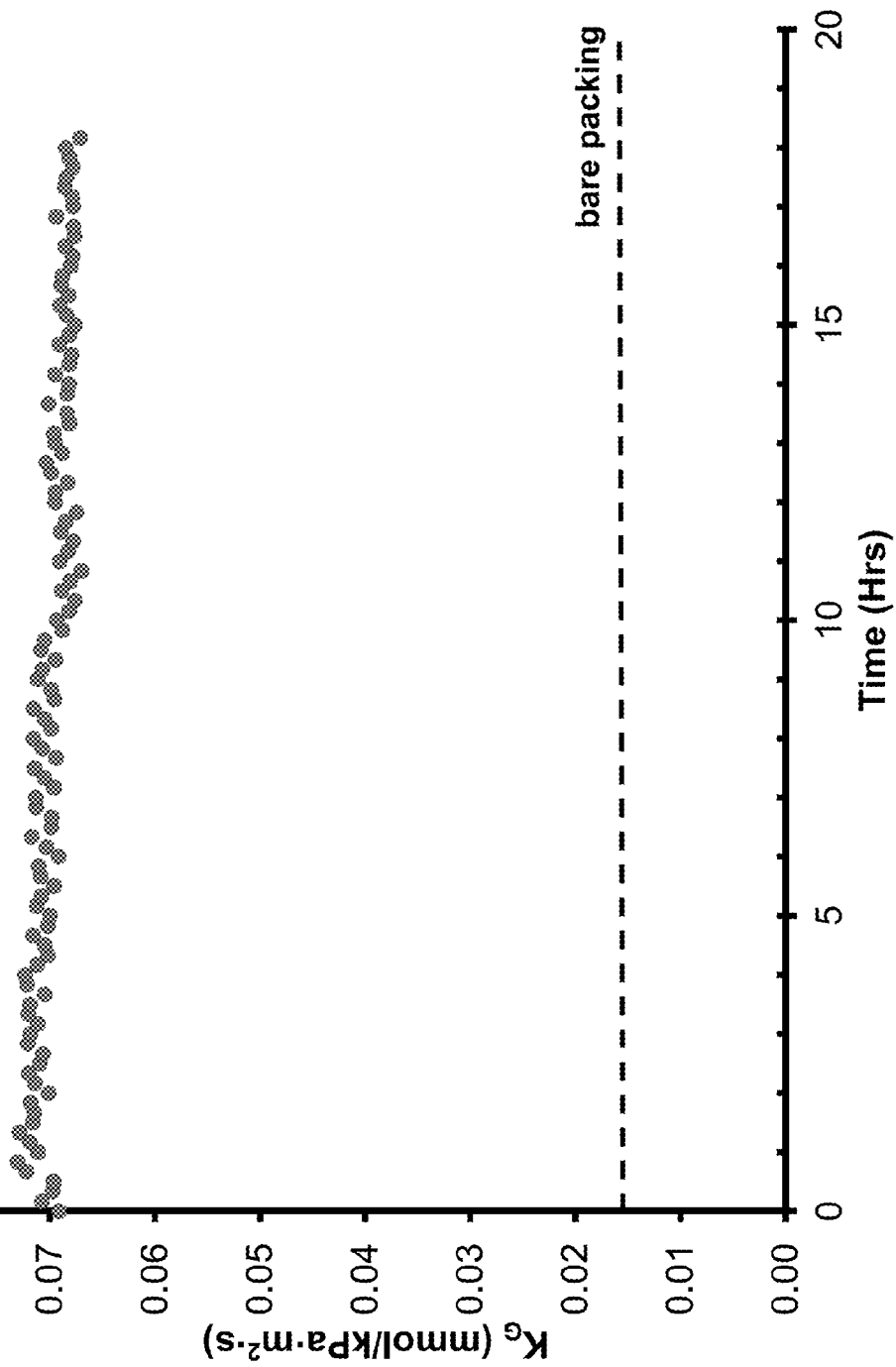
FIG. 22 shows the $K_G$ of a 2" Sulzer packing unit coated using the adhesive method described in Example 29 produced using a xerogel powder prepared using phosphate buffer dilution according to Example 1.

In FIG. 22, a xerogel powder prepared according to the experimental procedure described in Example 1 was adhere to Sulzer packing using epoxy adhesive and tested for activity in the CLR. The sample showed an average $K_G$ of 0.070 mmol/s-m²-kPa, corresponding to a 4.4 fold enhancement over the blank.

The above examples show that commercial adhesives can be used to bind xerogel particles to solid supports for use in enzymatic carbon capture processes.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

The invention claimed is:

1. A coated support comprising a polysilicate-polysilicone copolymer immobilizing a biocatalyst; the polysilicate-polysilicone copolymer adhered to a solid support by an adhesive coating and wherein the biocatalyst comprises a carbonic anhydrase.

2. A coated support comprising
a solid support;
a coating composition forming a layer on the surface of the solid support, the coating composition comprising a polysilicate-polysilicone copolymer and a hydrophilic additive; and
a biocatalyst that catalyzes hydration of carbon dioxide being entrapped in the coating composition;
wherein the biocatalyst comprises a carbonic anhydrase.

3. The coated support of claim 1 wherein the adhesive coating comprises a polymer adhesive.

4. The coated support of claim 3 wherein the polymer adhesive comprises a urethane polymer, an epoxy polymer, a resin, a cyanoacrylate polymer, a methacrylate polymer, or a combination thereof.

5. The coated support of claim 3 wherein the polymer adhesive comprises a two-part epoxy polymer.

6. The coated support of claim 2 wherein the coating composition is derived from reaction of a sol, the sol comprising (i) an alkoxy silane or an organotrialkoxy silane or metasilicate, (ii) a poly(silicone), (iii) a hydrophilic additive, and (iv) the carbonic anhydrase.

7. The coated support of claim 6 wherein the coating composition is derived from reaction of the sol and a catalyst.

8. The coated support of claim 6 wherein the poly(silicone) comprises a poly(siloxane).

9. A process for removing $CO_2$ from a $CO_2$-containing gas, the process comprising
contacting a liquid with a $CO_2$-containing gas; and contacting the $CO_2$ in the liquid with the coated support of claim 2 to catalyze hydration of the $CO_2$ and form a treated liquid comprising hydrogen ions and bicarbonate ions.

10. The process of claim 9 wherein the hydration of the $CO_2$ takes place in a reaction vessel comprising a bottom portion containing a gas inlet and a liquid outlet, a top portion containing a liquid inlet and a gas outlet, and a middle portion containing a plurality of the coated supports of claim 2, the carbonic anhydrase being capable of catalyzing hydration of $CO_2$ into hydrogen ions and bicarbonate ions.

11. The process of claim 10 wherein the coated supports are packed in the middle portion of the reaction vessel.

12. The coated support of claim 6 wherein the alkoxy silane comprises tetramethylorthosilicate, tetraethylorthosilicate, methyltriethylorthosilicate, ethyltrimethylorthosilicate, dimethyldiethylorthosilicate, tetraglyceryl silicate, or a combination thereof 13. The coated support of claim 6 wherein the organotrialkoxy silane comprises trimethoxymethylsilane, trimethoxyethylsilane, or a combination thereof 14. The coated support of claim 13 wherein the alkoxy silane comprises tetramethylorthosilicate.

15. The coated support of claim 13 wherein the poly(silicone) comprises a poly(siloxane) selected from the group consisting of poly(dimethylsiloxane), poly(dimethylsiloxane)-co-poly(alkene oxide), or a combination thereof.

16. The coated support of claim 14 wherein the poly(siloxane) comprises polydimethylsiloxane.

17. The coated support of claim 15 wherein the poly(silicone) is silanol-terminated.

18. The coated support of claim 2 wherein the hydrophilic additive comprises poly(vinyl alcohol), poly(ethylene oxide), a quaternary ammonium polymer, a crown ether, a cyclodextrin, a surfactant, hexadecyltrimethylammonium bromide, poly(1-methyl-4-vinylpyridinium bromide), poly(acrylamide-methacryloxyethyltrimethylammonium bromide), or a combination thereof.

19. The coated support of claim 6 wherein the hydrophilic additive is a crown ether and the crown ether comprises 12-crown-4, 1,7-diaza-12-crown-4, 1,4,8,11-tetrathiacyclotetradecane, 1,4,8,12-tetraazacyclopentadecane, 15-crown-5, 18-crown-6, dibenzo-18-crown-6, dicyclohexano-18-crown-6, (18-crown-6)-2,3,11,12-tetracarboxylic acid, 1-aza-18-crown-6, diaza-18-crown-6, or a combination thereof.

20. The coated support of claim 19 wherein the crown ether comprises 18-crown-6.

21. The coated support of claim 20 wherein the alkoxy silane comprises tetramethylorthosilicate and the poly(silicone) comprises polydimethylsiloxane.

22. The process of claim 11 wherein the coating composition is derived from reaction of a sol, the sol comprising (i) an alkoxy silane or an organotrialkoxy silane or metasilicate, (ii) a poly(silicone), (iii) a hydrophilic additive, and (iv) the carbonic anhydrase; the alkoxy silane comprises tetramethylorthosilicate, the poly(siloxane) comprises polydimethylsiloxane, and the hydrophilic additive comprises a crown ether.

23. The coated support of claim 6 wherein the alkoxy silane comprises tetramethylorthosilicate, the poly(siloxane) comprises polydimethylsiloxane, and the hydrophilic additive comprises a crown ether.

24. The coated support of claim 6 wherein the coating composition is derived from reaction of a sol, the sol comprising (i) an alkoxy silane or an organotrialkoxy silane or metasilicate, (ii) a poly(silicone), (iii) a hydrophilic additive, and (iv) the carbonic anhydrase; the alkoxy silane comprises tetramethylorthosilicate, the poly(siloxane) comprises polydimethylsiloxane, and the hydrophilic additive comprises a crown ether.

25. The coated support of claim 2 wherein the coating composition has an overall pore volume of at least about 3 µL/g to 500 µL/g.

* * * * *